US008871191B2

(12) United States Patent
Pavlakis et al.

(10) Patent No.: US 8,871,191 B2
(45) Date of Patent: Oct. 28, 2014

(54) USE OF IL-15 PREPARATIONS TO TREAT LYMPHOPENIA

(75) Inventors: George N. Pavlakis, Rockville, MD (US); Barbara K. Felber, Rockville, MD (US); Antonio Valentin, Frederick, MD (US); Cristina Bergamaschi, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/390,504

(22) PCT Filed: Aug. 13, 2010

(86) PCT No.: PCT/US2010/045511

§ 371 (c)(1), (2), (4) Date: Feb. 14, 2012

(87) PCT Pub. No.: WO2011/020047

PCT Pub. Date: Feb. 17, 2011

(65) Prior Publication Data

US 2012/0141413 A1 Jun. 7, 2012

Related U.S. Application Data

(60) Provisional application No. 61/234,152, filed on Aug. 14, 2009, provisional application No. 61/234,155, filed on Aug. 14, 2009.

(51) Int. Cl.

| | |
|---|---|
| ***A61K 38/20*** | (2006.01) |
| ***A61K 47/48*** | (2006.01) |
| ***C07K 14/54*** | (2006.01) |
| ***A61K 45/06*** | (2006.01) |
| ***A61K 38/17*** | (2006.01) |
| *A61K 48/00* | (2006.01) |
| *C12N 15/85* | (2006.01) |

(52) U.S. Cl.

CPC ....... *A61K 38/2086* (2013.01); *A61K 47/48423* (2013.01); *C07K 14/5443* (2013.01); *A61K 48/005* (2013.01); *A61K 45/06* (2013.01); *A61K 47/48507* (2013.01); *A61K 38/1793* (2013.01)

USPC ....... 424/85.2; 435/320.1; 435/375; 435/455; 530/351; 514/44 R

(58) Field of Classification Search

None

See application file for complete search history.

(56) References Cited

U.S. PATENT DOCUMENTS

| | | | |
|---|---|---|---|
| 5,552,303 | A | 9/1996 | Grabstein et al. |
| 5,574,138 | A | 11/1996 | Grabstein et al. |
| 6,001,973 | A | 12/1999 | Strom et al. |
| 6,063,911 | A | 5/2000 | Vournakis et al. |
| 6,451,308 | B1 | 9/2002 | Strom et al. |
| 6,548,065 | B1 | 4/2003 | Anderson et al. |
| 6,764,836 | B2 | 7/2004 | Anderson et al. |
| 6,787,132 | B1 | 9/2004 | Gabizon et al. |
| 6,864,245 | B2 | 3/2005 | Vournakis et al. |
| 6,998,476 | B2 | 2/2006 | Strom et al. |
| 7,067,132 | B2 | 6/2006 | Grabstein et al. |
| 7,112,436 | B1 | 9/2006 | Rose-John |
| 7,258,853 | B2 | 8/2007 | Strom et al. |
| 7,435,596 | B2 | 10/2008 | Campana et al. |
| 7,638,604 | B2 | 12/2009 | Li et al. |
| 8,124,084 | B2 | 2/2012 | LeFrancois et al. |
| 8,163,879 | B2 | 4/2012 | Wong et al. |
| 8,224,578 | B2 | 7/2012 | Raab et al. |
| 2002/0022030 | A1 | 2/2002 | Marrack et al. |
| 2002/0114781 | A1 | 8/2002 | Strom et al. |
| 2002/0127201 | A1 | 9/2002 | Boussiotis et al. |
| 2002/0128436 | A1 | 9/2002 | Strom et al. |
| 2002/0182178 | A1 | 12/2002 | Grooten et al. |
| 2003/0105295 | A1 | 6/2003 | Strom et al. |
| 2003/0236255 | A1 | 12/2003 | Waer et al. |
| 2004/0087015 | A1 | 5/2004 | Vournakis et al. |
| 2004/0170604 | A1 | 9/2004 | Ekida et al. |
| 2004/0253587 | A1 | 12/2004 | Grabstein et al. |
| 2005/0032167 | A1 | 2/2005 | Anderson et al. |
| 2005/0042220 | A1 | 2/2005 | Li et al. |
| 2005/0202005 | A1 | 9/2005 | Winchester et al. |
| 2006/0057102 | A1 | 3/2006 | Zheng et al. |
| 2006/0057680 | A1 | 3/2006 | Zheng et al. |
| 2006/0093605 | A1 | 5/2006 | Campana et al. |

(Continued)

FOREIGN PATENT DOCUMENTS

| | | | |
|---|---|---|---|
| EP | 1777294 | A1 | 4/2007 |
| WO | WO 95/27722 | A1 | 10/1995 |
| WO | WO 95/30695 | A1 | 11/1995 |
| WO | WO 96/37223 | A1 | 11/1996 |
| WO | WO 97/41232 | A1 | 11/1997 |

(Continued)

OTHER PUBLICATIONS

Wells, 1990, Biochemistry 29:8509-8517.*

Bork, 2000, Genome Research 10:398-400.*

Skolnick et al., 2000, Trends in Biotech. 18(1):34-39.*

Tokuriki and Tawflik,Current Opinion in Structural Biology 2009, 19: 596-604.*

(Continued)

*Primary Examiner* — Bridget E Bunner

*Assistant Examiner* — Fozia Hamud

(74) *Attorney, Agent, or Firm* — Kilpatrick Townsend & Stockton LLP

(57) ABSTRACT

The present invention provides method for promoting the maturation and export of T cells from thymic tissue by contacting the thymic tissue with supraphysiological levels of interleukin (IL)-15. The present invention also provides methods for preventing, alleviating, reducing, and/or inhibiting lymphopenia or peripheral depletion of lymphocytes in a patient in need thereof by administering to the patient IL-15.

15 Claims, 23 Drawing Sheets

(56) References Cited

U.S. PATENT DOCUMENTS

| | | | |
|---|---|---|---|
| 2006/0104945 | A1 | 5/2006 | Choi |
| 2006/0147419 | A1 | 7/2006 | Perera et al. |
| 2006/0165668 | A1 | 7/2006 | Liu et al. |
| 2006/0257361 | A1 | 11/2006 | Watanabe et al. |
| 2006/0263857 | A1 | 11/2006 | LeFrancois et al. |
| 2007/0110714 | A1 | 5/2007 | Hayashi |
| 2007/0134718 | A1 | 6/2007 | Grooten et al. |
| 2007/0141557 | A1 | 6/2007 | Raab et al. |
| 2007/0160578 | A1 | 7/2007 | Waldmann |
| 2008/0255039 | A1 | 10/2008 | Bernard et al. |
| 2009/0017000 | A1 | 1/2009 | Cai et al. |
| 2009/0082299 | A1 | 3/2009 | Felber et al. |
| 2009/0238791 | A1 | 9/2009 | Jacques et al. |
| 2011/0081311 | A1 | 4/2011 | Pavlakis et al. |
| 2012/0230946 | A1 | 9/2012 | Wong et al. |

FOREIGN PATENT DOCUMENTS

| | | | |
|---|---|---|---|
| WO | WO 98/36768 | A1 | 8/1998 |
| WO | WO 00/02582 | A2 | 1/2000 |
| WO | WO 00/36918 | A1 | 6/2000 |
| WO | WO 00/62805 | A1 | 10/2000 |
| WO | WO 01/80889 | A1 | 11/2001 |
| WO | WO 02/22805 | A2 | 3/2002 |
| WO | WO 2004/059556 | A2 | 7/2004 |
| WO | WO 2005/085282 | A1 | 9/2005 |
| WO | WO 2006/020849 | A2 | 2/2006 |
| WO | WO 2007/001677 | A2 | 1/2007 |
| WO | WO 2007/046006 | A2 | 4/2007 |
| WO | 2007/084342 | | 7/2007 |
| WO | WO 2007/095643 | A2 | 8/2007 |
| WO | WO 2008/089144 | A2 | 7/2008 |
| WO | WO 2009/002562 | A2 | 12/2008 |

OTHER PUBLICATIONS

Sandau et al, The Journal of Immunology, 2007, vol. 179, pp. 120-125.*

Zhang et al, (Immunity, 1998, vol. 8, pp. 591-599.*

Bergamaschi et al, The Journal of Immunology, 2009, vol. 183, pp. 3064-3072.*

Cao et al, (Cancer Res 1998; vol. 58, pp. 1695-1699.*

International Search Report dated Nov. 11, 2011, issued in related International Patent Application No. PCT/US2010/045511, filed Aug. 13, 2010.

Aipdogan et al., "Interleukin-15 enhances immune reconstitution after allogeneic bone marrow transplantation," 2005, Blood, vol. 105, No. 2, 365-873.

Jalah et al., "Efficient Systematic Expression of Bioactive IL-15 in Mice upon Delivery of Optimized DNA Expression Plasmids," 2007, DNA and Cell Biology, vol. 26, No. 12, pp. 827-840.

Williams et al., "T cell immune reconstitution following lymphodepletion," 2007, Seminars in Immunology, 19, pp. 318-330.

Chirifu et al, "Crystal structure of the IL-15-IL-15Ralpha complex, a cytokine-receptor unit presented in trans," *Nat. Immunol.*, 8: 1001-1007, 2007.

Olsen, et al., "Crystal structure of the interleukin-15 Interleukin-15 receptor alpha complex," *Journal of Biological Chemistry*, 282(51): 37191-37204, Dec. 21, 2007.

Dubois et al, "IL-15Rα Recycles and Presents IL-15 in trans to Neighboring Cells," *Immunity*, vol. 17, Nov. 2002, 537-547.

Giron-Michel, et al., "Membrane-Bound and Soluble IL-15/1L-15Rα Complexes Display Differential Signalling and Functions on Human Hematopoietic Progenitors," *Blood*, Oct. 1, 2005, vol. 106, No. 7, 2302-2310.

Mortier et al., "Natural, Proteolytic Release of a Soluble Form of Human IL-15 Receptor α-Chain That Behaves as a Specific, High Affinity IL-15 Antagonist " *The Journal of Immunology*, 2004, 173: 1681-1688.

Mortier et al., "Soluble Interleukin-15 Receptor α (IL-15Rα)-sushi as a Selective and Potent Agonist of IL-15 Through IL-15Rβ/g," *Journal of Biological Chemistry*, vol. 281, No. 3, Jan. 20, 2006, 1612-1619.

Oh, et al., "IL-15/IL-15Rα-Mediated Avidity Maturation of Memory CD8+ T Cells," *PNAS*, Oct. 19, 2004, vol. 101, No. 42, 15154-15159.

Overwijk, et al., Functions of γC cytokines in immune homeostasis: Current and potential clinical applications, *Clin Immunol* (2009) 132:153-165.

Rubinstein et al., "Converting IL-15 to a Superagonist by Binding to Soluble IL-15Rα," *PNAS*, Jun. 13, 2006, vol. 103, No. 24, 9166-9171.

Stoklasek et al., "Combined IL-15/IL-15Rα Immunotherapy Maximizes IL-15 Activity In Vivo," *The Journal of Immunology*, 2006, 177: 6072-6080.

Alpdogan et al., 2005, "IL-7 and IL-15: therapeutic cytokines for Immunodeficiency", Trends Immunol; 26:56-64.

Altman,et al., 1996, "Phenotypic analysis of antigen-specific T lymphocytes", Science; 274:94-96.

Anderson et al., 1995, "Functional characterization of the human interleukin-15 receptor alpha chain and close linkage of IL15RA and IL2RA genes", Journal of Biological Chemistry; 270(50):29862-29869, Table 1, p. 29865.

Armitage et al., 1995, "IL-15 has stimulatory activity for the induction of B cell proliferation and differentiation", J. Immunol; 154:483-490.

Ausubel et al., 1993, Current Protocols in Molecular Biology, John Wiley & Sons, pp. 2.10.1-2.10.16.

Baccala, 2005, "Tumor immunity via homeostatic T cell proliferation: mechanistic aspects and clinical perspectives", Springer Semin Immunopathol published online.

Badoual et al., 2008, "The soluble alpha chain of interleukin-15 receptor: a proinflammatory molecule associated with tumor progression in head and neck cancer," Cancer Res; 68(10):3907-3914.

Bamford et al., 1994, "The interleukin (11)-2 receptor-beta chain is shared by 11-2 and a cytokine, provisionally designated ii-t, that stimulates Tcell proliferation and the induction of lymphokine-activated killer-cells", Proceedings of the National Academy of Sciences USA; 91:4940-4944.

Bamford et al., 1996, "Interleukin (IL)15/IL-T production by the adult T-cell leukemia cell line HuT-102 is associated with a human T-celilymphotrophic virus type I region /IL-15 fusion message that lacks many upstream AUGs that normally attenuates IL-15 mRNA translation", Proc. Natl. Acad. Sci. USA; 93:2897-2902.

Bamford et al., 1998, "The 5' untranslated region, signal peptide, and the coding sequence of the carboxyl terminus of IL-15 participate in its multifaceted translational control", Journal of Immunology; 160:4418-4426.

Becker et al., 2002, "Interleukin 15 is required for proliferative renewal of virus-specific memory CD8 T cells", J Exp Med; 195:1541-1548.

Berard et al., 2003, "IL-15 promotes the survival of naive and memory phenotype CD8(+) T cells", Journal of Immunology; 170:5018-5026.

Berger et al., 2009, "Safety and immunologic effects of IL-15 administration in nonhuman primates," Blood; 114:2417-2426.

Bernard et al., 2004, "Identification of an interleukin-15α receptor-binding site on human interleukin-15," J Biol Chem; 279:24313-24322.

Bindon et al., 1983, "Clearance rates and systemic effects of intravenously administered interleukin 2 (IL-2) containing preparations in human subjects," Br. J. Cancer, 47:123-133.

Brocker, 1997, "Survival of mature CD4 T lymphocytes is dependent on major histocompatibility complex class II-expressina dendritic cells", J Exp Med; 186:1223-1232.

Budagian et al., 2004, "Reverse signaling throlJgh membrane-bound interleukin-15", J Biol Chem; 279:42192-42201.

Burkett et al, 2004, "Coordinate expression and trans presentation of interleukin (IL)-15Ralpha and IL-15 supports natural killer cell and memory CD8+ T cell homeostasis", J Exp Med; 200:825-834.

Burkett et al., 2003, "IL-15R alpha expression on CD8+ T cells is dispensable for T cell Memory", Proc Natl Acad Sci USA; 100:4724-4729.

Burton et al., 1994, "A lymphokin , provisionally designated interleukin-t and produced by a human adult T-cell leukemia line, stimulates T-cell proliferation and the induction of lymphokine-activated killer-cells", Proc Natl Acad Sci USA; 91:4935-4939.

(56) References Cited

OTHER PUBLICATIONS

Carson et al., 1994, "Interleukin (IL) 15 is a novel cytokine that activates human natural killer cells via components of the IL-2 receptor", J Exp Med; 180:1395-1403.
Castelli et al., 2004, "Mature dendritic cells can enhance CD8+ cell noncytotoxic anti-HIV responses: the role of IL-15", Blood; 103:2699-2704.
Chapoval et al., 1998, "Combination chemotherapy and IL-15 administration induce permanent tumor regression in a mouse lung tumor model: NK and T cell-mediated effects antagonized by B cells", J Immunol; 161:6977-6984.
Chehimi et al., 1997, "IL-15 enhances immune functions during HIV infection", Journal of Immunology; 158(12):5978-5987.
Chitnis et al., 2003, "Determinants of HIV-Specific CD8 T-cell responses in HIV-infected pediatric patients and enhancement of HIV-gagspecitic responses with exogenous IL-15", Clin Immunol; 107:36-45.
Cho et al., 2000, "Homeostasis-stimulated proliferation drives naive T cells to differentiate directly into memory T cells", J Exp Med; 192:549-556.
Cooper et al., 2002, "In vivo evidence for a dependence on interleukin 15 for survival of natural killer cells", Blood; 100:3633-3638.
Database EMBL, Accession No. U31628, Dec. 23, 1995, "Human interleukin-15 receptor alpha chain precursor (IL15RA) mRNA, complete CDS."
Davis et al., 1991, "Reduction of Immunogenicity and Extension of Circulating Half-life of Peptides and Proteins," Peptide and Protein Drug Delivery, Marcel Deker Inc., New York, pp. 831-864.
Dean et al., 2005, "Cloning and expression of feline interleukin 15," Cytokine; 29(2):77-83.
De Jong et al., 1996, "Interaction of IL-15 with the shared IL-2 receptor beta and gamma c subunits. The IL-15/beta/gamma c receptor-ligand complex is less stable than the IL-2/beta/gamma c receptor-ligand complex", J Immunol; 156:1339-1348.
Dubois et al., 1999, "Natural splicing of exon 2 of human interleukin-15 receptor α-chain mRNA results in a shortened form with a distinct pattern of expression," J Biol Chem; 274:26978-26984.
Dudley et al., 2005, "Adoptive cell transfer therapy following nonmyeloablative but lymphodepleting chemotherapy for the treatment of patients with refractory metastatic melanoma", J Clin Oncol; 23:2346-2357.
Dummer et al., 2002, "T cell homeostatic proliferation elicits effective antitumor autoimmunity", J Clin Invest; 110:185-192.
Dunne et al., 2001, "Selective expansion and partial activation of human NK cells and NK receptor-positive T cells by IL-2 and IL-15", J Immunol; 167-3129-3138.
EMBL Database accession No. BC074726, "Homo sapiens interleukin 15 receptor, alpha, transcript variant 1, m RNA (cDNA clone MGC:103798 Image:30915179), complete cds", dated Aug. 4, 2004.
Epardaud et al., 2008, "Interleukin-15/interleukin-15Rα complexes promote destruction of established tumors by reviving tumor-resident CD8+ T cells," Cancer Res; 68:2972-2983.
Fehniger et al., 2001, "Interleukin 15: biology and relevance to human disease," Blood; 97:14-32.
Ferrari-Lacraz et al., 2004, "Targeting IL-15 receptor-bearing cells with an antagonist mutant IL-15/FC protein prevents disease development and progression in murine collagen-induced arthritis", J Immunol; 173:5818-5826.
Fewkes et al., 2010, "Novel gamma-chain cytokines as candidate immune modulators in immune therapies for cancer," J Cancer; 16:392-398.
Fischer et al., 1997, "A bioactive designer cytokine for human hematopoietic progenitor cell expansion", Nat Biotechnol; 15(2):142-145.
Forcina et al., 2004, "Interleukin-15 modulates interferon-gamma and betachemokine production in patients with HIV infection: implications for immune-based therapy", Cytokine; 25:283-290.
Giri et al., 1994, "Utilization of the beta and gamma chains of the IL-2 receptor by the novel cytokine IL-15", EMBO J; 13:2822-2830.
Giri et al., 1995, "Identification and cloning of a novel IL-15 binding protein that is structurally related to the alpha chain of the IL-2 receptor", EMBO J; 15:3654-3633.
Giri et al., 1995, "IL-15, a novel T cell growth factor that shares activities and receptor components with IL-2", J Leukocyte Biol.; 57:763-766.
Goldrath et al., 2002, "Cytokine requirements for acute and basal homeostatic proliferation of naive and memory CD8+ T cells", J Exp Med; 195:1515-1522.
Goldrath et al., 2000, "Low-affinity ligands for the TCR drive proliferation of mature CD8+ Tcells in lymphopenic hosts", Immunity; 11:183-190.
Grabstein et al., 2004, "Cloning of a T cell growth factor that interacts with the beta chain of the interleukin-2 receptor", Science; 264:965-968.
Hsu et al., 2005, "Primary human T lymphocytes engineered with a codon-optimized IL-15 gene resist cytokine withdrawal-induced apoptosis and persist long-term in the absence of exogenous cytokine", J Immunol; 175:7226-7234.
Johnston et al., 1995, "Tyrosine phosphorylation and activation of STAT5, STAT3, and Janus kinases by interleukins 2 and 15", Proc Natl Acad Sci U S A. 92(19):8705-8709.
Judge et al., 2002, "Interleukin 15 controls both proliferation and survival of a subset of memory—phenotype CD8(+) T Cells", J Exp Med; 196:935-946.
Jung et al., 2002, "In vivo depletion of CD11c(+) dendritic cells abrogates priming of CD8(+) T cells by exogenous cell-associated antigens", Immunity; 17:211-220.
Kassiotis et al., 2002, "Impairment of immunological memory in the absence of MHC despite survival of memory T cells", Nat Immunol; 3:244-250.
Kennedy et al., 2000, "Reversible defects in natural killer and memory CD8 T cell lineages in Interleukin-15-deficient mice", J Exp Med; 191:771-780.
Khan et al., 1996, "IL-15 augments CD8+ T cell-mediated immunity against *Toxoplasma gondii* infection in mice", J Immunol; 157(5):2103-2108.
Khan et al., 2002, "Treatment with soluble interleukin-15Rα exacerbates intracellular parasitic infection by blocking the development of memory CD8+ T cell response," J Exp Med; 195(11):1463-1470.
Kieper et al., 2000, "Homeostatic expansion and phenotypic conversion of naive T cells in response to self peptide/MHC ligands", PNAS; 96:13306-13311.
Kim et al., 1998, "Generation of mucosal cytotoxic T cells against soluble protein by tissue specific environmental and costimulatory signals", Proc Natl Acad Sci USA; 95:10814-10819.
Kishimoto, 2010, "IL-6: from its discovery to clinical applications", International Immunology; 22(5):347-352.
Klebanoff et al., 2004, "IL-15 enhances the in vivo antitumor activity of tumorreactive CD8+ T cells", Proc Natl Acad Sci USA; 101:1969-1974.
Kobayashi et al., 2000, "Differences in biodistribution, pharmacokinetics, and tumor targeting between interleukins 2 and 15", Cancer Research; 60:3577-3583.
Koka et al., 2003, "Interleukin (IL)-15R[alpha]-deficient natural killer cells survive in normal but not IL-15R[alpha]-deficient mice", J Exp Med; 197:977-984.
Krause et al., 1996, "Genomic structure and chromosomal localization of the human interleukin 15 gene (IL-15)", Cytokine. 8(9):667-674.
Ku et al., 2000, "Control of homeostasis of CD8+ memory T cells by opposing cytokines", Science; 288:675-678.
Kutzler et al., 2005, "Coimmunization with an optimized IL-15 plasmid results in enhanced function and longevity of CD8 T cells that are partially independent of CD4 T cell help," J Immunol; 175:112-123.
Lodolce et al., 1998, "IL-15 receptor maintains lymphoid homeostasis by supporting lymphocyte homing and proliferation", Immunity; 9:669-676.
Lodolce et al., 2001, "T cell independent interleukin 15R alpha signals are required for bystander proliferation", J Exp Med; 194:1187-1194.

(56) References Cited

OTHER PUBLICATIONS

Lum et al., 2004, "Differential Effects of Interleukin-7 and Interleukin-15 on NK Cell Anti-Human Immunodeficiency Virus Activity", J Viral; 78:6033-6042.
Lyons et al., 1994, "Determination of lymphocyte division by flow cytometry", J Immunol Methods. 2;171(1):131-137.
Maeurer et al., 2000, "Interleukin-7 or interleukin-15 enhances survival of *Mycobacterium tuberculosis*-infected mice", Infect Immun; 68:2962-2970.
Masopust et al., 2001, "Direct analysis of the dynamics of the intestinal mucosa CD8 T cell response to systemic virus infection", J Immunol; 166:2348-2356.
Mastroianni et al., 2000, "Interleukin-15 enhances neutrophil functional activity in patients with human immunodeficiency virus infection", Blood; 96:1979-1984.
Matsumoto et al., 2003, "On-column refolding and characterization of soluble human interleukin-15 receptor alpha-chain produced in *Escherichia coli*", Protein Expr Purif; 31(I):64-71.
Mueller et al., 2003, "IL-15 enhances survival and function of HIV-specific CD8+ T cells", Blood; 101(3):1024-1029.
Murali-Krishna et al., 1999, "Persistence of memory CD8 T cells in MHC class I-deficient mice", Science; 286:1377-1381.
Nguyen et al., 2000, "TNF receptor 1 (TNFR1) and CD95 are not required for T cell deletion after virus infection but contribute to peptide-induced deletion under limited conditions", Eur J Immunol; 30:683-688.
Nishimura et al., 2005, "A novel autoregulatory mechanism for transcriptional activation of the IL-15 gene by a nonsecretable isoform of IL-15 generated by alternative splicing", FASEB J; 19:19-28.
Oehen et al., 1998, "Differentiation of naive CTL to effector and memory CTL: correlation of effector function with phenotype and cell division", J Immunol; 161;5338-5346.
Oh et al., 2003, "Coadministration of HIV vaccine vectors with vaccinia viruses expressing IL-15 but not IL-2 induces long-lasting cellular immunity", PNAS; 100:3392-3397.
Ohteki et al., 2001, "Critical role of IL-15-IL-15R for antigen-presenting cell functions in the innate immune response", Nat Immunol; 2:1138-1143.
Park et al., 2004, "Follicular dendritic cells produce IL-15 that enhances germinal B cell proliferation in membrane-bound form", J Immunol; 173:6676-6683.
Pereno et al., 2000, "IL-15/IL-15Ralpha intracellular trafficking in human melanoma cells and signal transduction through the IL-15Ralpha", Oncogene. 19(45):5153-5162.
Pettit et al., 1997, "Structure-function studies of interleukin 15 using site-specific mutagenesis, polyethylene glycol conjugation, and homology modeling", J Biol Chem; 272(4):2312-2318.
Pflanz el al., 1999, "A fusion protein of interleukin-11 and soluble interleukin-11 receptor acts as a superagonist on cells expressing gp130", FESB Lett; 450:117-122.
Porter et al., 2005, "T-cell reconstitution and expansion after hematopoietic stem cell transplantation: 'T' it up!", Bone Marrow Transplant; 35:935-942.
Prlic et al., 2003, "In vivo survival and homeostatic proliferation of natural killer cells", J Exp Med; 197:967-976.
Roychowdhury et al., 2004, "Failed adoptive immunotherapy with tumorspecific T cells: reversal with low-dose interleukin 15 but not low-dose interleukin 2", Cancer Res; 64:8062-8067.
Rubinstein et al., 2002, "Systemic administration of IL-15 augments the antigen-specific primary CD8+ T Cell response following vaccination with peptide-pulsed dendritic cells", J Immunol; 169:4928-4935.
Ruchatz et al., 1998, "Soluble IL-15 receptor alpha-chain administration prevents murine collagen-induced arthritis: a role for IL-15 in development of antigen-induced immunopathology", J Immunol; 160:5654-5660.
Ruckert et al., 2003, "Dendritic cell-derived IL-15 controls the induction of CDS T cell immune responses", Eur J Immunol; 33:3493-3503.
Sandau et al., 2004, "Transpresentation of IL-15 by bone marrow-derived cells necessitates expression of IL-15 and IL-15R by the same cells", J Immunol; 173(11):6537-6541.
Sato et al., 2007, "The IL-15/IL-15 Rα on cell surfaces enables sustained IL-15 activity and contributes to the long survival of CD8 memory T cells", Proc Natl Acad Sci USA; 104(2):588-593.
Scheeler et al., 2006, "Interleukin-6 and its receptor: from bench to bedside", Med Microbiol Immunol; 195:173-183.
Schluns et al., 2000, "Interleukin-7 mediates the homeostasis of naive and memory CD8 T cells in vivo", Nat Immunol; 1:426-432.
Schluns et al., 2002, "Requirement for IL-15 in the generation of primary and memory antigen specific CD8 T cells", J Immunol; 168:4827-4831.
Schluns et al., 2004, "Distinct cell types control lymphoid subset development by means of IL-15 and IL-15 receptor alpha expression", Proc Natl Acad Sci USA; 101:5616-5621.
Schluns et al., 2004, "Trans-regulation of memory CD8 T cell proliferation by IL-15Ra+ bone marrow-derived cells", Blood; 103(3):988-994.
Schluns et al., 2005, "The roles of interleukin-15 receptor α: Trans-presentation, receptor component, or both?" Int J Biochem Cell Biol; 37:1567-1571.
Smith et al., 2000, "Selective blockade of IL-15 by soluble IL-15 receptor alpha-chain enhances cardiac allograft survival", J Immunol; 165(6):3444-3450.
Tan et al., 2000, "Interleukin (IL)-15 and IL-7 jointly regulate homeostatic proliferation of memory phenotype CD8+ cells but are not required for memory phenotype CD4+ cells", J Exp Med; 195:1523-1532.
Tsunobuchi et al., 2000, "A protective role of interleukin-15 in a mouse model for systemic infection with herpes simplex virus," Virology, 275:57-66.
Umemura et al., 2001, "Overexpression of IL-15 in vivo enhances protection against *Mycobacterium bovis* bacillus Calmette-Guerin infection via augmentation of NK and T cytotoxic 1 responses", J Immunol; 167:946-956.
Van Belle et al., 2005, "IL-15 and IL-15Rα in CD4+. T cell immunity," Arch Immunol Ther Exp; 53(2):115-126.
Villinger et al., 2004, "IL-15 is superior to IL-2 in the generation of long-lived antigen specific memory CD4 and CD8 T cells in rhesus macaques", Vaccine; 22:3510-3521.
Waldmann et al., 1999, "The multifaceted regulation of interleukin-15 expression and the role of this cytokine in NK cell differentiation and host response to intracellular pathogens," Annu Rev Immunol., vol. 17:19-49.
Waldmann et al., 2001, "Contrasting roles of IL-2 and IL-15 in the life and death of lymphocytes: implications for immunotherapy," Immunity, vol. 14:105-110.
Waldmann, T.A., 2006, "The biology of interleukin-2 and interleukin-15: implications for cancer therapy and vaccine design," Nat Rev Immunol., vol. 6:595-601.
Wang et al., 1987, "The interleukin 2 receptor", Journal of Experimental Medicine; 166:1055-1069.
Warren et al., 1996, "Analysis of the costimulatory role of IL-2 and IL-15 in initiating proliferation of resting (CD56dim) human NK cells", J Immunol; 156:3254-3259.
Wei et al., 2001, "The Sushi domain of soluble IL-15 receptor α is essential for binding IL-15 and inhibiting inflammatory and allogenic responses in vitro and in vivo," J Immunol., vol. 167:277-282.
Wrzesinski et al., 2005, "Less is more: lymphodepletion followed by hematopoietic stem cell transplant augments adoptive T-cell-based antitumor immunotherapy", Curr Opin Immunol; 17:195-201.
Wysocka et al., 2004, "Enhancement of the host immune responses in cutaneous T-cell lymphoma by CpG oligodeoxynucleotides and IL-15", Blood; 104:4142-4149.
Zammit et al., 2005, "Dendritic cells maximize the memory CD8 T cell response to infection", Immunity. 22(5):561-70.
Zeng et al., 2005, "Synergy of IL-21 and IL-15 in regulating CD8+ T cell expansion and Function", J Exp Med; 201:139-148.
International Search Report of International application No. PCT/US2006/19403, dated May 11, 2007.

(56) References Cited

OTHER PUBLICATIONS

Written Opinion of International application No. PCT/US2006/19403, dated May 11, 2007.
International Search Report of International application No. PCT/US2008/008084, dated Dec. 30, 2008.
International Preliminary Report on Patentability of International application no. PCT/US2008/008084, dated Jan. 5, 2010.
Written Opinion of International application No. PCT/US2008/008084, dated Dec. 30, 2008.
Supplementary European Search Report of EP application No. 06784439.9-2401, dated Apr. 22, 2009.
Supplementary European Search Report of EP application No. 11154217.1, dated Nov. 14, 2011.
Office Action of EP application No. 10752466.2, dated Feb. 13, 2014.
Office Action of U.S. Appl. No. 11/435,497, dated Feb. 25, 2009.
Office Action of U.S. Appl. No. 11/435,497, dated Jan. 13, 2011.
Office Action of U.S. Appl. No. 11/435,497, dated Jun. 27, 2008.
Office Action of U.S. Appl. No. 11/435,497, dated Jun. 27, 2011.
Office Action of U.S. Appl. No. 11/435,497, dated Jun. 7, 2010.
Office Action of U.S. Appl. No. 11/435,497, dated Oct. 30, 2009.
Notice of Allowance and Fees Due of U.S. Appl. No. 11/435,497, dated Oct. 19, 2011.

* cited by examiner

IL-15 effects on spleen, thymus, BM

Effects of IL-15 on the thymus. Double positive cells are eliminated.

Single administration of IL-15/IL-15sRα-encoding DNA is sufficient for the complete recovery of NK cells in spleen and lung 5 days after DNA injection Ratio Of T effector / Treg after Lymphoablation

- High levels of circulating IL-15/IL-15sRα promote a transient increase in the Teffector/Treg ratio Hydrodynamic Delivery of DNA vectors expressing different forms of IL-15

Expression of CD62L On The Surface Of Spleen T Cells
After IL-15/15Ra DNA Delivery

SEQUENCE LISTING

<160> NUMBER OF SEQ ID NOS: 20

<210> SEQ ID NO 1
<211> LENGTH: 489
<212> TYPE: DNA
<213> ORGANISM: Homo sapiens
<220> FEATURE:
<223> OTHER INFORMATION: human wild-type interleukin-15 (IL-15)

<400> SEQUENCE: 1

```
atgagaattt cgaaaccaca tttgagaagt atttccatcc agtgctactt gtgtttactt      60

ctaaacagtc attttctaac tgaagctggc attcatgtct tcattttggg ctgtttcagt     120

gcagggcttc ctaaaacaga agccaactgg gtgaatgtaa taagtgattt gaaaaaaatt     180

gaagatctta ttcaatctat gcatattgat gctactttat atacggaaag tgatgttcac     240

cccagttgca aagtaacagc aatgaagtgc tttctcttgg agttacaagt tatttcactt     300

gagtctggag atgcaagtat tcatgataca gtagaaaatc tgatcatcct agcaaacaac     360

agtttgtctt ctaatgggaa tgtaacagaa tctggatgca aagaatgtga ggaactggag     420

gaaaaaaata ttaaagaatt tttgcagagt tttgtacata ttgtccaaat gttcatcaac     480

acttcttga                                                             489
```

<210> SEQ ID NO 2
<211> LENGTH: 162
<212> TYPE: PRT
<213> ORGANISM: Homo sapiens
<220> FEATURE:
<223> OTHER INFORMATION: human wild-type interleukin-15 (IL-15)

<400> SEQUENCE: 2

```
Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140
```

```
Lys Glu Phe Leu Gln Ser Phe Val His Ile Val Gln Met Phe Ile Asn
145                 150                 155                 160

Thr Ser


<210> SEQ ID NO 3
<211> LENGTH: 489
<212> TYPE: DNA
<213> ORGANISM: Artificial Sequence
<220> FEATURE:
<223> OTHER INFORMATION: synthetic improved human interleukin-15 (IL-15)
      (opt1)

<400> SEQUENCE: 3

atgcggatct cgaagccgca cctgcggtcg atatcgatcc agtgctacct gtgcctgctc     60

ctgaactcgc acttcctcac ggaggccggt atacacgtct tcatcctggg ctgcttctcg    120

gcggggctgc cgaagacgga ggcgaactgg gtgaacgtga tctcggacct gaagaagatc    180

gaggacctca tccagtcgat gcacatcgac gcgacgctgt acacggagtc ggacgtccac    240

ccgtcgtgca aggtcacggc gatgaagtgc ttcctcctgg agctccaagt catctcgctc    300

gagtcggggg acgcgtcgat ccacgacacg gtggagaacc tgatcatcct ggcgaacaac    360

tcgctgtcgt cgaacgggaa cgtcacggag tcgggctgca aggagtgcga ggagctggag    420

gagaagaaca tcaaggagtt cctgcagtcg ttcgtgcaca tcgtccagat gttcatcaac    480

acgtcgtga                                                            489


<210> SEQ ID NO 4
<211> LENGTH: 489
<212> TYPE: DNA
<213> ORGANISM: Artificial Sequence
<220> FEATURE:
<223> OTHER INFORMATION: synthetic improved human interleukin-15 (IL-15)
      (opt2)

<400> SEQUENCE: 4

atgaggatca gcaagcccca cctgaggagc atcagcatcc agtgctacct gtgcctgctg     60

ctgaacagcc acttcctgac cgaggccggt atacacgtgt tcatcctggg ctgctttagc    120

gccggactgc ccaagaccga ggccaattgg gtgaacgtga tcagcgacct gaagaagatc    180

gaggacctca tccagagcat gcacatcgac gccaccctgt acaccgagag cgatgtgcac    240

cccagctgta aggtgaccgc catgaagtgc tttctgctgg agctgcaagt gatcagcctg    300

gagagcggcg acgccagcat ccacgacacc gtggagaacc tgatcatcct ggccaacaac    360

agcctgagca gcaacggcaa tgtgaccgag agcggctgta aggagtgtga ggagctggag    420

gagaagaaca tcaaggagtt tctgcagagc ttcgtgcaca tcgtgcagat gttcatcaac    480

accagctga                                                            489


<210> SEQ ID NO 5
<211> LENGTH: 1610
<212> TYPE: DNA
<213> ORGANISM: Homo sapiens
<220> FEATURE:
<223> OTHER INFORMATION: human interleukin-15 receptor, alpha (IL15RA),
      transcript variant 1 cDNA
<220> FEATURE:
<221> NAME/KEY: CDS
<222> LOCATION: (83)..(886)
<223> OTHER INFORMATION: interleukin-15 receptor, alpha (IL15RA),
      isoform 1 precursor
```

<400> SEQUENCE: 5

```
cccagagcag cgctcgccac ctcccccccgg cctgggcagc gctcgcccgg ggagtccagc     60

ggtgtcctgt ggagctgccg ccatggcccc gcggcgggcg cgcggctgcc ggaccctcgg    120

tctcccggcg ctgctactgc tgctgctgct ccggccgccg gcgacgcggg gcatcacgtg    180

ccctcccccc atgtccgtgg aacacgcaga catctgggtc aagagctaca gcttgtactc    240

cagggagcgg tacatttgta actctggttt caagcgtaaa gccggcacgt ccagcctgac    300

ggagtgcgtg ttgaacaagg ccacgaatgt cgcccactgg acaaccccca gtctcaaatg    360

cattagagac cctgccctgg ttcaccaaag gccagcgcca ccctccacag taacgacggc    420

aggggtgacc ccacagccag agagcctctc cccttctgga aaagagcccg cagcttcatc    480

tcccagctca aacaacacag cggccacaac agcagctatt gtcccgggct cccagctgat    540

gccttcaaaa tcaccttcca caggaaccac agagataagc agtcatgagt cctcccacgg    600

cacccctct cagacaacag ccaagaactg ggaactcaca gcatccgcct cccaccagcc    660

gccaggtgtg tatccacagg gccacagcga caccactgtg gctatctcca cgtccactgt    720

cctgctgtgt gggctgagcg ctgtgtctct cctggcatgc tacctcaagt caaggcaaac    780

tcccccgctg gccagcgttg aaatggaagc catggaggct ctgccggtga cttgggggac    840

cagcagcaga gatgaagact tggaaaactg ctctcaccac ctatgaaact cggggaaacc    900

agcccagcta agtccggagt gaaggagcct ctctgcttta gctaaagacg actgagaaga    960

ggtgcaagga agcgggctcc aggagcaagc tcaccaggcc tctcagaagt cccagcagga   1020

tctcacggac tgccgggtcg gcgcctcctg cgcgagggag caggttctcc gcattcccat   1080

gggcaccacc tgcctgcctg tcgtgccttg gacccagggc ccagcttccc aggagagacc   1140

aaaggcttct gagcaggatt tttatttcat tacagtgtga gctgcctgga atacatgtgg   1200

taatgaaata aaaaccctgc cccgaatctt ccgtccctca tcctaacttt cagttcacag   1260

agaaaagtga catacccaaa gctctctgtc aattacaagg cttctcctgg cgtgggagac   1320

gtctacaggg aagacaccag cgtttgggct tctaaccacc ctgtctccag ctgctctgca   1380

cacatggaca gggacctggg aaaggtggga gagatgctga gcccagcgaa tcctctccat   1440

tgaaggattc aggaagaaga aaactcaact cagtgccatt ttacgaatat atgcgtttat   1500

atttatactt ccttgtctat tatatctata cattatatat tatttgtatt ttgacattgt   1560

accttgtata aacaaaataa aacatctatt ttcaatattt ttaaaatgca              1610
```

<210> SEQ ID NO 6
<211> LENGTH: 267
<212> TYPE: PRT
<213> ORGANISM: Homo sapiens
<220> FEATURE:
<223> OTHER INFORMATION: human interleukin-15 receptor, alpha (IL15RA), isoform 1 precursor

<400> SEQUENCE: 6

```
Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60
```

```
Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

```
<210> SEQ ID NO 7
<211> LENGTH: 1843
<212> TYPE: DNA
<213> ORGANISM: Homo sapiens
<220> FEATURE:
<223> OTHER INFORMATION: human interleukin-15 receptor, alpha (IL15RA),
      transcript variant 2 cDNA
<220> FEATURE:
<221> NAME/KEY: CDS
<222> LOCATION: (424)..(1119)
<223> OTHER INFORMATION: interleukin-15 receptor, alpha (IL15RA),
      isoform 2

<400> SEQUENCE: 7

caggaattcg gcgaagtggc ggagctgggg ccccagcggg cgccgggggc cgcgggagcc      60

agcaggtggc gggggctgcg ctccgcccgg gccagagcgc accaggcagg tgcccgcgcc     120

tccgcaccgc ggcgacacct ccgcgggcac tcacccaggc cggccgctca caaccgagcg     180

cagggccgcg gagggagacc aggaaagccg aaggcggagc agctggaggc gaccagcgcc     240

gggcgaggtc aagtggatcc gagccgcaga gagggctgga gagagtctgc tctccgatga     300

ctttgcccac tctcttcgca gtggggacac cggaccgagt gcacactgga ggtcccagag     360

cacgacgagc gcggaggacc gggaggctcc cgggcttgcg tgggcatcac gtgccctccc     420

cccatgtccg tggaacacgc agacatctgg gtcaagagct acagcttgta ctccagggag     480

cggtacattt gtaactctgg tttcaagcgt aaagccggca cgtccagcct gacggagtgc     540

gtgttgaaca aggccacgaa tgtcgcccac tggacaaccc ccagtctcaa atgcattaga     600

gaccctgccc tggttcacca aaggccagcg ccaccctcca cagtaacgac ggcaggggtg     660

accccacagc cagagagcct ctccccttct ggaaaagagc ccgcagcttc atctcccagc     720
```

```
tcaaacaaca cagcggccac aacagcagct attgtcccgg gctcccagct gatgccttca    780

aaatcacctt ccacaggaac cacagagata agcagtcatg agtcctccca cggcaccccc    840

tctcagacaa cagccaagaa ctgggaactc acagcatccg cctcccacca gccgccaggt    900

gtgtatccac agggccacag cgacaccact gtggctatct ccacgtccac tgtcctgctg    960

tgtgggctga gcgctgtgtc tctcctggca tgctacctca agtcaaggca aactcccccg   1020

ctggccagcg ttgaaatgga agccatggag gctctgccgg tgacttgggg gaccagcagc   1080

agagatgaag acttggaaaa ctgctctcac cacctatgaa actcggggaa accagcccag   1140

ctaagtccgg agtgaaggag cctctctgct ttagctaaag acgactgaga agaggtgcaa   1200

ggaagcgggc tccaggagca agctcaccag gcctctcaga agtcccagca ggatctcacg   1260

gactgccggg tcggcgcctc ctgcgcgagg gagcaggttc tccgcattcc catgggcacc   1320

acctgcctgc ctgtcgtgcc ttggacccag ggcccagctt cccaggagag accaaaggct   1380

tctgagcagg atttttattt cattacagtg tgagctgcct ggaatacatg tggtaatgaa   1440

ataaaaaccc tgccccgaat cttccgtccc tcatcctaac tttcagttca cagagaaaag   1500

tgacataccc aaagctctct gtcaattaca aggcttctcc tggcgtggga gacgtctaca   1560

gggaagacac cagcgtttgg gcttctaacc accctgtctc cagctgctct gcacacatgg   1620

acagggacct gggaaaggtg ggagagatgc tgagcccagc gaatcctctc cattgaagga   1680

ttcaggaaga agaaaactca actcagtgcc attttacgaa tatatgcgtt tatatttata   1740

cttccttgtc tattatatct atacattata tattatttgt attttgacat tgtaccttgt   1800

ataaacaaaa taaaacatct attttcaata tttttaaaat gca                     1843


<210> SEQ ID NO 8
<211> LENGTH: 231
<212> TYPE: PRT
<213> ORGANISM: Homo sapiens
<220> FEATURE:
<223> OTHER INFORMATION: human interleukin-15 receptor, alpha (IL15RA),
      isoform 2

<400> SEQUENCE: 8

Met Ser Val Glu His Ala Asp Ile Trp Val Lys Ser Tyr Ser Leu Tyr
 1               5                  10                  15

Ser Arg Glu Arg Tyr Ile Cys Asn Ser Gly Phe Lys Arg Lys Ala Gly
            20                  25                  30

Thr Ser Ser Leu Thr Glu Cys Val Leu Asn Lys Ala Thr Asn Val Ala
        35                  40                  45

His Trp Thr Thr Pro Ser Leu Lys Cys Ile Arg Asp Pro Ala Leu Val
    50                  55                  60

His Gln Arg Pro Ala Pro Pro Ser Thr Val Thr Thr Ala Gly Val Thr
65                  70                  75                  80

Pro Gln Pro Glu Ser Leu Ser Pro Ser Gly Lys Glu Pro Ala Ala Ser
                85                  90                  95

Ser Pro Ser Ser Asn Asn Thr Ala Ala Thr Thr Ala Ala Ile Val Pro
            100                 105                 110

Gly Ser Gln Leu Met Pro Ser Lys Ser Pro Ser Thr Gly Thr Thr Glu
        115                 120                 125

Ile Ser Ser His Glu Ser Ser His Gly Thr Pro Ser Gln Thr Thr Ala
    130                 135                 140

Lys Asn Trp Glu Leu Thr Ala Ser Ala Ser His Gln Pro Pro Gly Val
145                 150                 155                 160
```

```
Tyr Pro Gln Gly His Ser Asp Thr Thr Val Ala Ile Ser Thr Ser Thr
                165                 170                 175

Val Leu Leu Cys Gly Leu Ser Ala Val Ser Leu Leu Ala Cys Tyr Leu
            180                 185                 190

Lys Ser Arg Gln Thr Pro Pro Leu Ala Ser Val Glu Met Glu Ala Met
        195                 200                 205

Glu Ala Leu Pro Val Thr Trp Gly Thr Ser Ser Arg Asp Glu Asp Leu
    210                 215                 220

Glu Asn Cys Ser His His Leu
225                 230


<210> SEQ ID NO 9
<211> LENGTH: 807
<212> TYPE: DNA
<213> ORGANISM: Artificial Sequence
<220> FEATURE:
<223> OTHER INFORMATION: synthetic improved human interleukin-15 (IL-15)
      receptor alpha (IL15Ra), transcript variant 1 (OPT)

<400> SEQUENCE: 9

atggccccga ggcgggcgcg aggctgccgg accctcggtc tcccggcgct gctactgctc     60

ctgctgctcc ggccgccggc gacgcggggc atcacgtgcc cgccccccat gtccgtggag    120

cacgcagaca tctgggtcaa gagctacagc ttgtactccc gggagcggta catctgcaac    180

tcgggtttca agcggaaggc cggcacgtcc agcctgacgg agtgcgtgtt gaacaaggcc    240

acgaatgtcg cccactggac gaccccctcg ctcaagtgca tccgcgaccc ggccctggtt    300

caccagcggc ccgcgccacc ctccaccgta acgacggcgg gggtgacccc gcagccggag    360

agcctctccc cgtcgggaaa ggagcccgcc gcgtcgtcgc ccagctcgaa caacacggcg    420

gccacaactg cagcgatcgt cccgggctcc cagctgatgc cgtcgaagtc gccgtccacg    480

ggaaccacgg agatcagcag tcatgagtcc tcccacggca ccccctcgca aacgacggcc    540

aagaactggg aactcacggc gtccgcctcc caccagccgc cgggggtgta tccgcaaggc    600

cacagcgaca ccacggtggc gatctccacg tccacggtcc tgctgtgtgg gctgagcgcg    660

gtgtcgctcc tggcgtgcta cctcaagtcg aggcagactc cccgctggc cagcgttgag    720

atggaggcca tggaggctct gccggtgacg tgggggacca gcagcaggga tgaggacttg    780

gagaactgct cgcaccacct ataatga                                        807


<210> SEQ ID NO 10
<211> LENGTH: 267
<212> TYPE: PRT
<213> ORGANISM: Artificial Sequence
<220> FEATURE:
<223> OTHER INFORMATION: synthetic improved human interleukin-15 (IL-15)
      receptor alpha (IL15Ra), isoform 1 (OPT)

<400> SEQUENCE: 10

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80
```

```
Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

```
<210> SEQ ID NO 11
<211> LENGTH: 621
<212> TYPE: DNA
<213> ORGANISM: Artificial Sequence
<220> FEATURE:
<223> OTHER INFORMATION: synthetic improved human soluble interleukin-15
      (IL-15) receptor alpha (IL-15sRa) (OPT)

<400> SEQUENCE: 11

atggccccga ggcgggcgcg aggctgccgg accctcggtc tcccggcgct gctactgctc      60

ctgctgctcc ggccgccggc gacgcggggc atcacgtgcc cgcccccat gtccgtggag      120

cacgcagaca tctgggtcaa gagctacagc ttgtactccc gggagcggta catctgcaac     180

tcgggtttca agcggaaggc cggcacgtcc agcctgacgg agtgcgtgtt gaacaaggcc     240

acgaatgtcg cccactggac gaccccctcg ctcaagtgca tccgcgaccc ggccctggtt     300

caccagcggc ccgcgccacc ctccaccgta acgacggcgg gggtgacccc gcagccggag     360

agcctctccc cgtcgggaaa ggagcccgcc gcgtcgtcgc ccagctcgaa caacacggcg     420

gccacaactg cagcgatcgt cccgggctcc cagctgatgc cgtcgaagtc gccgtccacg     480

ggaaccacgg agatcagcag tcatgagtcc tcccacggca ccccctcgca aacgacggcc     540

aagaactggg aactcacggc gtccgcctcc caccagccgc cgggggtgta tccgcaaggc     600

cacagcgaca ccacgtaatg a                                               621
```

```
<210> SEQ ID NO 12
<211> LENGTH: 205
<212> TYPE: PRT
<213> ORGANISM: Artificial Sequence
<220> FEATURE:
<223> OTHER INFORMATION: synthetic improved human soluble interleukin-15
      (IL-15) receptor alpha (IL-15sRa) (OPT)
```

```
<400> SEQUENCE: 12

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205


<210> SEQ ID NO 13
<211> LENGTH: 5958
<212> TYPE: DNA
<213> ORGANISM: Artificial Sequence
<220> FEATURE:
<223> OTHER INFORMATION: synthetic dual expression plasmid vector human
      IL15Ra+IL15

<400> SEQUENCE: 13

cctggccatt gcatacgttg tatccatatc ataatatgta catttatatt ggctcatgtc      60

caacattacc gccatgttga cattgattat tgactagtta ttaatagtaa tcaattacgg     120

ggtcattagt tcatagccca tatatggagt tccgcgttac ataacttacg gtaaatggcc     180

cgcctggctg accgcccaac gacccccgcc cattgacgtc aataatgacg tatgttccca     240

tagtaacgcc aatagggact ttccattgac gtcaatgggt ggagtattta cggtaaactg     300

cccacttggc agtacatcaa gtgtatcata tgccaagtac gccccctatt gacgtcaatg     360

acggtaaatg gcccgcctgg cattatgccc agtacatgac cttatgggac tttcctactt     420

ggcagtacat ctacgtatta gtcatcgcta ttaccatggt gatgcggttt tggcagtaca     480

tcaatgggcg tggatagcgg tttgactcac ggggatttcc aagtctccac cccattgacg     540

tcaatgggag tttgttttgg caccaaaatc aacgggactt tccaaaatgt cgtaacaact     600

ccgccccatt gacgcaaatg ggcggtaggc gtgtacggtg ggaggtctat ataagcagag     660

ctcgtttagt gaaccgtcag atcgcctgga gacgccatcc acgctgtttt gacctccata     720

gaagacaccg ggaccgatcc agcctccgcg ggcgcgcgtc gaggaattcg ctagcaagaa     780

atggccccga ggcgggcgcg aggctgccgg accctcggtc tcccggcgct gctactgctc     840
```

-continued

```
ctgctgctcc ggccgccggc gacgcggggc atcacgtgcc cgccccccat gtccgtggag    900
cacgcagaca tctgggtcaa gagctacagc ttgtactccc gggagcggta catctgcaac    960
tcgggtttca agcggaaggc cggcacgtcc agcctgacgg agtgcgtgtt gaacaaggcc   1020
acgaatgtcg cccactggac gaccccctcg ctcaagtgca tccgcgaccc ggccctggtt   1080
caccagcggc ccgcgccacc ctccaccgta acgacggcgg gggtgacccc gcagccggag   1140
agcctctccc cgtcgggaaa ggagcccgcc gcgtcgtcgc ccagctcgaa caacacggcg   1200
gccacaactg cagcgatcgt cccgggctcc cagctgatgc cgtcgaagtc gccgtccacg   1260
ggaaccacgg agatcagcag tcatgagtcc tcccacggca ccccctcgca aacgacggcc   1320
aagaactggg aactcacggc gtccgcctcc caccagccgc cgggggtgta tccgcaaggc   1380
cacagcgaca ccacggtggc gatctccacg tccacggtcc tgctgtgtgg gctgagcgcg   1440
gtgtcgctcc tggcgtgcta cctcaagtcg aggcagactc cccgctggc cagcgttgag    1500
atggaggcca tggaggctct gccggtgacg tgggggacca gcagcaggga tgaggacttg   1560
gagaactgct cgcaccacct ataatgagaa ttcacgcgtg gatctgatat cggatctgct   1620
gtgccttcta gttgccagcc atctgttgtt tgcccctccc ccgtgccttc cttgaccctg   1680
gaaggtgcca ctcccactgt cctttcctaa taaaatgagg aaattgcatc gcattgtctg   1740
agtaggtgtc attctattct ggggggtggg gtggggcagg acagcaaggg ggaggattgg   1800
gaagacaata gcaggcatgc tggggatgcg gtgggctcta tgggtaccca ggtgctgaag   1860
aattgacccg gttcctcctg ggccagaaag aagcaggcac atccccttct ctgtgacaca   1920
ccctgtccac gcccctggtt cttagttcca gccccactca taggacactc atagctcagg   1980
agggctccgc cttcaatccc acccgctaaa gtacttggag cggtctctcc ctccctcatc   2040
agcccaccaa accaaaccta gcctccaaga gtgggaagaa attaaagcaa gataggctat   2100
taagtgcaga gggagagaaa atgcctccaa catgtgagga agtaatgaga gaaatcatag   2160
aatttcttcc gcttcctcgc tcactgactc gctgcgctcg gtcgttcggc tgcggcgagc   2220
ggtatcagct cactcaaagg cggtaatacg gttatccaca gaatcagggg ataacgcagg   2280
aaagaacatg tgagcaaaag gccagcaaaa ggccaggaac cgtaaaaagg ccgcgttgct   2340
ggcgtttttc cataggctcc gcccccctga cgagcatcac aaaaatcgac gctcaagtca   2400
gaggtggcga aacccgacag gactataaag ataccaggcg tttccccctg gaagctccct   2460
cgtgcgctct cctgttccga ccctgccgct taccggatac ctgtccgcct ttctcccttc   2520
gggaagcgtg gcgctttctc aatgctcacg ctgtaggtat ctcagttcgg tgtaggtcgt   2580
tcgctccaag ctgggctgtg tgcacgaacc ccccgttcag cccgaccgct gcgccttatc   2640
cggtaactat cgtcttgagt ccaacccggt aagacacgac ttatcgccac tggcagcagc   2700
cactggtaac aggattagca gagcgaggta tgtaggcggt gctacagagt tcttgaagtg   2760
gtggcctaac tacggctaca ctagaaggac agtatttggt atctgcgctc tgctgaagcc   2820
agttaccttc ggaaaaagag ttggtagctc ttgatccggc aaacaaacca ccgctggtag   2880
cggtggtttt tttgtttgca agcagcagat tacgcgcaga aaaaaaggat ctcaagaaga   2940
tcctttgatc ttttctacgg ggtctgacgc tcagtggaac gaaaactcac gttaagggat   3000
tttggtcatg agattatcaa aaaggatctt cacctagatc cttttaaatt aaaaatgaag   3060
ttttaaatca atctaaagta tatatgagta aacttggtct gacagttacc aatgcttaat   3120
cagtgaggca cctatctcag cgatctgtct atttcgttca tccatagttg cctgactcgg   3180
gggggggggg cgctgaggtc tgcctcgtga agaaggtgtt gctgactcat accaggcctg   3240
```

-continued

```
aatcgcccca tcatccagcc agaaagtgag ggagccacgg ttgatgagag ctttgttgta   3300
ggtggaccag ttggtgattt tgaacttttg ctttgccacg gaacggtctg cgttgtcggg   3360
aagatgcgtg atctgatcct tcaactcagc aaaagttcga tttattcaac aaagccgccg   3420
tcccgtcaag tcagcgtaat gctctgccag tgttacaacc aattaaccaa ttctgattag   3480
aaaaactcat cgagcatcaa atgaaactgc aatttattca tatcaggatt atcaatacca   3540
tatttttgaa aaagccgttt ctgtaatgaa ggagaaaact caccgaggca gttccatagg   3600
atggcaagat cctggtatcg gtctgcgatt ccgactcgtc caacatcaat acaacctatt   3660
aatttcccct cgtcaaaaat aaggttatca agtgagaaat caccatgagt gacgactgaa   3720
tccggtgaga atggcaaaag cttatgcatt tctttccaga cttgttcaac aggccagcca   3780
ttacgctcgt catcaaaatc actcgcatca accaaaccgt tattcattcg tgattgcgcc   3840
tgagcgagac gaaatacgcg atcgctgtta aaaggacaat tacaaacagg aatcgaatgc   3900
aaccggcgca ggaacactgc cagcgcatca acaatatttt cacctgaatc aggatattct   3960
tctaatacct ggaatgctgt tttcccgggg atcgcagtgg tgagtaacca tgcatcatca   4020
ggagtacgga taaaatgctt gatggtcgga agaggcataa attccgtcag ccagtttagt   4080
ctgaccatct catctgtaac atcattggca acgctacctt tgccatgttt cagaaacaac   4140
tctggcgcat cgggcttccc atacaatcga tagattgtcg cacctgattg cccgacatta   4200
tcgcgagccc atttataccc atataaatca gcatccatgt tggaatttaa tcgcggcctc   4260
gagcaagacg tttcccgttg aatatggctc ataacacccc ttgtattact gtttatgtaa   4320
gcagacagtt ttattgttca tgatgatata tttttatctt gtgcaatgta acatcagaga   4380
ttttgagaca caacgtggat catccagaca tgataagata cattgatgag tttggacaaa   4440
ccacaactag aatgcagtga aaaaaatgct ttatttgtga aatttgtgat gctattgctt   4500
tatttgtaac cattataagc tgcaataaac aagttaacaa caacaattgc attcatttta   4560
tgtttcaggt tcagggggag gtgtgggagg ttttttaaag caagtaaaac ctctacaaat   4620
gtggtatggc tgattatgat cgtcgaggat ctggatccgt taaccgatat ccgcgaattc   4680
ggcgcgccgg gccctcacga cgtgttgatg aacatctgga cgatgtgcac gaacgactgc   4740
aggaactcct tgatgttctt ctcctccagc tcctcgcact ccttgcagcc cgactccgtg   4800
acgttcccgt tcgacgacag cgagttgttc gccaggatga tcaggttctc caccgtgtcg   4860
tggatcgacg cgtcccccga ctcgagcgag atgacttgga gctccaggag gaagcacttc   4920
atcgccgtga ccttgcacga cgggtggacg tccgactccg tgtacagcgt cgcgtcgatg   4980
tgcatcgact ggatgaggtc ctcgatcttc ttcaggtccg agatcacgtt cacccagttc   5040
gcctccgtct tcggcagccc cgccgagaag cagcccagga tgaagacgtg tataccggcc   5100
tccgtgagga agtgcgagtt caggagcagg cacaggtagc actggatcga tatcgaccgc   5160
aggtgcggct tcgagatccg catttcttgt cgacactcga cagatccaaa cgctcctccg   5220
acgtccccag gcagaatggc ggttccctaa acgagcattg cttatataga cctcccatta   5280
ggcacgccta ccgcccattt acgtcaatgg aacgcccatt tgcgtcattg cccctcccca   5340
ttgacgtcaa tggggatgta cttggcagcc atcgcgggcc atttaccgcc attgacgtca   5400
atgggagtac tgccaatgta ccctggcgta cttccaatag taatgtactt gccaagttac   5460
tattaataga tattgatgta ctgccaagtg ggccatttac cgtcattgac gtcaataggg   5520
ggcgtgagaa cggatatgaa tgggcaatga gccatcccat tgacgtcaat ggtgggtggt   5580
cctattgacg tcaatgggca ttgagccagg cgggccattt accgtaattg acgtcaatgg   5640
```

```
gggaggcgcc atatacgtca ataggaccgc ccatatgacg tcaataggaa agaccatgag   5700

gccctttcgt ctcgcgcgtt tcggtgatga cggtgaaaac ctctgacaca tgcagctccc   5760

ggagacggtc acagcttgtc tgtaagcgga tgccgggagc agacaagccc gtcagggcgc   5820

gtcagcgggt gttggcgggt gtcggggctg gcttaactat gcggcatcag agcagattgt   5880

actgagagtg caccatatgc ggtgtgaaat accgcacaga tgcgtaagga gaaaataccg   5940

catcagattg gctattgg                                                 5958
```

<210> SEQ ID NO 14
<211> LENGTH: 5918
<212> TYPE: DNA
<213> ORGANISM: Artificial Sequence
<220> FEATURE:
<223> OTHER INFORMATION: synthetic dual expression plasmid vector human IL15Ra+IL15tPA6

<400> SEQUENCE: 14

```
cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

acggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gaggaattcg ctagcaagaa    780

atggccccga ggcgggcgcg aggctgccgg accctcggtc tcccggcgct gctactgctc    840

ctgctgctcc ggccgccggc gacgcggggc atcacgtgcc cgccccccat gtccgtggag    900

cacgcagaca tctgggtcaa gagctacagc ttgtactccc gggagcggta catctgcaac    960

tcgggtttca agcggaaggc cggcacgtcc agcctgacgg agtgcgtgtt gaacaaggcc   1020

acgaatgtcg cccactggac gacccccctcg ctcaagtgca tccgcgaccc ggccctggtt   1080

caccagcggc ccgcgccacc ctccaccgta acgacggcgg gggtgacccc gcagccggag   1140

agcctctccc cgtcgggaaa ggagcccgcc gcgtcgtcgc ccagctcgaa caacacggcg   1200

gccacaactg cagcgatcgt cccgggctcc cagctgatgc cgtcgaagtc gccgtccacg   1260

ggaaccacgg agatcagcag tcatgagtcc tcccacggca ccccctcgca aacgacggcc   1320

aagaactggg aactcacggc gtccgcctcc caccagccgc cgggggtgta tccgcaaggc   1380

cacagcgaca ccacggtggc gatctccacg tccacggtcc tgctgtgtgg gctgagcgcg   1440

gtgtcgctcc tggcgtgcta cctcaagtcg aggcagactc cccgctggc cagcgttgag   1500

atggaggcca tggaggctct gccggtgacg tgggggacca gcagcaggga tgaggacttg   1560

gagaactgct cgcaccacct ataatgagaa ttcacgcgtg gatctgatat cggatctgct   1620

gtgccttcta gttgccagcc atctgttgtt tgcccctccc ccgtgccttc cttgaccctg   1680
```

-continued

```
gaaggtgcca ctcccactgt cctttcctaa taaaatgagg aaattgcatc gcattgtctg   1740
agtaggtgtc attctattct ggggggtggg gtggggcagg acagcaaggg ggaggattgg   1800
gaagacaata gcaggcatgc tggggatgcg gtgggctcta tgggtaccca ggtgctgaag   1860
aattgacccg gttcctcctg ggccagaaag aagcaggcac atccccttct ctgtgacaca   1920
ccctgtccac gcccctggtt cttagttcca gccccactca taggacactc atagctcagg   1980
agggctccgc cttcaatccc acccgctaaa gtacttggag cggtctctcc ctccctcatc   2040
agcccaccaa accaaaccta gcctccaaga gtgggaagaa attaaagcaa gataggctat   2100
taagtgcaga gggagagaaa atgcctccaa catgtgagga agtaatgaga gaaatcatag   2160
aatttcttcc gcttcctcgc tcactgactc gctgcgctcg gtcgttcggc tgcggcgagc   2220
ggtatcagct cactcaaagg cggtaatacg gttatccaca gaatcagggg ataacgcagg   2280
aaagaacatg tgagcaaaag gccagcaaaa ggccaggaac cgtaaaaagg ccgcgttgct   2340
ggcgtttttc cataggctcc gcccccctga cgagcatcac aaaaatcgac gctcaagtca   2400
gaggtggcga aacccgacag gactataaag ataccaggcg tttccccctg gaagctccct   2460
cgtgcgctct cctgttccga ccctgccgct taccggatac ctgtccgcct ttctcccttc   2520
gggaagcgtg gcgctttctc aatgctcacg ctgtaggtat ctcagttcgg tgtaggtcgt   2580
tcgctccaag ctgggctgtg tgcacgaacc ccccgttcag cccgaccgct gcgccttatc   2640
cggtaactat cgtcttgagt ccaacccggt aagacacgac ttatcgccac tggcagcagc   2700
cactggtaac aggattagca gagcgaggta tgtaggcggt gctacagagt tcttgaagtg   2760
gtggcctaac tacggctaca ctagaaggac agtatttggt atctgcgctc tgctgaagcc   2820
agttaccttc ggaaaaagag ttggtagctc ttgatccggc aaacaaacca ccgctggtag   2880
cggtggtttt tttgtttgca agcagcagat tacgcgcaga aaaaaaggat ctcaagaaga   2940
tcctttgatc ttttctacgg ggtctgacgc tcagtggaac gaaaactcac gttaagggat   3000
tttggtcatg agattatcaa aaaggatctt cacctagatc cttttaaatt aaaaatgaag   3060
ttttaaatca atctaaagta tatatgagta aacttggtct gacagttacc aatgcttaat   3120
cagtgaggca cctatctcag cgatctgtct atttcgttca tccatagttg cctgactcgg   3180
gggggggggg cgctgaggtc tgcctcgtga agaaggtgtt gctgactcat accaggcctg   3240
aatcgcccca tcatccagcc agaaagtgag ggagccacgg ttgatgagag ctttgttgta   3300
ggtggaccag ttggtgattt tgaacttttg ctttgccacg gaacggtctg cgttgtcggg   3360
aagatgcgtg atctgatcct tcaactcagc aaaagttcga tttattcaac aaagccgccg   3420
tcccgtcaag tcagcgtaat gctctgccag tgttacaacc aattaaccaa ttctgattag   3480
aaaaactcat cgagcatcaa atgaaactgc aatttattca tatcaggatt atcaatacca   3540
tatttttgaa aaagccgttt ctgtaatgaa ggagaaaact caccgaggca gttccatagg   3600
atggcaagat cctggtatcg gtctgcgatt ccgactcgtc caacatcaat acaacctatt   3660
aatttcccct cgtcaaaaat aaggttatca agtgagaaat caccatgagt gacgactgaa   3720
tccggtgaga atggcaaaag cttatgcatt tctttccaga cttgttcaac aggccagcca   3780
ttacgctcgt catcaaaatc actcgcatca accaaaccgt tattcattcg tgattgcgcc   3840
tgagcgagac gaaatacgcg atcgctgtta aaaggacaat tacaaacagg aatcgaatgc   3900
aaccggcgca ggaacactgc cagcgcatca acaatatttt cacctgaatc aggatattct   3960
tctaatacct ggaatgctgt tttcccgggg atcgcagtgg tgagtaacca tgcatcatca   4020
ggagtacgga taaaatgctt gatggtcgga agaggcataa attccgtcag ccagtttagt   4080
```

```
ctgaccatct catctgtaac atcattggca acgctacctt tgccatgttt cagaaacaac   4140
tctggcgcat cgggcttccc atacaatcga tagattgtcg cacctgattg cccgacatta   4200
tcgcgagccc atttataccc atataaatca gcatccatgt tggaatttaa tcgcggcctc   4260
gagcaagacg tttcccgttg aatatggctc ataacacccc ttgtattact gtttatgtaa   4320
gcagacagtt ttattgttca tgatgatata tttttatctt gtgcaatgta acatcagaga   4380
ttttgagaca caacgtggat catccagaca tgataagata cattgatgag tttggacaaa   4440
ccacaactag aatgcagtga aaaaaatgct ttatttgtga aatttgtgat gctattgctt   4500
tatttgtaac cattataagc tgcaataaac aagttaacaa caacaattgc attcatttta   4560
tgtttcaggt tcagggggag gtgtgggagg ttttttaaag caagtaaaac ctctacaaat   4620
gtggtatggc tgattatgat cgtcgaggat ctggatctgg atccgttaac cgatatccgc   4680
gaattcggcg cgccgggccc tcacgacgtg ttgatgaaca tctggacgat gtgcacgaac   4740
gactgcagga actccttgat gttcttctcc tccagctcct cgcactcctt gcagcccgac   4800
tccgtgacgt tcccgttcga cgacagcgag ttgttcgcca ggatgatcag gttctccacc   4860
gtgtcgtgga tcgacgcgtc cccgactcg agcgagatga cttggagctc caggaggaag   4920
cacttcatcg ccgtgacctt gcacgacggg tggacgtccg actccgtgta cagcgtcgcg   4980
tcgatgtgca tcgactggat gaggtcctcg atcttcttca ggtccgagat cacgttcacc   5040
cagtttctgg ctcctcttct gaatcgggca tggatttcct ggctgggcga aacgaagact   5100
gctccacaca gcagcagcac acagcagagc cctctcttca ttgcatccat ttcttgtcga   5160
cagatccaaa cgctcctccg acgtccccag gcagaatggc ggttccctaa acgagcattg   5220
cttatataga cctcccatta ggcacgccta ccgcccattt acgtcaatgg aacgcccatt   5280
tgcgtcattg cccctcccca ttgacgtcaa tggggatgta cttggcagcc atcgcgggcc   5340
atttaccgcc attgacgtca atgggagtac tgccaatgta ccctggcgta cttccaatag   5400
taatgtactt gccaagttac tattaataga tattgatgta ctgccaagtg ggccatttac   5460
cgtcattgac gtcaataggg ggcgtgagaa cggatatgaa tgggcaatga gccatcccat   5520
tgacgtcaat ggtgggtggt cctattgacg tcaatgggca ttgagccagg cgggccattt   5580
accgtaattg acgtcaatgg gggaggcgcc atatacgtca ataggaccgc ccatatgacg   5640
tcaataggaa agaccatgag gccctttcgt ctcgcgcgtt tcggtgatga cggtgaaaac   5700
ctctgacaca tgcagctccc ggagacggtc acagcttgtc tgtaagcgga tgccgggagc   5760
agacaagccc gtcagggcgc gtcagcgggt gttggcgggt gtcggggctg gcttaactat   5820
gcggcatcag agcagattgt actgagagtg caccatatgc ggtgtgaaat accgcacaga   5880
tgcgtaagga gaaaataccg catcagattg gctattgg                          5918
```

```
<210> SEQ ID NO 15
<211> LENGTH: 5736
<212> TYPE: DNA
<213> ORGANISM: Artificial Sequence
<220> FEATURE:
<223> OTHER INFORMATION: synthetic dual expression plasmid vector human
      IL15sRa(soluble)+IL15tPA6

<400> SEQUENCE: 15
```

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
```

-continued

```
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gaggaattcg ctagcaagaa    780
atggccccga ggcgggcgcg aggctgccgg accctcggtc tcccggcgct gctactgctc    840
ctgctgctcc ggccgccggc gacgcggggc atcacgtgcc cgccccccat gtccgtggag    900
cacgcagaca tctgggtcaa gagctacagc ttgtactccc gggagcggta catctgcaac    960
tcgggtttca agcggaaggc cggcacgtcc agcctgacgg agtgcgtgtt gaacaaggcc   1020
acgaatgtcg cccactggac gacccccctcg ctcaagtgca tccgcgaccc ggccctggtt   1080
caccagcggc ccgcgccacc ctccaccgta acgacggcgg gggtgacccc gcagccggag   1140
agcctctccc cgtcgggaaa ggagcccgcc gcgtcgtcgc ccagctcgaa caacacggcg   1200
gccacaactg cagcgatcgt cccgggctcc cagctgatgc cgtcgaagtc gccgtccacg   1260
ggaaccacgg agatcagcag tcatgagtcc tcccacggca ccccctcgca aacgacggcc   1320
aagaactggg aactcacggc gtccgcctcc caccagccgc cgggggtgta tccgcaaggc   1380
cacagcgaca ccacgtaatg agaattcgcg gatatcggtt aacggatcca gatctgctgt   1440
gccttctagt tgccagccat ctgttgtttg cccctccccc gtgccttcct tgaccctgga   1500
aggtgccact cccactgtcc tttcctaata aaatgaggaa attgcatcgc attgtctgag   1560
taggtgtcat tctattctgg ggggtggggt ggggcaggac agcaaggggg aggattggga   1620
agacaatagc aggcatgctg gggatgcggt gggctctatg ggtacccagg tgctgaagaa   1680
ttgacccggt tcctcctggg ccagaaagaa gcaggcacat ccccttctct gtgacacacc   1740
ctgtccacgc ccctggttct tagttccagc cccactcata ggacactcat agctcaggag   1800
ggctccgcct tcaatcccac ccgctaaagt acttggagcg gtctctccct ccctcatcag   1860
cccaccaaac caaacctagc ctccaagagt gggaagaaat taaagcaaga taggctatta   1920
agtgcagagg gagagaaaat gcctccaaca tgtgaggaag taatgagaga aatcatagaa   1980
tttcttccgc ttcctcgctc actgactcgc tgcgctcggt cgttcggctg cggcgagcgg   2040
tatcagctca ctcaaaggcg gtaatacggt tatccacaga atcaggggat aacgcaggaa   2100
agaacatgtg agcaaaaggc cagcaaaagg ccaggaaccg taaaaaggcc gcgttgctgg   2160
cgtttttcca taggctccgc ccccctgacg agcatcacaa aaatcgacgc tcaagtcaga   2220
ggtggcgaaa cccgacagga ctataaagat accaggcgtt tccccctgga agctccctcg   2280
tgcgctctcc tgttccgacc ctgccgctta ccggatacct gtccgccttt ctcccttcgg   2340
gaagcgtggc gctttctcaa tgctcacgct gtaggtatct cagttcggtg taggtcgttc   2400
gctccaagct gggctgtgtg cacgaacccc ccgttcagcc cgaccgctgc gccttatccg   2460
gtaactatcg tcttgagtcc aacccggtaa gacacgactt atcgccactg gcagcagcca   2520
ctggtaacag gattagcaga gcgaggtatg taggcggtgc tacagagttc ttgaagtggt   2580
```

```
ggcctaacta cggctacact agaaggacag tatttggtat ctgcgctctg ctgaagccag   2640
ttaccttcgg aaaaagagtt ggtagctctt gatccggcaa acaaaccacc gctggtagcg   2700
gtggtttttt tgtttgcaag cagcagatta cgcgcagaaa aaaaggatct caagaagatc   2760
ctttgatctt ttctacgggg tctgacgctc agtggaacga aaactcacgt taagggattt   2820
tggtcatgag attatcaaaa aggatcttca cctagatcct tttaaattaa aaatgaagtt   2880
ttaaatcaat ctaaagtata tatgagtaaa cttggtctga cagttaccaa tgcttaatca   2940
gtgaggcacc tatctcagcg atctgtctat ttcgttcatc catagttgcc tgactcgggg   3000
ggggggggcg ctgaggtctg cctcgtgaag aaggtgttgc tgactcatac caggcctgaa   3060
tcgccccatc atccagccag aaagtgaggg agccacggtt gatgagagct ttgttgtagg   3120
tggaccagtt ggtgattttg aacttttgct ttgccacgga acggtctgcg ttgtcgggaa   3180
gatgcgtgat ctgatccttc aactcagcaa aagttcgatt tattcaacaa agccgccgtc   3240
ccgtcaagtc agcgtaatgc tctgccagtg ttacaaccaa ttaaccaatt ctgattagaa   3300
aaactcatcg agcatcaaat gaaactgcaa tttattcata tcaggattat caataccata   3360
tttttgaaaa agccgtttct gtaatgaagg agaaaactca ccgaggcagt tccataggat   3420
ggcaagatcc tggtatcggt ctgcgattcc gactcgtcca acatcaatac aacctattaa   3480
tttcccctcg tcaaaaataa ggttatcaag tgagaaatca ccatgagtga cgactgaatc   3540
cggtgagaat ggcaaaagct tatgcatttc tttccagact tgttcaacag gccagccatt   3600
acgctcgtca tcaaaatcac tcgcatcaac caaaccgtta ttcattcgtg attgcgcctg   3660
agcgagacga aatacgcgat cgctgttaaa aggacaatta caaacaggaa tcgaatgcaa   3720
ccggcgcagg aacactgcca gcgcatcaac aatattttca cctgaatcag gatattcttc   3780
taatacctgg aatgctgttt tcccggggat cgcagtggtg agtaaccatg catcatcagg   3840
agtacggata aaatgcttga tggtcggaag aggcataaat tccgtcagcc agtttagtct   3900
gaccatctca tctgtaacat cattggcaac gctacctttg ccatgtttca gaaacaactc   3960
tggcgcatcg ggcttcccat acaatcgata gattgtcgca cctgattgcc cgacattatc   4020
gcgagcccat ttatacccat ataaatcagc atccatgttg gaatttaatc gcggcctcga   4080
gcaagacgtt tcccgttgaa tatggctcat aacacccctt gtattactgt ttatgtaagc   4140
agacagtttt attgttcatg atgatatatt tttatcttgt gcaatgtaac atcagagatt   4200
ttgagacaca acgtggatca tccagacatg ataagataca ttgatgagtt tggacaaacc   4260
acaactagaa tgcagtgaaa aaaatgcttt atttgtgaaa tttgtgatgc tattgcttta   4320
tttgtaacca ttataagctg caataaacaa gttaacaaca acaattgcat tcattttatg   4380
tttcaggttc agggggaggt gtgggaggtt ttttaaagca agtaaaacct ctacaaatgt   4440
ggtatggctg attatgatcg tcgaggatct ggatctggat ccgttaaccg atatccgcga   4500
attcggcgcg ccgggccctc acgacgtgtt gatgaacatc tggacgatgt gcacgaacga   4560
ctgcaggaac tccttgatgt tcttctcctc cagctcctcg cactccttgc agcccgactc   4620
cgtgacgttc ccgttcgacg acagcgagtt gttcgccagg atgatcaggt tctccaccgt   4680
gtcgtggatc gacgcgtccc ccgactcgag cgagatgact tggagctcca ggaggaagca   4740
cttcatcgcc gtgaccttgc acgacgggtg gacgtccgac tccgtgtaca gcgtcgcgtc   4800
gatgtgcatc gactggatga ggtcctcgat cttcttcagg tccgagatca cgttcaccca   4860
gtttctggct cctcttctga atcgggcatg gatttcctgg ctgggcgaaa cgaagactgc   4920
tccacacagc agcagcacac agcagagccc tctcttcatt gcatccattt cttgtcgaca   4980
```

```
gatccaaacg ctcctccgac gtccccaggc agaatggcgg ttccctaaac gagcattgct   5040

tatatagacc tcccattagg cacgcctacc gcccatttac gtcaatggaa cgcccatttg   5100

cgtcattgcc cctccccatt gacgtcaatg gggatgtact tggcagccat cgcgggccat   5160

ttaccgccat tgacgtcaat gggagtactg ccaatgtacc ctggcgtact tccaatagta   5220

atgtacttgc caagttacta ttaatagata ttgatgtact gccaagtggg ccatttaccg   5280

tcattgacgt caataggggg cgtgagaacg gatatgaatg ggcaatgagc catcccattg   5340

acgtcaatgg tgggtggtcc tattgacgtc aatgggcatt gagccaggcg ggccatttac   5400

cgtaattgac gtcaatgggg gaggcgccat atacgtcaat aggaccgccc atatgacgtc   5460

aataggaaag accatgaggc cctttcgtct cgcgcgtttc ggtgatgacg gtgaaaacct   5520

ctgacacatg cagctcccgg agacggtcac agcttgtctg taagcggatg ccgggagcag   5580

acaagcccgt cagggcgcgt cagcgggtgt tggcgggtgt cggggctggc ttaactatgc   5640

ggcatcagag cagattgtac tgagagtgca ccatatgcgg tgtgaaatac cgcacagatg   5700

cgtaaggaga aaataccgca tcagattggc tattgg                             5736


<210> SEQ ID NO 16
<211> LENGTH: 6369
<212> TYPE: DNA
<213> ORGANISM: Artificial Sequence
<220> FEATURE:
<223> OTHER INFORMATION: synthetic sIL-15Ralpha-Fc fusion protein
      plasmid vector DPhuIL15sRa205FC+huGMIL15

<400> SEQUENCE: 16

cctggccatt gcatacgttg tatccatatc ataatatgta catttatatt ggctcatgtc     60

caacattacc gccatgttga cattgattat tgactagtta ttaatagtaa tcaattacgg    120

ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

atggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacgctagca agaaatggcc    780

ccgaggcggg cgcgaggctg ccggaccctc ggtctcccgg cgctgctact gctcctgctg    840

ctccggccgc cggcgacgcg gggcatcacg tgcccgcccc ccatgtccgt ggagcacgca    900

gacatctggg tcaagagcta cagcttgtac tcccgggagc ggtacatctg caactcgggt    960

ttcaagcgga aggccggcac gtccagcctg acggagtgcg tgttgaacaa ggccacgaat   1020

gtcgcccact ggacgacccc ctcgctcaag tgcatccgcg acccggccct ggttcaccag   1080

cggcccgcgc caccctccac cgtaacgacg gcgggggtga ccccgcagcc ggagagcctc   1140

tccccgtcgg gaaaggagcc cgccgcgtcg tcgcccagct cgaacaacac ggcggccaca   1200

actgcagcga tcgtcccggg ctcccagctg atgccgtcga agtcgccgtc cacgggaacc   1260
```

-continued

```
acggagatca gcagtcatga gtcctcccac ggcacccccct cgcaaacgac ggccaagaac   1320
tgggaactca cggcgtccgc ctcccaccag ccgccggggg tgtatccgca aggccacagc   1380
gacaccacgc cgaagtcctg cgacaagacg cacacgtgcc ctccctgccc ggcgcccgag   1440
ctgctgggag gtccgagcgt gttcctcttc ccgcccaagc cgaaggacac gctcatgatc   1500
tcgcggactc ccgaggtcac ctgcgtcgtg gtagacgtca gccacgagga cccggaggtc   1560
aagttcaact ggtacgttga cggcgtagag gtgcacaacg cgaagacgaa gccgcgggag   1620
gagcagtaca actcgacgta ccgagtcgtg tcggtcctga ccgtcctgca ccaggactgg   1680
ctcaacggga aggagtacaa gtgcaaggtg tcgaacaagg cgctccctgc cccgatcgag   1740
aagacgatct cgaaggcgaa gggccagccc agggagcccc aggtctacac gctcccgcca   1800
tcgcgggacg agctgacgaa gaaccaggtt tccctgacgt gcctcgtcaa gggcttctac   1860
ccatcggaca tcgcggtgga gtgggagagc aacgggcagc cggagaacaa ctacaagacc   1920
acgcctccgg tgctcgactc ggacgggtcg ttcttcctct actcgaagct gaccgtcgac   1980
aagagccggt ggcagcaggg caacgtgttc tcctgctcgg tgatgcacga ggccctccac   2040
aaccactaca cccagaagtc gctcagtctg agcccgggga agtaatgagg atccgaattc   2100
gcggatatcg gttaacggat ccagatctgc tgtgccttct agttgccagc catctgttgt   2160
ttgcccctcc cccgtgcctt ccttgaccct ggaaggtgcc actcccactg tcctttccta   2220
ataaaatgag gaaattgcat cgcattgtct gagtaggtgt cattctattc tggggggtgg   2280
ggtggggcag gacagcaagg gggaggattg ggaagacaat agcaggcatg ctggggatgc   2340
ggtgggctct atgggtaccc aggtgctgaa gaattgaccc ggttcctcct gggccagaaa   2400
gaagcaggca catccccttc tctgtgacac accctgtcca cgcccctggt tcttagttcc   2460
agccccactc ataggacact catagctcag gagggctccg ccttcaatcc cacccgctaa   2520
agtacttgga gcggtctctc cctccctcat cagcccacca aaccaaacct agcctccaag   2580
agtgggaaga aattaaagca agataggcta ttaagtgcag agggagagaa aatgcctcca   2640
acatgtgagg aagtaatgag agaaatcata gaatttcttc cgcttcctcg ctcactgact   2700
cgctgcgctc ggtcgttcgg ctgcggcgag cggtatcagc tcactcaaag gcggtaatac   2760
ggttatccac agaatcaggg gataacgcag gaaagaacat gtgagcaaaa ggccagcaaa   2820
aggccaggaa ccgtaaaaag gccgcgttgc tggcgttttt ccataggctc cgcccccctg   2880
acgagcatca caaaaatcga cgctcaagtc agaggtggcg aaacccgaca ggactataaa   2940
gataccaggc gtttccccct ggaagctccc tcgtgcgctc tcctgttccg accctgccgc   3000
ttaccggata cctgtccgcc tttctccctt cgggaagcgt ggcgctttct catagctcac   3060
gctgtaggta tctcagttcg gtgtaggtcg ttcgctccaa gctgggctgt gtgcacgaac   3120
cccccgttca gcccgaccgc tgcgccttat ccggtaacta tcgtcttgag tccaacccgg   3180
taagacacga cttatcgcca ctggcagcag ccactggtaa caggattagc agagcgaggt   3240
atgtaggcgg tgctacagag ttcttgaagt ggtggcctaa ctacggctac actagaagaa   3300
cagtatttgg tatctgcgct ctgctgaagc cagttacctt cggaaaaaga gttggtagct   3360
cttgatccgg caaacaaacc accgctggta gcggtggttt ttttgtttgc aagcagcaga   3420
ttacgcgcag aaaaaaagga tctcaagaag atcctttgat cttttctacg gggtctgacg   3480
ctcagtggaa cgaaaactca cgttaaggga ttttggtcat gagattatca aaaaggatct   3540
tcacctagat ccttttaaat taaaaatgaa gttttaaatc aatctaaagt atatatgagt   3600
aaacttggtc tgacagttac caatgcttaa tcagtgaggc acctatctca gcgatctgtc   3660
```

```
tatttcgttc atccatagtt gcctgactcg gggggggggg gcgctgaggt ctgcctcgtg   3720
aagaaggtgt tgctgactca taccaggcct gaatcgcccc atcatccagc cagaaagtga   3780
gggagccacg gttgatgaga gctttgttgt aggtggacca gttggtgatt ttgaactttt   3840
gctttgccac ggaacggtct gcgttgtcgg gaagatgcgt gatctgatcc ttcaactcag   3900
caaaagttcg atttattcaa caaagccgcc gtcccgtcaa gtcagcgtaa tgctctgcca   3960
gtgttacaac caattaacca attctgatta gaaaaactca tcgagcatca aatgaaactg   4020
caatttattc atatcaggat tatcaatacc atatttttga aaaagccgtt tctgtaatga   4080
aggagaaaac tcaccgaggc agttccatag gatggcaaga tcctggtatc ggtctgcgat   4140
tccgactcgt ccaacatcaa tacaacctat taatttcccc tcgtcaaaaa taaggttatc   4200
aagtgagaaa tcaccatgag tgacgactga atccggtgag aatggcaaaa gcttatgcat   4260
ttctttccag acttgttcaa caggccagcc attacgctcg tcatcaaaat cactcgcatc   4320
aaccaaaccg ttattcattc gtgattgcgc ctgagcgaga cgaaatacgc gatcgctgtt   4380
aaaaggacaa ttacaaacag gaatcgaatg caaccggcgc aggaacactg ccagcgcatc   4440
aacaatattt tcacctgaat caggatattc ttctaatacc tggaatgctg ttttcccggg   4500
gatcgcagtg gtgagtaacc atgcatcatc aggagtacgg ataaaatgct tgatggtcgg   4560
aagaggcata aattccgtca gccagtttag tctgaccatc tcatctgtaa catcattggc   4620
aacgctacct ttgccatgtt tcagaaacaa ctctggcgca tcgggcttcc catacaatcg   4680
atagattgtc gcacctgatt gcccgacatt atcgcgagcc catttatacc catataaatc   4740
agcatccatg ttggaattta atcgcggcct cgagcaagac gtttcccgtt gaatatggct   4800
cataacaccc cttgtattac tgtttatgta agcagacagt tttattgttc atgatgatat   4860
atttttatct tgtgcaatgt aacatcagag attttgagac acaacgtgga tcatccagac   4920
atgataagat acattgatga gtttggacaa accacaacta gaatgcagtg aaaaaaatgc   4980
tttatttgtg aaatttgtga tgctattgct ttatttgtaa ccattataag ctgcaataaa   5040
caagttaaca acaacaattg cattcatttt atgtttcagg ttcaggggga ggtgtgggag   5100
gtttttaaa  gcaagtaaaa cctctacaaa tgtggtatgg ctgattatga tcgtcgagga   5160
tctggatccg ttaaccgata tccgcgaatt cggcgcgccg ggccctcacg acgtgttgat   5220
gaacatctgg acgatgtgca cgaacgactg caggaactcc ttgatgttct tctcctccag   5280
ctcctcgcac tccttgcagc ccgactccgt gacgttcccg ttcgacgaca gcgagttgtt   5340
cgccaggatg atcaggttct ccaccgtgtc gtggatcgac gcgtcccccg actcgagcga   5400
gatgacttgg agctccagga ggaagcactt catcgccgtg accttgcacg acgggtggac   5460
gtccgactcc gtgtacagcg tcgcgtcgat gtgcatcgac tggatgaggt cctcgatctt   5520
cttcaggtcc gagatcacgt tcacccagtt cgagatgctg caggccaccg tccccaggag   5580
tagcaggctc tggagccaca tttcttgtcg acagatccaa acgctcctcc gacgtcccca   5640
ggcagaatgg cggttcccta aacgagcatt gcttatatag acctcccatt aggcacgcct   5700
accgcccatt tacgtcaatg gaacgcccat ttgcgtcatt gcccctcccc attgacgtca   5760
atggggatgt acttggcagc catcgcgggc catttaccgc cattgacgtc aatgggagta   5820
ctgccaatgt accctggcgt acttccaata gtaatgtact tgccaagtta ctattaatag   5880
atattgatgt actgccaagt gggccattta ccgtcattga cgtcaatagg gggcgtgaga   5940
acggatatga atgggcaatg agccatccca ttgacgtcaa tggtgggtgg tcctattgac   6000
gtcaatgggc attgagccag gcgggccatt taccgtaatt gacgtcaatg ggggaggcgc   6060
```

```
catatacgtc aataggaccg cccatatgac gtcaataggt aagaccatga ggccctttcg   6120

tctcgcgcgt ttcggtgatg acggtgaaaa cctctgacac atgcagctcc cggagacggt   6180

cacagcttgt ctgtaagcgg atgccgggag cagacaagcc cgtcagggcg cgtcagcggg   6240

tgttggcggg tgtcggggct ggcttaacta tgcggcatca gagcagattg tactgagagt   6300

gcaccatatg cggtgtgaaa taccgcacag atgcgtaagg agaaaatacc gcatcagatt   6360

ggctattgg                                                           6369


<210> SEQ ID NO 17
<211> LENGTH: 436
<212> TYPE: PRT
<213> ORGANISM: Artificial Sequence
<220> FEATURE:
<223> OTHER INFORMATION: synthetic sIL-15Ralpha-Fc fusion protein
      huIL15sRa205-Fc

<400> SEQUENCE: 17

Met Ala Pro Arg Arg Ala Arg Gly Cys Arg Thr Leu Gly Leu Pro Ala
 1               5                  10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Pro Lys Ser
        195                 200                 205

Cys Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300
```

```
Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Asp Glu Leu Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys
        435


<210> SEQ ID NO 18
<211> LENGTH: 131
<212> TYPE: PRT
<213> ORGANISM: Artificial Sequence
<220> FEATURE:
<223> OTHER INFORMATION: synthetic human GMCSF-IL15 fusion protein
      huGMCSF-IL15

<400> SEQUENCE: 18

Met Trp Leu Gln Ser Leu Leu Leu Leu Gly Thr Val Ala Cys Ser Ile
 1               5                  10                  15

Ser Asn Trp Val Asn Val Ile Ser Asp Leu Lys Lys Ile Glu Asp Leu
            20                  25                  30

Ile Gln Ser Met His Ile Asp Ala Thr Leu Tyr Thr Glu Ser Asp Val
        35                  40                  45

His Pro Ser Cys Lys Val Thr Ala Met Lys Cys Phe Leu Leu Glu Leu
    50                  55                  60

Gln Val Ile Ser Leu Glu Ser Gly Asp Ala Ser Ile His Asp Thr Val
65                  70                  75                  80

Glu Asn Leu Ile Ile Leu Ala Asn Asn Ser Leu Ser Ser Asn Gly Asn
                85                  90                  95

Val Thr Glu Ser Gly Cys Lys Glu Cys Glu Glu Leu Glu Glu Lys Asn
            100                 105                 110

Ile Lys Glu Phe Leu Gln Ser Phe Val His Ile Val Gln Met Phe Ile
        115                 120                 125

Asn Thr Ser
    130


<210> SEQ ID NO 19
<211> LENGTH: 6354
<212> TYPE: DNA
<213> ORGANISM: Artificial Sequence
<220> FEATURE:
<223> OTHER INFORMATION: synthetic IL-15Ralpha-Fc fusion protein plasmid
      vector AG256DPhuIL15sRA200FC+huGMIL15

<400> SEQUENCE: 19

cctggccatt gcatacgttg tatccatatc ataatatgta catttatatt ggctcatgtc      60

caacattacc gccatgttga cattgattat tgactagtta ttaatagtaa tcaattacgg     120
```

```
ggtcattagt tcatagccca tatatggagt tccgcgttac ataacttacg gtaaatggcc    180

cgcctggctg accgcccaac gacccccgcc cattgacgtc aataatgacg tatgttccca    240

tagtaacgcc aatagggact ttccattgac gtcaatgggt ggagtattta cggtaaactg    300

cccacttggc agtacatcaa gtgtatcata tgccaagtac gccccctatt gacgtcaatg    360

atggtaaatg gcccgcctgg cattatgccc agtacatgac cttatgggac tttcctactt    420

ggcagtacat ctacgtatta gtcatcgcta ttaccatggt gatgcggttt tggcagtaca    480

tcaatgggcg tggatagcgg tttgactcac ggggatttcc aagtctccac cccattgacg    540

tcaatgggag tttgttttgg caccaaaatc aacgggactt tccaaaatgt cgtaacaact    600

ccgccccatt gacgcaaatg ggcggtaggc gtgtacggtg ggaggtctat ataagcagag    660

ctcgtttagt gaaccgtcag atcgcctgga gacgccatcc acgctgtttt gacctccata    720

gaagacaccg ggaccgatcc agcctccgcg ggcgcgcgtc gacgctagca agaaatggcc    780

ccgaggcggg cgcgaggctg ccggaccctc ggtctcccgg cgctgctact gctcctgctg    840

ctccggccgc cggcgacgcg ggcatcacg tgcccgcccc ccatgtccgt ggagcacgca    900

gacatctggg tcaagagcta cagcttgtac tcccgggagc ggtacatctg caactcgggt    960

ttcaagcgga aggccggcac gtccagcctg acggagtgcg tgttgaacaa ggccacgaat   1020

gtcgcccact ggacgacccc ctcgctcaag tgcatccgcg acccggccct ggttcaccag   1080

cggcccgcgc caccctccac cgtaacgacg gcgggggtga ccccgcagcc ggagagcctc   1140

tccccgtcgg gaaaggagcc cgccgcgtcg tcgcccagct cgaacaacac ggcggccaca   1200

actgcagcga tcgtcccggg ctcccagctg atgccgtcga agtcgccgtc cacgggaacc   1260

acggagatca gcagtcatga gtcctcccac ggcacccccct cgcaaacgac ggccaagaac   1320

tgggaactca cggcgtccgc ctcccaccag ccgccggggg tgtatccgca aggcccgaag   1380

tcctgcgaca agacgcacac gtgccctccc tgcccggcgc ccgagctgct gggaggtccg   1440

agcgtgttcc tcttcccgcc caagccgaag gacacgctca tgatctcgcg gactcccgag   1500

gtcacctgcg tcgtggtaga cgtcagccac gaggacccgg aggtcaagtt caactggtac   1560

gttgacggcg tagaggtgca caacgcgaag acgaagccgc gggaggagca gtacaactcg   1620

acgtaccgag tcgtgtcggt cctgaccgtc ctgcaccagg actggctcaa cgggaaggag   1680

tacaagtgca aggtgtcgaa caaggcgctc cctgccccga tcgagaagac gatctcgaag   1740

gcgaagggcc agcccaggga gccccaggtc tacacgctcc cgccatcgcg ggacgagctg   1800

acgaagaacc aggtttccct gacgtgcctc gtcaagggct tctacccatc ggacatcgcg   1860

gtggagtggg agagcaacgg gcagccggag aacaactaca agaccacgcc tccggtgctc   1920

gactcggacg ggtcgttctt cctctactcg aagctgaccg tcgacaagag ccggtggcag   1980

cagggcaacg tgttctcctg ctcggtgatg cacgaggccc tccacaacca ctacacccag   2040

aagtcgctca gtctgagccc ggggaagtaa tgaggatccg aattcgcgga tatcggttaa   2100

cggatccaga tctgctgtgc cttctagttg ccagccatct gttgtttgcc cctcccccgt   2160

gccttccttg accctggaag gtgccactcc cactgtcctt tcctaataaa atgaggaaat   2220

tgcatcgcat tgtctgagta ggtgtcattc tattctgggg ggtggggtgg ggcaggacag   2280

caagggggag gattgggaag acaatagcag gcatgctggg gatgcggtgg gctctatggg   2340

tacccaggtg ctgaagaatt gacccggttc ctcctgggcc agaaagaagc aggcacatcc   2400

ccttctctgt gacacaccct gtccacgccc ctggttctta gttccagccc cactcatagg   2460

acactcatag ctcaggaggg ctccgccttc aatcccaccc gctaaagtac ttggagcggt   2520
```

```
ctctccctcc ctcatcagcc caccaaacca aacctagcct ccaagagtgg gaagaaatta   2580
aagcaagata ggctattaag tgcagaggga gagaaaatgc ctccaacatg tgaggaagta   2640
atgagagaaa tcatagaatt tcttccgctt cctcgctcac tgactcgctg cgctcggtcg   2700
ttcggctgcg gcgagcggta tcagctcact caaaggcggt aatacggtta tccacagaat   2760
caggggataa cgcaggaaag aacatgtgag caaaaggcca gcaaaaggcc aggaaccgta   2820
aaaaggccgc gttgctggcg tttttccata ggctccgccc ccctgacgag catcacaaaa   2880
atcgacgctc aagtcagagg tggcgaaacc cgacaggact ataaagatac caggcgtttc   2940
cccctggaag ctccctcgtg cgctctcctg ttccgaccct gccgcttacc ggatacctgt   3000
ccgcctttct cccttcggga agcgtggcgc tttctcatag ctcacgctgt aggtatctca   3060
gttcggtgta ggtcgttcgc tccaagctgg gctgtgtgca cgaacccccc gttcagcccg   3120
accgctgcgc cttatccggt aactatcgtc ttgagtccaa cccggtaaga cacgacttat   3180
cgccactggc agcagccact ggtaacagga ttagcagagc gaggtatgta ggcggtgcta   3240
cagagttctt gaagtggtgg cctaactacg gctacactag aagaacagta tttggtatct   3300
gcgctctgct gaagccagtt accttcggaa aaagagttgg tagctcttga tccggcaaac   3360
aaaccaccgc tggtagcggt ggtttttttg tttgcaagca gcagattacg cgcagaaaaa   3420
aaggatctca agaagatcct ttgatctttt ctacggggtc tgacgctcag tggaacgaaa   3480
actcacgtta agggattttg gtcatgagat tatcaaaaag gatcttcacc tagatccttt   3540
taaattaaaa atgaagtttt aaatcaatct aaagtatata tgagtaaact tggtctgaca   3600
gttaccaatg cttaatcagt gaggcaccta tctcagcgat ctgtctattt cgttcatcca   3660
tagttgcctg actcgggggg ggggggcgct gaggtctgcc tcgtgaagaa ggtgttgctg   3720
actcatacca ggcctgaatc gccccatcat ccagccagaa agtgagggag ccacggttga   3780
tgagagcttt gttgtaggtg gaccagttgg tgattttgaa cttttgcttt gccacggaac   3840
ggtctgcgtt gtcgggaaga tgcgtgatct gatccttcaa ctcagcaaaa gttcgattta   3900
ttcaacaaag ccgccgtccc gtcaagtcag cgtaatgctc tgccagtgtt acaaccaatt   3960
aaccaattct gattagaaaa actcatcgag catcaaatga aactgcaatt tattcatatc   4020
aggattatca ataccatatt tttgaaaaag ccgtttctgt aatgaaggag aaaactcacc   4080
gaggcagttc cataggatgg caagatcctg gtatcggtct gcgattccga ctcgtccaac   4140
atcaatacaa cctattaatt tcccctcgtc aaaaataagg ttatcaagtg agaaatcacc   4200
atgagtgacg actgaatccg gtgagaatgg caaaagctta tgcatttctt tccagacttg   4260
ttcaacaggc cagccattac gctcgtcatc aaaatcactc gcatcaacca aaccgttatt   4320
cattcgtgat tgcgcctgag cgagacgaaa tacgcgatcg ctgttaaaag gacaattaca   4380
aacaggaatc gaatgcaacc ggcgcaggaa cactgccagc gcatcaacaa tattttcacc   4440
tgaatcagga tattcttcta atacctggaa tgctgttttc ccggggatcg cagtggtgag   4500
taaccatgca tcatcaggag tacggataaa atgcttgatg gtcggaagag gcataaattc   4560
cgtcagccag tttagtctga ccatctcatc tgtaacatca ttggcaacgc tacctttgcc   4620
atgtttcaga aacaactctg gcgcatcggg cttcccatac aatcgataga ttgtcgcacc   4680
tgattgcccg acattatcgc gagcccattt atacccatat aaatcagcat ccatgttgga   4740
atttaatcgc ggcctcgagc aagacgtttc ccgttgaata tggctcataa cacccttgt    4800
attactgttt atgtaagcag acagttttat tgttcatgat gatatatttt tatcttgtgc   4860
aatgtaacat cagagatttt gagacacaac gtggatcatc cagacatgat aagatacatt   4920
```

```
gatgagtttg gacaaaccac aactagaatg cagtgaaaaa aatgctttat ttgtgaaatt   4980
tgtgatgcta ttgctttatt tgtaaccatt ataagctgca ataaacaagt taacaacaac   5040
aattgcattc attttatgtt tcaggttcag ggggaggtgt gggaggtttt ttaaagcaag   5100
taaaacctct acaaatgtgg tatggctgat tatgatcgtc gaggatctgg atccgttaac   5160
cgatatccgc gaattcggcg cgccgggccc tcacgacgtg ttgatgaaca tctggacgat   5220
gtgcacgaac gactgcagga actccttgat gttcttctcc tccagctcct cgcactcctt   5280
gcagcccgac tccgtgacgt tcccgttcga cgacagcgag ttgttcgcca ggatgatcag   5340
gttctccacc gtgtcgtgga tcgacgcgtc cccgactcg agcgagatga cttggagctc    5400
caggaggaag cacttcatcg ccgtgacctt gcacgacggg tggacgtccg actccgtgta   5460
cagcgtcgcg tcgatgtgca tcgactggat gaggtcctcg atcttcttca ggtccgagat   5520
cacgttcacc cagttcgaga tgctgcaggc caccgtcccc aggagtagca ggctctggag   5580
ccacatttct tgtcgacaga tccaaacgct cctccgacgt ccccaggcag aatggcggtt   5640
ccctaaacga gcattgctta tatagacctc ccattaggca cgcctaccgc ccatttacgt   5700
caatggaacg cccatttgcg tcattgcccc tccccattga cgtcaatggg gatgtacttg   5760
gcagccatcg cgggccattt accgccattg acgtcaatgg gagtactgcc aatgtaccct   5820
ggcgtacttc caatagtaat gtacttgcca agttactatt aatagatatt gatgtactgc   5880
caagtgggcc atttaccgtc attgacgtca atagggggcg tgagaacgga tatgaatggg   5940
caatgagcca tcccattgac gtcaatggtg ggtggtccta ttgacgtcaa tgggcattga   6000
gccaggcggg ccatttaccg taattgacgt caatgggga ggcgccatat acgtcaatag    6060
gaccgcccat atgacgtcaa taggtaagac catgaggccc tttcgtctcg cgcgtttcgg   6120
tgatgacggt gaaaacctct gacacatgca gctcccggag acggtcacag cttgtctgta   6180
agcggatgcc gggagcagac aagcccgtca gggcgcgtca gcgggtgttg gcgggtgtcg   6240
gggctggctt aactatgcgg catcagagca gattgtactg agagtgcacc atatgcggtg   6300
tgaaataccg cacagatgcg taaggagaaa ataccgcatc agattggcta ttgg         6354
```

```
<210> SEQ ID NO 20
<211> LENGTH: 431
<212> TYPE: PRT
<213> ORGANISM: Artificial Sequence
<220> FEATURE:
<223> OTHER INFORMATION: synthetic sIL-15Ralpha-Fc fusion protein
      huIL15sRa200-Fc

<400> SEQUENCE: 20

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110
```

-continued

```
Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly Pro Lys Ser Cys Asp Lys Thr His
        195                 200                 205

Thr Cys Pro Pro Cys Pro Ala Pro Glu Leu Leu Gly Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
        275                 280                 285

Val Leu Thr Val Leu His Gln Asp Trp Leu Asn Gly Lys Glu Tyr Lys
    290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
            340                 345                 350

Val Lys Gly Phe Tyr Pro Ser Asp Ile Ala Val Glu Trp Glu Ser Asn
        355                 360                 365

Gly Gln Pro Glu Asn Asn Tyr Lys Thr Thr Pro Pro Val Leu Asp Ser
    370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
            420                 425                 430
```

USE OF IL-15 PREPARATIONS TO TREAT LYMPHOPENIA

CROSS REFERENCE TO RELATED APPLICATIONS

This application is a U.S. National Stage Application of International Application No. PCT/US2010, filed Aug. 13, 2010, which claims the benefit of U.S. provisional application No. 61/234,152, filed on Aug. 14, 2009; and U.S. provisional application No. 61/234,155, filed Aug. 14, 2009. Each application is herein incorporated by reference.

FIELD OF THE INVENTION

The present invention provides compositions and methods for promoting the maturation and export of T cells from the thymus, e.g., to peripheral lymphoid and non-lymphoid tissues by contacting the thymus tissue, in vitro or in vivo, with interleukin (IL)-15.

REFERENCE TO A SEQUENCE LISTING

This application includes a Sequence Listing as a text file named "SEQTXT_77867-828663_581100US.txt" created Feb. 13, 2012 and containing 65,889 bytes. The material contained in this text file is incorporated by reference.

The invention additionally provides methods for preventing, alleviating, reducing, and/or inhibiting lymphopenia or depletion of lymphocytes in peripheral tissues in a patient in need thereof by administering IL-15 to the patient.

BACKGROUND OF THE INVENTION

Two common gamma-chain cytokines, IL-2 and IL-7 are currently approved or considered for both AIDS and cancer immunotherapy. See, Sportes, et al., (2008) *J Exp Med* 205: 1701-1714; Levy, Y. (2009) *J Clin Invest.* 119(4):997-100785; and Rosenberg, et al., (2006) *J Immunother* 29:313-319. No clinical experience exists with the gamma-chain cytokine IL-15. See, Cheever, (2008) *Immunological Reviews* 222:357-368.

IL-15 is a non-redundant cytokine important for the development, survival, and proliferation of natural killer (NK) and CD8+ T-cells. It shares with IL-2 the same IL-2 beta gamma receptor and has many similar effects on lymphocytes, but unlike IL-2 is not produced by lymphocytes but by a plethora of other cells including, importantly, antigen presenting cells and macrophages, and stroma cells in several tissues. The biological effects of IL-2 and IL-15 at the level of the organism are dramatically different, as shown by work in knockout mice: lack of IL-15 causes immune system defects, whereas lack of IL-2 causes immune activation and severe autoimmunity. See, Waldmann, (2006) *Nat Rev Immunol* 6:595-601; and Ma, et al., (2006) *Annu Rev Immunol* 24:657-679. Both cytokines are under tight and complex regulation at all steps of expression and secretion. The biological differences of IL-2 and IL-15 are determined by their different production sites, their strength of association with membrane receptor proteins termed IL-2 Receptor alpha and IL-15 Receptor alpha (IL-15Rα), respectively, and the regulation of these extra receptor molecules. IL-15 has been also reported to have a unique mechanism of action in vivo among the common gamma chain cytokines: IL-15 functions in a complex with IL-15Rα and depends on the co-expression by the same cells of IL-15Rα. See, Burkett, et al., (2004) *J Exp Med* 200:825-834; Burkett, et al., (2003) *Proc Natl Acad Sci USA* 100:4724-4729; Dubois, et al., (2002) *Immunity* 17:537-547; Sandau, et al, (2004) *J Immunol* 173:6537-6541; Schluns, et al., (2004) *Blood* 103:988-994; Rubinstein, et al., (2006) *Proc Natl Acad Sci USA* 103:9166-9171; Bergamaschi, et al., (2008) *J Biol Chem* 283:4189-4199. IL-15 has non-redundant roles in the development and function of NK and intestinal intraepithelial lymphocytes (IELs). See, Cooper, et al., (2001) *Blood* 97:3146-3151. It stimulates cytolytic activity, cytokine secretion, proliferation and survival of NK cells. See, Fehniger, et al., (1999) *J Immunol* 162:4511-4520; Ross, et al., (1997) *Blood* 89:910-918; and Carson, et al., (1994) *J Exp Med* 180:1395-1403. IL-15 has a proliferative and survival effect on CD8+ memory T-cells and naive CD8+ T-cells. See, Tan, et al., (2002) *J Exp Med* 195:1523-1532; Zhang, et al., (1998) *Immunity* 8:591-599; Berard, et al., (2003) *J Immunol* 170: 5018-5026; and Alves, et al., (2003) *Blood* 102:2541-2546.

Several studies have evaluated the effects of IL-15 administration in vivo. CD8+ memory T-cell proliferation increased after a single dose of IL-15 in normal mice. See, Zhang, et al., (1998) *Immunity* 8:591-599. Administration of IL-15 to mice enhanced the antitumor activity after syngeneic bone marrow transplantation (BMT) and antigen-specific primary CD8+ T-cell responses following vaccination with peptide-pulsed dendritic cells. See, Rubinstein, et al., (2002) *J Immunol* 169:4928-4935; Katsanis, et al., (1996) *Transplantation* 62:872-875. IL-15 also enhanced immune reconstitution after allogeneic bone marrow transplantation. See, Alpdogan, et al., (2005) *Blood* 105:865-873; and Evans, et al., (1997) *Cell Immunol* 179:66-73. The ability of IL-15 to promote growth, survival and activation of key lymphocyte populations make it also an attractive candidate for supporting growth in vitro and in vivo of cells for adoptive cell therapy. See, Rosenberg, et al., (2008) *Nat Rev Cancer* 8:299-308; and Berger, et al., (2008) *J Clin Invest* 118:294-305.

We have demonstrated that efficient production of IL-15 requires the expression of IL-15 and IL-15 Receptor alpha (IL-15Rα) in the same cell. See, Bergamaschi, et al., (2008) *J Biol Chem* 283:4189-4199. Co-production leads to intracellular association of IL-15 and IL-15Rα in the endoplasmic reticulum, stabilization of both molecules and efficient transport to the cell surface (FIG. 1). We showed that an additional critical step is the rapid cleavage and release of the IL-15/IL-15Rα complex from the cell surface, both in vitro and in vivo, resulting in a soluble, systemically active form of IL-15/IL-15Rα, in addition to the bioactive complex on the cell surface. See, Dubois, et al., (2002) *Immunity* 17:537-547; Bergamaschi, et al., (2008) *J Biol Chem* 283:4189-4199; and Budagian, et al., (2004) *J Biol Chem* 279:40368-40375. Our experiments using IL-15 complexed to a deletion mutant of IL-15Rα containing only the soluble Receptor alpha extracellular fragment demonstrated that this complex is bioactive in vivo in the absence of any membrane-bound form.

Therefore, we proposed that IL-15Rα is part of a heterodimeric IL-15 cytokine, rather than functioning as a cytokine receptor. These results have been supported by other investigators, and provide the basis for a better understanding of IL-15 biology. See, Duitman, et al., (2008) *Mol Cell Biol* 28:4851-4861; Mortier, et al., (2008) *J Exp Med* 205:1213-1225. The results also provide the molecular basis to explain some intriguing observations, including the requirement of production of IL-15 and IL-15Rα from the same cells for appropriate function in vivo. See, Sandau, et al., (2004) *J Immunol* 173:6537-6541; and Koka, et al., (2003) *J Exp Med* 197:977-984. Such results are fully explained by our finding that stabilization during co-expression in the same cell is required for physiological levels of IL-15 production. It has also been reported that the cells that physiologically express IL-15 also express IL-15Rα, consistent with IL-15 production as a heterodimer in the body. See, Dubois, et al., (2002) *Immunity* 17:537-547; Giri, et al., (1995) *J Leukoc Biol* 57:763-766; and Ruckert, et al., (2003) *Eur J Immunol* 33:3493-3503. Interpretation of all data available to date suggests that the main bioactive form of IL-15 is in a complex with the Receptor alpha either on the surface of the cells or in a soluble circulating form. It remains to be determined whether single-chain IL-15 is produced in the body in physiologically relevant levels and what is its exact function.

It has been previously reported that IL-15 secretion is inefficient. See, Bamford, et al., (1998) *J Immunol* 160:4418-4426; Gaggero, et al., (1999) *Eur J Immunol* 29:1265-1274; Kurys, et al., (2000) *J Biol Chem* 275:30653-30659; Onu, et al., (1997) *J Immunol* 158:255-262; and Tagaya, et al., (1997) *Proc Natl Acad Sci USA* 94:14444-14449. We took a systematic approach to develop IL-15 expression vectors producing high levels of bioactive cytokine based on the observation that multiple regulatory steps during gene expression create bottlenecks of IL-15 production. See, Jalah, et al., (2007) *DNA Cell Biol* 26:827-840; and Kutzler, et al., (2005) *J Immunol* 175:112-123. We showed that combination of two approaches, namely mRNA optimization (RNA/codon optimization) of the IL-15 coding sequences and substitution of the signal peptide with other efficient secretory signals resulted in synergistically improved expression and secretion of bioactive IL-15. See, Jalah, et al., (2007) *DNA Cell Biol* 26:827-840. Taking advantage of the stabilization of IL-15 by co-expression with IL-15Rα described above, we produced equally optimized vectors for IL-15Rα and combination vectors expressing both molecules, as well as combinations producing only the soluble heterodimeric cytokine. The final improvement in expression of secreted IL-15 was more than 1,000 fold compared to wt IL-15 cDNA, as determined by in vitro and in vivo experiments. We have produced similar vectors for mouse, macaque and human IL-15/IL-15Rα.

Two forms of interleukin-15 (IL-15) are known, containing a long signal peptide (LSP) or a short signal peptide (SSP), respectively. The two forms are produced by alternatively spliced mRNAs and differ only in the length of their signal peptides, the 48 aa long signal peptide or the 21 aa short signal peptide (120, 121, 125-127). See, Onu, et al., (1997) *J Immunol* 158:255-262; Tagaya, et al., (1997) *Proc Natl Acad Sci USA* 94:14444-14449; Meazza, et al., (1997) *Eur J Immunol* 27:1049-1054; Meazza, et al., (1996) *Oncogene* 12:2187-2192; and Nishimura, et al., (1998) *J Immunol* 160:936-942. Whereas LSP IL-15 is secreted, SSP IL-15 remains exclusively intracellular and its function is not known. It has been proposed that SSP IL-15 may have a regulatory function since it was detected both in the cytoplasm and the nucleus of DNA-transfected cells. The SSP signal affects both stability and localization of IL-15, since lower levels of the SSP isoform were detected when the two isoforms were expressed from similar vectors. See, See, Onu, et al., (1997) *J Immunol* 158:255-262; Tagaya, et al., (1997) *Proc Natl Acad Sci USA* 94:14444-14449; and Bergamaschi, et al., (2009) *J Immunol,* 5:3064-72.

In Bergamaschi, we showed that, similar to LSP IL-15, SSP IL-15 is stabilized and secreted efficiently upon coexpression of IL-15Rα in the same cell. See, Bergamaschi, et al., (2009) *J Immunol*, supra. Co-expression of SSP IL-15 and IL-15Rα in mice showed increased plasma levels of bioactive SSP IL-15 and mobilization and expansion of NK and T cells. Therefore, SSP IL-15 is secreted and bioactive when produced as a heterodimer with IL-15Rα in the same cell. The apparent stability of this complex both in vitro and in vivo is lower compared to LSP IL-15/IL-15Rα complex, as revealed by direct comparisons. This results in lower production of secreted bioactive IL-15/IL-15Rα. Thus, alternative splicing may provide the cell with the ability to produce different levels of bioactive IL-15. Since both forms of IL-15 may be produced in the same cell by alternative splicing, an additional level of regulation is possible. We showed that when both LSP IL-15 and SSP IL-15 are produced in the same cell they compete for the binding to IL-15Rα, resulting in lower levels of bioactive IL-15. Therefore, co-expressed SSP IL-15 acts as competitive inhibitor of LSP IL-15. This suggests that usage of alternative splicing is an additional level of control of IL-15 activity. Expression of both SSP and LSP forms of IL-15 appears to be conserved in many mammals, suggesting that SSP may be important for expressing a form of IL-15 with lower magnitude and duration of biological effects. The present invention is based, in part, on the discovery that SSP IL-15, which is produced in the thymus, is important for intrathymic effects on lymphocyte differentiation and maturation.

BRIEF SUMMARY OF THE INVENTION

The present invention provides compositions and methods that promote the maturation of T cells in the thymus and the output or migration of mature and/or activated lymphocytes from a central lymphoid organ to peripheral tissues by administration of IL-15. The invention is based, in part, on the discovery that IL-15 promotes the migration of T cells out of the thymus and subsequently to peripheral lymphoid (e.g., spleen and lymph node) and non-lymphoid tissues (e.g., lung and liver). In some embodiments, the methods concurrently promote the maturation of lymphocytes in the bone marrow, e.g., B cells and natural killer (NK) cells, and their migration to peripheral lymphoid and non-lymphoid tissues.

Accordingly, in one aspect, the invention provides methods of promoting T-cell maturation in thymic tissue comprising contacting the thymic tissue with IL-15.

The thymic tissue can be in vivo or in vitro.

In a related aspect, the invention provides methods of promoting the migration of lymphocytes from a central lymphoid tissue to one or more peripheral tissues in a subject in need thereof comprising administering to the subject IL-15.

With respect to the embodiments, in some embodiments, the lymphocytes are T cells and the central lymphoid tissue is thymus. In some embodiments, the lymphocytes are B cells and/or NK cells and the central lymphoid tissue is bone marrow.

In some embodiments, the lymphocytes migrating from the central lymphoid tissues are mature but not activated. In some embodiments, the lymphocytes migrating from the central lymphoid tissues are mature and activated. In some embodiments, the T cells migrating from the thymus are mature single positive (CD4+ or CD8+) T cells. The T cells induced to leave the thymus may be activated or not activated.

The invention additionally provides methods for preventing, treating, alleviating, reducing and/or inhibiting lymphopenia or depletion of lymphocytes in peripheral tissues by administration of IL-15. The present invention further provides methods for promoting the repopulation of peripheral tissues that have been depleted of lymphocytes and accelerating the recovery from lymphocyte depletion of peripheral tissues by the administration of IL-15.

Accordingly, in one aspect, the invention provides methods of preventing, reducing or inhibiting lymphopenia or depletion of lymphocytes in peripheral tissues in an individual in need thereof comprising systemically administering IL-15 to the individual.

In some embodiments, the lymphopenia or lymphocyte depletion of peripheral tissues is drug-induced. For example, the individual may be receiving anticancer drugs or antiviral drugs, or radiation therapy that induces lymphopenia or lymphocyte depletion of peripheral tissues.

In some embodiments, the IL-15 is co-administered with an agent that causes depletion of lymphocytes in peripheral tissues, e.g., an anticancer or an antiviral agent. In some embodiments, the IL-15 is co-administered with radiation therapy.

In a related aspect, the invention provides methods of promoting or accelerating the repopulation of lymphocytes in peripheral tissues in an individual in need thereof comprising systemically administering IL-15 to the individual.

In some embodiments, the systemic administration of IL-15 prevents or reduces the depletion of or promotes or accelerates the repopulation of one or more of T cells, B cells or NK cells. In some embodiments, the systemic administration of IL-15 prevents or reduces the depletion of or promotes or accelerates the repopulation of one or more of CD4+ T cells or CD8+ T cells.

In some embodiments of the methods of the invention, the subject or patient is a mammal. In some embodiments, the subject or patient is a human.

When administered in vivo the IL-15 can be administered systemically, including without limitation, enterally (i.e., orally) or parenterally, e.g., intravenously, intramuscularly, subcutaneously, intradermally, intranasally, or inhalationally. In some embodiments, the IL-15 is administered locally, for example, intrathymically.

Systemic administration is at a dose that is sufficient to maintain IL-15 at supraphysiologic levels. For example, IL-15 DNA or protein can be administered at a dose sufficient to achieve plasma levels of IL-15 of about 1 to 1000 ng/ml, for example, plasma levels of IL-15 of about 10 to 1000 ng/ml. The IL-15 and IL-15Rα can be delivered in equimolar amounts. Such a range of IL-15 plasma concentrations can be achieved, e.g., after intramuscular electroporation of about 0.1 mg IL-15/IL-15Rα expressing DNA plasmid per kg body weight. Alternatively, an IL-15/IL-15Rα protein complex can be administered at a dose of about 0.01 to 0.5 mg/kg. IL-15/IL-15Rα polypeptides can be administered, e.g., subcutaneously, intramuscularly, intraperitoneally or intravenously. See, e.g., Rosati, et al., *Vaccine* (2008) 26:5223-5229.

The IL-15 can be administered as a polypeptide or as a polynucleotide encoding IL-15. In some embodiments, the IL-15 is co-administered with IL-15Rα, e.g., as a heterodimer. The co-administered IL-15Rα can be a polypeptide or a polynucleotide encoding IL-15Rα. The co-administered IL-15Rα can be in the same or different form as the IL-15. For example, both the IL-15 and the IL-15Rα can be administered as polypeptides or as one or more polynucleotides encoding IL-15 and/or IL15Rα. Alternatively, one of the IL-15 and the IL15Rα can be administered as a polypeptide and the other as a polynucleotide encoding either IL-15 or IL-15Rα. In some embodiments, the IL-15Rα is a soluble IL-15Rα. In some embodiments, the IL-15Rα may be administered in the form of an Fc fusion protein or a polynucleotide that encodes an Fc fusion protein.

In some embodiments, the IL-15 and the IL-15Rα are concurrently administered as one or more polynucleotides encoding IL-15 and/or IL-15Rα. The polynucleotide encoding IL-15 and the polynucleotide encoding IL-15Rα can be on the same or separate vectors, for example, single or multiple plasmid vectors. In some embodiments, the IL-15 and the IL-15Rα polynucleotides are concurrently expressed from a plasmid vector of SEQ ID NO:13, SEQ ID NO:14, SEQ ID NO:15, SEQ ID NO:16, or SEQ ID NO: 19.

In some embodiments, the polynucleotides encoding one or both of IL-15 and the IL-15Rα are wild-type coding sequences. In some embodiments, the polynucleotide encoding IL-15 shares at least 90%, 91%, 92%, 93%, 94%, 95%, 96%, 97%, 98%, 99% or 100% sequence identity to SEQ ID NO:1. In some embodiments, the polynucleotide encoding IL-15Rα shares at least 90%, 91%, 92%, 93%, 94%, 95%, 96%, 97%, 98%, 99% or 100% sequence identity to SEQ ID NO:5 or SEQ ID NO:7.

In some embodiments, the polynucleotides encoding one or both of IL-15 and the IL-15Rα are codon optimized for improved expression over the wild-type coding sequences. In some embodiments, the polynucleotide encoding IL-15 shares at least 90%, 91%, 92%, 93%, 94%, 95%, 96%, 97%, 98%, 99% or 100% sequence identity to SEQ ID NO:3 or SEQ ID NO:4. In some embodiments, the polynucleotide encoding IL-15Rα shares at least 90%, 91%, 92%, 93%, 94%, 95%, 96%, 97%, 98%, 99% or 100% sequence identity to SEQ ID NO:9 or SEQ ID NO:11.

When expressed from a polynucleotide encoding IL-15, the coding sequence can have a native or a heterologous signal peptide. In some embodiments, the signal peptide is a native IL-15 signal peptide, for example, the native IL-15 long signal peptide or the native IL-15 short signal peptide. In some embodiments, the signal peptide is a heterologous signal peptide, for example, a signal peptide from granulocyte-macrophage colony stimulating factor (GM-CSF), tissue plasminogen activator (tPA), growth hormone, or an immunoglobulin.

In some embodiments, the peripheral tissue is a peripheral lymphoid tissue, including without limitation, spleen, lymph node, mucosal-associated lymphoid tissues (MALT), e.g., tonsils and/or gut-associated lymphoid tissues (GALT), including Peyer's patches.

In some embodiments, the peripheral tissue is a peripheral non-lymphoid tissue, e.g., lung, liver, kidney, heart, skin, etc.

Preferably, the IL-15 is administered without an antigen, i.e., is not co-administered with an antigen.

In a related aspect, the invention provides a DNA vector encoding IL-15 and IL-15Rα for use in promoting lymphocyte mobilization from central lymphoid tissue and migration to peripheral tissues.

In another aspect, the invention provides IL-15/IL-15Rα for use in promoting lymphocyte mobilization from central lymphoid tissue and migration to peripheral tissues.

In a related aspect, the invention provides a DNA vector encoding IL-15 and IL-15Rα for use in promoting the maturation and export of T cells from the thymus to peripheral tissues, including peripheral lymphoid and non-lymphoid tissues.

In another aspect, the invention provides IL-15/IL-15Rα polypeptide complexes for use in promoting the maturation and export of T cells from the thymus to peripheral tissues, including peripheral lymphoid and non-lymphoid tissues.

In a related aspect, the invention provides a DNA vector encoding IL-15 and IL-15Rα for use in promoting repopulation of depleted lymphocytes in peripheral tissues and/or preventing, reducing and/or inhibiting lymphopenia.

In another aspect, the invention provides IL-15/IL-15Rα polypeptide complexes for use in promoting repopulation of depleted lymphocytes in peripheral tissues and/or preventing, reducing and/or inhibiting lymphopenia.

In another aspect, the invention provides stable cell lines that express IL-15/IL-15Rα polypeptides. In some embodiments, the stable cell line expresses IL-15/IL-15Rα in the form of a fusion protein. In some embodiments, the stable cell lines produce IL-15 and IL-15Rα as different molecules. In some embodiments, the stable cell lines produce IL-15 and secreted IL-15Rα deletions that lack the transmembrane anchor portion of the receptor. In some embodiments the stable cell lines produce IL-15 and fusions of IL15Rα to the an immunoglobulin Fc region. In some embodiments the stable cell lines produce IL-15 and IL-15Rα fusions to polypeptides able to direct binding of the fusion to the cell surface of specific cell types. In some embodiments the stable cell lines produce IL-15 and IL-15Rα fusions to polypeptides able to direct multimerization of the fusion.

Further embodiments are as described herein.

DEFINITIONS

The term "central lymphoid tissue" or "central lymphoid organ" refers to specialized lymphoid tissues where the production of new lymphocytes, or lymphopoiesis, takes place. For example, T cells develop and mature in the thymus or thymic tissue. B cells and natural killer (NK) cells develop in bone marrow tissue. See, e.g., Chapter 7 of Janeway, et al., *Immunobiology,* 2001, Garland Publishing, New York.

The term "peripheral lymphoid tissue" or "peripheral lymphoid organ" refers to peripheral tissues of highly organized architecture, with distinct areas of B cells and T cells. Newly produced lymphocytes leave the central lymphoid tissues, and are carried in the blood to the peripheral lymphoid tissues. Exemplary peripheral lymphoid tissues or organs include the spleen, lymph nodes, mucosal-associated lymphoid tissues (MALT), e.g., tonsils and gut-associated lymphoid tissues (GALT), including Peyer's patches.

The term "mature lymphocyte" refers to a lymphocyte that is undergone selection and development to maturity in the central lymphoid tissue sufficient to circulate to peripheral lymphoid tissues. With respect to T cells, a mature T cell is characterized by the expression of either CD4 or CD8, but not both (i.e., they are single positive), and expression of CD3. With respect to B cells, a mature B cell is characterized by VDJ rearranged immunoglobulin heavy chain gene, VJ rearranged immunoglobulin light chain gene, and the surface expression of IgD and/or IgM. The mature B cell may also express CD19 and the IL-7 receptor on the cell surface.

The term "activated lymphocyte" refers to lymphocytes that have recognized an antigen bound to a MHC molecule and the simultaneous delivery of a co-stimulatory signal by a specialized antigen-presenting cell. Activation of lymphocytes changes the expression of several cell-surface molecules.

With respect to T cells, resting naive T cells express L-selectin, and low levels of other adhesion molecules such as CD2 and LFA-1. Upon activation of the T cell, expression of L-selectin is lost and, instead, increased amounts of the integrin VLA-4 are expressed. Activated T cells also express higher densities of the adhesion molecules CD2 and LFA-1, increasing the avidity of the interaction of the activated T cell with potential target cells, and higher densities of the adhesion molecule CD44. Finally, the isoform of the CD45 molecule expressed by activated cells changes, by alternative splicing of the RNA transcript of the CD45 gene, so that activated T cells express the CD45RO isoform that associates with the T-cell receptor and CD4. Also, with respect to cytokine production, resting T cells produce little or no IL-2 and the β and γ subunits of the IL-2 receptor. In contrast, activated T cells produce significant amounts IL-2 along with the α chain of the IL-2 receptor.

With respect to B cells, activated B cells have undergone isotype switching and secrete immunoglobulin. Naive B cells express cell-surface IgM and IgD immunoglobulin isotypes. In contrast, activated or memory B cells express and secrete IgG, IgA or IgE immunoglobulin isotypes.

The terms "output" or "migration" from a central lymphoid tissue refers to migration or export of mature lymphocytes from a central lymphocyte tissue to a peripheral tissue, including lymphoid and non-lymphoid peripheral tissues. Output includes the migration of mature T cells from the thymus and the migration of mature B cells and NK cells from the bone marrow.

The terms "treating" and "treatment" refer to delaying the onset of, retarding or reversing the progress of, or alleviating or preventing either the disease or condition to which the term applies, or one or more symptoms of such disease or condition.

The terms "lymphopenia" or "lymphocytopenia" or "lymphocytic leucopenia" interchangeably refer to an abnormally small number of lymphocytes in the circulating blood or in peripheral circulation. Quantitatively, lymphopenia can be described by various cutoffs. In some embodiments, a patient is suffering from lymphopenia when their circulating blood total lymphocyte count falls below about 600/mm$^3$. In some embodiments, a patient suffering from lymphopenia has less than about 2000/μL total circulating lymphocytes at birth, less than about 4500/μL total circulating lymphocytes at about age 9 months, or less than about 1000/μL total circulating lymphocytes patients older than about 9 months (children and adults). Lymphocytopenia has a wide range of possible causes, including viral (e.g., HIV infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. Lymphopenia may also be of unknown etiology (i.e., idiopathic lymphopenia). Peripheral circulation of all types of lymphocytes or subpopulations of lymphocytes (e.g., CD4+ T cells) may be depleted or abnormally low in a patient suffering from lymphopenia. See, e.g., The Merck Manual, 18$^{th}$ Edition, 2006, Merck & Co.

The term "native mammalian interleukin-15 (IL-15)" refers to any naturally occurring interleukin-15 nucleic acid and amino acid sequences of the IL-15 from a mammalian species. Those of skill in the art will appreciate that interleukin-15 nucleic acid and amino acid sequences are publicly available in gene databases, for example, GenBank through the National Center for Biotechnological Information on the worldwide web at ncbi.nlm.nih.gov. Exemplified native mammalian IL-15 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_172174.2 (human preproprotein); NM_172175 (human); NM_000585.3 (human preproprotein); U19843 (macaque); DQ021912 (macaque); AB000555 (macaque); NM_214390 (porcine); DQ152967 (ovine); NM_174090 (bovine); NM_008357 (murine); NM_013129 (rattus); DQ083522 (water buffalo); XM_844053 (canine); DQ157452 (lagomorpha); and NM_001009207 (feline). Accession numbers for exemplified native mammalian IL-15 amino acid sequences include NP_000576.1 (human preproprotein); NP_751914 (human preproprotein); CAG46804 (human); CAG46777 (human); AAB60398 (macaque); AAY45895 (macaque); NP_999555 (porcine); NP_776515 (bovine); AAY83832 (water buffalo); ABB02300 (ovine); XP_849146 (canine); NP_001009207 (feline); NP_037261 (rattus); and NP_032383 (murine).

The term "interleukin-15" or "IL-15" refers to a polypeptide that has at least 90%, 91%, 92%, 93%, 94%, 95%, 96%, 97%, 98% or 99% sequence identity to a native mammalian IL-15 amino acid sequence, or a nucleotide encoding such a polypeptide, is biologically active, meaning the mutated protein ("mutein") has functionality similar (75% or greater) to that of a native IL-15 protein in at least one functional assay. Functionally, IL-15 is a cytokine that regulates T cell and natural killer cell activation and proliferation. IL-15 and IL-2 share many biological activities, including binding to CD122, the IL-2β/IL-15β receptor subunit. The number of CD8+ memory cells is controlled by a balance between this IL-15 and IL-2. IL-15 induces the activation of JAK kinases, as well as the phosphorylation and activation of transcription activators STAT3, STAT5, and STAT6. IL-15 also increases the expression of apoptosis inhibitor BCL2L1/BCL-x(L), possibly through the transcription activation activity of STAT6, and thus prevents apoptosis. Two alternatively spliced transcript variants of the IL-15 gene encoding the same mature protein have been reported. Exemplified functional assays of an IL-15 polypeptide include proliferation of T-cells (see, for example, Montes, et al., *Clin Exp Immunol* (2005) 142:292), and activation of NK cells, macrophages and neutrophils. Methods for isolation of particular immune cell subpopulations and detection of proliferation (i.e., $^{3}$H-thymidine incorporation) are well known in the art. Cell-mediated cellular cytotoxicity assays can be used to measure NK cell, macrophage and neutrophil activation. Cell-mediated cellular cytotoxicity assays, including release of isotopes ($^{51}$Cr), dyes (e.g., tetrazolium, neutral red) or enzymes, are also well known in the art, with commercially available kits (Oxford Biomedical Research, Oxford, M; Cambrex, Walkersville, Md.; Invitrogen, Carlsbad, Calif.). IL-15 has also been shown to inhibit Fas mediated apoptosis (see, Demirci and Li, *Cell Mol Immunol* (2004) 1:123). Apoptosis assays, including for example, TUNEL assays and annexin V assays, are well known in the art with commercially available kits (R&D Systems, Minneapolis, Minn.). See also, Coligan, et al., Current Methods in Immunology, 1991-2006, John Wiley & Sons.

The term "native mammalian interleukin-15 Receptor alpha (IL15Rα)" refers to any naturally occurring interleukin-15 receptor alpha nucleic acid and amino acid sequences of the IL-15 receptor alpha from a mammalian species. Those of skill in the art will appreciate that interleukin-15 receptor alpha nucleic acid and amino acid sequences are publicly available in gene databases, for example, GenBank through the National Center for Biotechnological Information on the worldwide web at ncbi.nlm.nih.gov. Exemplified native mammalian IL-15 receptor alpha nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-15 nucleic acid sequences include NM_172200.1 (human isoform 2); and NM_002189.2 (human isoform 1 precursor). Accession numbers for exemplified native mammalian IL-15 amino acid sequences include NP_751950.1 (human isoform 2); and NP_002180.1 (human isoform 1 precursor).

The term "interleukin-15 receptor alpha" or "IL15Rα" refers to a polypeptide that has at least 90%, 91%, 92%, 93%, 94%, 95%, 96%, 97%, 98% or 99% sequence identity to a native mammalian IL15Rα amino acid sequence, or a nucleotide encoding such a polypeptide, is biologically active, meaning the mutated protein ("mutein") has functionality similar (75% or greater) to that of a native IL15Rα protein in at least one functional assay. IL15Rα is a cytokine receptor that specifically binds IL15 with high affinity. One functional assay is specific binding to a native IL-15 protein.

The term "soluble IL-15 Receptor alpha" or "sIL-15α" refers to forms of IL-15 Receptor alpha lacking the transmembrane anchor portion of the receptor and thus able to be secreted out of the cell without being anchored to the plasma membrane. Exemplary sIL-15α include aa 31-205 and aa31-185 of the native IL-15 Receptor alpha.

An "IL-15Rα Fc fusion" or an "IL-15Rα fused to an Fc region" as used herein refers to forms of IL-15Rα in which the protein is fused to one or more domains of an Fc region of an immunoglobulin, typically of an IgG immunoglobulin. The Fc region comprises the CH2 and CH3 domains of the IgG heavy chain and the hinge region. The hinge serves as a flexible spacer between the two parts of the Fc-Fusion protein, allowing each part of the molecule to function independently. The use of Fc fusions is known in the art (see, e.g., U.S. Pat. Nos. 7,754,855; 5,480,981; 5,808,029; Wo7/23614; Wo98/28427 and references cited therein. Fc fusion proteins can include variant Fc molecules (e.g., as described in U.S. Pat. No. 7,732,570). Fc fusion proteins can be soluble in the plasma or can associate to the cell surface of cells having specific Fc receptors.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| 1st position | 2nd position | | | | 3rd position |
|---|---|---|---|---|---|
| (5' end) | U(T) | C | A | G | (3' end) |
| U(T) | Phe | Ser | Tyr | Cys | U(T) |
| | Phe | Ser | Tyr | Cys | C |
| | Leu | Ser | STOP | STOP | A |
| | Leu | Ser | STOP | Trp | G |

TABLE 1-continued

| 1st position | 2nd position | | | | 3rd position |
|---|---|---|---|---|---|
| (5' end) | U(T) | C | A | G | (3' end) |
| C | Leu | Pro | His | Arg | U(T) |
| | Leu | Pro | His | Arg | C |
| | Leu | Pro | Gln | Arg | A |
| | Leu | Pro | Gln | Arg | G |
| A | Ile | Thr | Asn | Ser | U(T) |
| | Ile | Thr | Asn | Ser | C |
| | Ile | Thr | Lys | Arg | A |
| | Met | Thr | Lys | Arg | G |
| G | Val | Ala | Asp | Gly | U(T) |
| | Val | Ala | Asp | Gly | C |
| | Val | Ala | Glu | Gly | A |
| | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., of a IL-15 or IL-15Rα sequence), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-15 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The term "therapeutically effective amount" refers to the dose of a therapeutic agent or agents sufficient to achieve the intended therapeutic effect with minimal or no undesirable side effects. A therapeutically effective amount can be readily determined by a skilled physician, e.g., by first administering a low dose of the pharmacological agent(s) and then incrementally increasing the dose until the desired therapeutic effect is achieved with minimal or no undesirable side effects.

The term "supraphysiologic levels" refers to levels of IL-15 in a particular tissue, e.g., blood, plasma, serum, thymus, that are above naturally occurring physiologic levels.

Supraphysiologic levels of IL-15 in a tissue can also be achieved when the concentration of IL-15 in that tissue is sustained above naturally occurring levels for an extended period of time, e.g., for consecutive days or weeks or for the duration of therapeutic treatment. For example, IL-15 DNA or protein can be administered at a dose sufficient to achieve plasma levels of IL-15 of about 1 to 1000 ng/ml, for example, plasma levels of IL-15 of about 10 to 1000 ng/ml. The IL-15 and IL-15Rα can be delivered in equimolar amounts. Alternatively, an IL-15/IL-15Rα protein complex can be administered at a dose of about 0.01 to 0.5 mg/kg.

The term "co-administer" refers to the presence of two pharmacological agents, e.g., IL-15 and IL-15Rα, in the blood at the same time. The two pharmacological agents can be administered concurrently or sequentially.

The term "consisting essentially of" refers to administration of the pharmacologically active agents expressly recited, e.g., IL-15 and IL-15Rα, and excludes pharmacologically active agents not expressly recited, e.g., an antigen. The term consisting essentially of does not exclude pharmacologically inactive or inert agents, e.g., physiologically acceptable carriers or excipients.

DETAILED DESCRIPTION

1. Introduction

Figure 1:
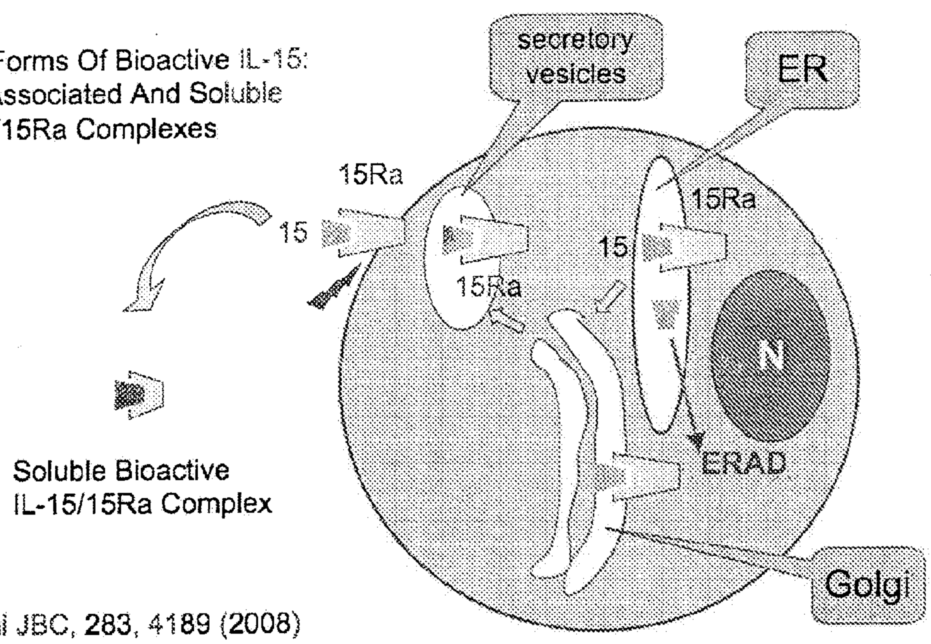
FIG. 1 illustrates a schematic of the mutual stabilization of IL-15 and IL-15α.

The present invention is based, in part, on the surprising discovery that subjecting thymic tissue to supraphysiological levels of IL-15 promotes the maturation of T cells in the thymus from double positive CD4+CD8+ T cells to single positive (i.e., CD4+ or CD8+) CD3high T cells, decreases the frequency of apoptotic thymocytes, and increases the migration of mature T cells from the thymus to peripheral tissues, including lymphoid and non-lymphoid peripheral tissues.

The present invention is further based, in part, on the surprising discovery that systemic administration of supraphysiological levels of IL-15 promotes the maturation and export of lymphocytes from central lymphoid tissues (e.g., in the thymus and bone marrow) to peripheral tissues, including lymphoid and non-lymphoid peripheral tissues.

2. Methods of Promoting Maturation of Lymphocytes in a Central Lymphoid Organ and the Migration of the Lymphocytes to Peripheral Tissues The present invention provides methods of promoting T cell maturation in the thymus, decreasing apoptosis of T cells in the thymus and promoting migration or output of mature T cells from the thymus, by contacting the thymus tissue with supraphysiological levels of IL-15. The thymic tissue can be in vivo or in vitro.

When the IL-15 is administered in vivo, it is provided to a subject or patient or individual in need thereof. The subject can be any mammal. In some embodiments, the mammal is a human or a non-human primate. Subjects who will benefit from the present methods have a deficiency of mature thymocytes and/or other lymphocytes in peripheral tissues, including lymphoid and non-lymphoid peripheral tissues. In some embodiments, the subject is immunodeficient or has lymphopenia. In some embodiments, the subject has a drug-induced immunodeficiency, e.g., due to anticancer drugs. In some embodiments, the subject has an immunodeficiency secondary to a disease, e.g., HIV infection. In some embodiments, the subject may have a genetic mutation that results in a non-functional IL-15 or non-functional IL-15 receptor subunit (e.g., IL-15Rα, IL-15Rβ, or IL-15Rγ).

Sustained exposure of thymic tissue to supraphysiological levels of IL-15 promotes the maturation of double positive T cells. IL-15 promotes the terminal differentiation of the thymocytes to single positive T cells expressing either CD4 or CD8. The mature T cells also may express CD122 (also known as the beta subunit of IL-2/IL-15 receptor). The mature T cells may also express high levels of the CD3 surface protein. IL-15-induced maturation of T cells also corresponds to a reduction in the frequency of immature T cells that undergo apoptosis. By contacting the thymic tissue with supraphysiologic levels of IL-15, the CD4+CD8+ double positive and CD3low T cells can be substantially eliminated as the cells mature into single positive CD3high T cells. After exposure to supraphysiologic levels of IL-15, at least 60%, 70%, 80%, 90%, 95% or more of the T cells are CD4+ or CD8+ single positive CD3high T cells.

IL-15-induced maturation of T cells in thymus tissue also promotes the migration of the mature T cells to the peripheral tissues, including lymphoid and non-lymphoid peripheral tissues. The mature T cells leaving the thymus may or may not be activated. For example, after about 2, 3, 4, 5, 6, 7, 8, 9, 10 or more days exposure to supraphysiologic levels of IL-15, the thymus organ may have decreased in size, e.g., by at least about 30%, 40%, 50%, or more, due to IL-15-induced thymic output.

Systemic administration of supraphysiologic levels of IL-15, e.g., sustained over the course of e.g., about 2, 3, 4, 5, 6, 7, 8, 9, 10 or more days, also promotes the maturation and migration of lymphocytes, including NK cells, from bone marrow. For example, after about 2, 3, 4, 5, 6, 7, 8, 9, 10 or more days exposure to supraphysiologic levels of IL-15, the percentage of lymphocytes in the bone marrow may have decreased, e.g., by at least about 50%, 60%, 70%, 80%, or more, due to IL-15-induced lymphocyte output from bone marrow.

At the same time that the number of lymphocytes decrease in the central lymphoid tissues, i.e., in the thymus and bone marrow, the number of lymphocytes in peripheral lymphoid tissues, e.g., spleen, lymph node, mucosal-associated lymphoid tissues (MALT), e.g., tonsils and/or gut-associated lymphoid tissues (GALT), including Peyer's patches, increases. Furthermore, the number of lymphocytes in peripheral non-lymphoid tissues, including the lung, liver, kidney, skin, and other tissues, also increases. In some embodiments, the administration of supraphysiologic levels of IL-15 increases the number of lymphocytes, including T cells, B cells and NK cells, in the blood.

3. Methods of Treating Lymphopenia

As explained above, in one aspect, the invention is based on the discovery that systemic administration of supraphysiological levels of IL-15 promotes the maturation and export of lymphocytes from central lymphoid tissues (e.g., in the thymus and bone marrow) to peripheral tissues, including lymphoid and non-lymphoid peripheral tissues.

Accordingly, the invention provides methods for preventing, reducing and inhibiting the depletion of lymphocytes, including T cells, B cells and natural killer (NK) cells, in peripheral circulation or tissues by systemic administration of IL-15 to a subject in need thereof. The present invention also provides methods for accelerating the recovery from and shortening the time period of depletion of lymphocytes, including T cells, B cells and natural killer (NK) cells, in peripheral circulation or tissues by systemic administration of IL-15 to a subject in need thereof.

The subject, patient or individual can be any mammal. In some embodiments, the mammal is a human or a non-human primate. In some embodiments, the individual is a domestic mammal (e.g., a canine or feline), a laboratory mammal (e.g., a mouse, a rat, a rabbit, a hamster), or an agricultural mammal (e.g., a bovine, a porcine, a ovine, an equine). Subjects who will benefit from the present methods either already have or will have (e.g., as a result of a course of drug treatment) a deficiency of mature lymphocytes in peripheral circulation or tissues, including lymphoid and non-lymphoid peripheral tissues. In some embodiments, the subject is immunodeficient or has lymphopenia. For the purposes of treatment, the patient is already suffering abnormally low levels of circulating lymphocytes. For the purposes of prevention, the patient may have normal levels of peripheral lymphocytes and is likely to experience lymphodepletion, e.g., as a result of a chemotherapeutic treatment.

Standards for diagnosing lymphopenia are known in the art, and can be made by any trained physician. In some embodiments, the patient has a circulating blood total lymphocyte count that is below about 600/mm$^3$. In some embodiments, the patient has a circulating blood total lymphocyte count that is less than about 2000/μL total circulating lymphocytes at birth, less than about 4500/μL total circulating lymphocytes at about age 9 months, or less than about 1000/μL total circulating lymphocytes patients older than about 9 months (children and adults). See, e.g., The Merck Manual, 18th Edition, 2006, Merck & Co.

The origins or etiology of the depletion or abnormally low can be for any reason. Lymphocytopenia has a wide range of possible causes, including viral (e.g., HIV infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. The lymphopenia may also be of unknown etiology (i.e., idiopathic lymphopenia).

The lymphocyte depletion may involve total lymphocytes (e.g., T cells, B cells, and NK cells, etc.), or may only involve a subpopulation of total lymphocytes (one or more of T cells, CD4+ T cells, CD8+ T cells, B cells, NK cells).

In some embodiments, the patient has a disease that causes depletion of peripheral circulating lymphocytes. For example, the patient may suffer from a cancer, including Hodgkin's disease and cancers of the lymphatic system, leukemia; a viral infection, including HIV or hepatitis virus. In some embodiments, the patient is receiving chemotherapy, e.g., an anticancer agent, an antiviral or antiretroviral agent, or a glucocorticoid, that causes depletion of peripheral circulating lymphocytes. Exemplary pharmacological agents that can cause lymphodepletion include without limitation vinblastine, fludarabine, aclarubicin, doxorubicin, exemestane, alefacept, alemtuzumab, chloramphenicol, pamidronate, idarubicin and cyclophosphamide.

In some embodiments, the subject may have a genetic mutation that results in a non-functional IL-15 or non-functional IL-15 receptor subunit (e.g., IL 15Rα, IL 15Rβ, or IL 15Rγ).

4. IL-15

The IL-15 for use in the invention can be any physiologically active (i.e., functional) IL-15. The IL-15 can be delivered as a polypeptide or a polynucleotide encoding IL-15. The IL-15 can be full-length or a physiologically active fragment thereof, for example, an IL-15 fragment that retains binding to IL-15Rα and/or IL-15Rβ, or an IL-15 fragment that promotes proliferation and/or maturation of T cells. In some embodiments, the delivered or expressed IL-15 polypeptide has one or more amino acids that are substituted, added or deleted, while still retaining the physiological activity of IL-15. In some embodiments, the delivered or expressed IL-15 shares at least 90%, 93%, 95%, 97%, 98%, 99% or 100% amino acid sequence identity with a wild-type IL-15, e.g., SEQ ID NO:2. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO:1.

The polynucleotide encoding IL-15 may have one or more codons altered for improved expression. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO:3. In some embodiments, the polynucleotide encoding IL-15 shares at least 96%, 97%, 98%, 99% or 100% nucleic acid sequence identity with a wild-type IL-15 coding sequence, e.g., SEQ ID NO:4. Polynucleotides encoding IL-15 which have altered codons for improved expression are described, e.g., in WO 2007/084342 and in WO 2004/059556, the entire disclosures of each of which are hereby incorporated herein by reference for all purposes.

The polynucleotide encoding IL-15 can be operably linked to polynucleotide encoding a native signal peptide sequence, e.g., the long IL-15 signal peptide sequence (LSP) or the short IL-15 signal peptide sequence (SSP). In some embodiments, the nucleic acid sequence encoding a native IL-15 signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). An example of a human GMCSF-IL-15 fusion is provided in SEQ ID NO:18. In some embodiments, the nucleic acid encoding the IL-15 is operably linked to a nucleic acid encoding an RNA export element, for example a CTE or RTEm26CTE.

Preferably, the IL-15 is administered as a heterodimer with IL-15Rα. One or both of the IL-15 and the IL-15Rα can be delivered as a polypeptide. One or both of the IL-15 and the IL-15Rα can be delivered as a polynucleotide. In one embodiment, the IL-15 and the IL-15Rα are co-administered as polypeptides. In one embodiment, an IL-15 polypeptide is co-administered with a polynucleotide encoding IL-15Rα. In one embodiment, an IL-15Rα polypeptide is co-administered with a polynucleotide encoding IL-15.

The administered IL-15Rα can be any physiologically active (i.e., functional) IL-15Rα. The IL-15Rα can be delivered as a polypeptide or a polynucleotide encoding IL-15Rα. The IL-15Rα can be full-length or a physiologically active fragment thereof, for example, an IL-15Rα fragment that retains specific binding to IL-15. Further, the IL-15Rα, e.g., a fragment that retains specific binding to IL-15 and lacks the transmembrane anchor region, can be fused to an Fc region. In some embodiments, the delivered or expressed IL-15Rα polypeptide has one or more amino acids that are substituted, added or deleted, while still retaining the physiological activity of IL-15Rα. In some embodiments, the delivered or expressed IL-15 shares at least 90%, 93%, 95%, 97%, 98%, 99% or 100% amino acid sequence identity with a wild-type IL-15Rα, e.g., SEQ ID NO:5 or SEQ ID NO:7. In some embodiments, the polynucleotide encoding IL-15 shares at least 90%, 93%, 95%, 97%, 98%, 99% or 100% nucleic acid sequence identity with a wild-type IL-15 coding sequence, e.g., SEQ ID NO:6 or SEQ ID NO:8.

The polynucleotide encoding IL-15Rα may have one or more codons altered for improved expression. In some embodiments, the polynucleotide encoding IL-15Rα shares at least 90%, 93%, 95%, 97%, 98%, 99% or 100% nucleic acid sequence identity with a wild-type IL-15Rα coding sequence, e.g., SEQ ID NO:9 or SEQ ID NO:11. Polynucleotides encoding IL-15Rα which have altered codons for improved expression are described, e.g., in WO 2007/084342.

The polynucleotide encoding IL-15Rα can be operably linked to polynucleotide encoding a native signal peptide sequence. In some embodiments, the nucleic acid sequence encoding a native IL-15Rα signal peptide is replaced with a nucleic acid sequence encoding a signal peptide from a heterologous protein. The heterologous protein can be, for example, from tissue plasminogen activator (tPA), growth hormone, granulocyte-macrophage colony stimulating factor (GM-CSF) or an immunoglobulin (e.g., IgE). In some embodiments, the nucleic acid encoding the IL-15Rα is operably linked to a nucleic acid encoding an RNA export element, for example a CTE or RTEm26CTE.

In some embodiments, the IL-15Rα can be in the form of an Fc fusion protein. Examples of sIL-15Rα polypeptide sequences are shown in SEQ ID NO:17 and SEQ ID NO:20. Typically, such proteins are secreted and can be found soluble in the plasma, or they can be associated with the surface of cells expressing the Fc receptor for the Fc region of the fusion protein. Different fragments of IL-15Rα can be fused to the Fc region. Two examples of functional fusions are provided as SEQ ID NO:17 and SEQ ID NO:20, containing 205 or 200 amino acids within the IL-15Rα region. In some embodiments, the IL-15Rα region of the fusion protein can be released by proteolytic cleavage. In some embodiments, I-L15Rα functional region of the protein is linked to a polypeptide that is able to bind specific cell types via surface receptors. In some embodiments, the IL15-Rα Fc fusion protein shares at least 95%, 96%, 97%, 98%, 99% or 100% amino acid sequence identity with a polypeptide selected from the group consisting of SEQ ID NO:17 and SEQ ID NO:20.

In some embodiments, a polynucleotide encoding IL-15 is co-administered with a polynucleotide encoding IL-15Rα. The polynucleotide encoding IL-15 and the polynucleotide encoding IL-15Rα can be administered on the same vector or on separate vectors. Preferably the polynucleotide encoding IL-15 is co-administered with a polynucleotide encoding IL-15Rα are on the same vector. An example of a plasmid that encodes an IL-15Rα-Fc fusion having a polypeptide sequence of SEQ ID NO:17 and a human GM-CSF signal peptide-IL-15 of SEQ ID NO:18 is provided in SEQ ID NO:16. A second example of a plasmid that encodes an IL-15Rα-Fc fusion having a polypeptide sequence of SEQ ID NO:20 and a human GM-CSF signal peptide-IL-15 of SEQ ID NO:18 is provided in SEQ ID NO:19. In some embodiments, the administered vector shares at least 95%, 97%, 98%, 99% or 100% nucleic acid sequence identity with a plasmid vector selected from the group consisting of SEQ ID NO:13, SEQ ID NO:14, SEQ ID NO:15, SEQ ID NO:16, and SEQ ID NO:19.

It is understood by one skilled in the art that expression vectors, promoters, polyadenylation signals, and secretory peptides alternatives to those in the example sequences provided herein can be used for the expression of the optimized IL-15 and IL-15 Receptor alpha.

For the purposes of the present methods, the IL-15 is not being used as an adjuvant to enhance the immune response against a particular antigen. Therefore, in the present methods, the IL-15 is administered without an antigen. Stated another way, the IL-15 is not co-administered with an antigen.

The IL-15 (and the IL-15Rα) are administered at a dose sufficient to achieve supraphysiological levels of IL-15 systemically or in the target tissue, e.g., thymus, for the desired time period. The desired time period can be hours, days, weeks, or longer if necessary. In some embodiments, supraphysiological levels of IL-15 are sustained throughout the duration of treatment or until a desired therapeutic endpoint is achieved, e.g., the repopulation of peripheral tissues with lymphocytes. In some embodiments, the IL-15 is administered one time, as a bolus. In some embodiments, the IL-15 is administered two or more times. When administered multiple times, the IL-15 can be administered daily, weekly, bi-weekly, monthly, or as needed to sustain supraphysiological levels of IL-15 systemically or in the target tissue.

In embodiments where the IL-15 (and the IL-15Rα) are administered as a polypeptide, typical dosages can range from about 0.1 mg/kg body weight up to and including about 0.5 mg/kg body weight. In some embodiments, the dose of polypeptide is about 0.01, 0.02, 0.05, 0.08, 0.1, 0.2, 0.3, 0.4, 0.5 mg/kg body weight.

In embodiments where the IL-15 (and the IL-15Rα) are administered as a polynucleotide, dosages are sufficient to achieve plasma levels of IL-15 of about 1 to 1000 ng/ml, for example, plasma levels of IL-15 of about 10 to 1000 ng/ml. Such a range of plasma concentrations can be achieved, e.g., after intramuscular electroporation of about 0.1 mg IL-15/IL-15sRα expressing DNA plasmid per kg body weight. In some embodiments, the dose of nucleic acid is about 0.02, 0.05, 0.1, 0.2, 0.5 mg/kg body weight.

The IL-15 can be administered by a route appropriate to effect systemic supraphysiological levels of IL-15 or supraphysiological levels of IL-15 in the target tissue, e.g., thymus. When co-administered with IL-15Rα, the IL-15 and the IL-15Rα can be administered via the same or different routes. In some embodiments, the IL-15 (and the IL-15Rα) are administered systemically, including without limitation, enterally (i.e., orally) or parenterally, e.g., intravenously, intramuscularly, subcutaneously, intradermally, intranasally, or inhalationally. In some embodiments, the IL-15 (and the IL-15Rα) are administered locally, for example, intrathymically or directly into the bone marrow.

For treatment of lymphopenia, systemic administration of IL-15 promotes and accelerates the repopulation of peripheral lymphocyte populations. After administration of IL-15, the peripherally circulating lymphocytes or lymphocyte subpopulations can be at least 80%, 85%, 90% or 95% of levels considered to be normal in a healthy individual. In some embodiments, the lymphocytes or lymphocyte subpopulations are completely repopulated to normal levels. In some embodiments, the repopulation of lymphocytes is days or weeks faster in an individual who received administration of IL-15 in comparison to an individual who did not receive administration of IL-15.

Systemic administration of IL-15 also prevents, reduces or inhibits lymphocyte depletion in peripheral circulation, e.g., caused by chemotherapy or radiation therapy. After administration of IL-15, the peripherally circulating lymphocytes or lymphocyte subpopulations can be maintained at levels of at least 70%, 75%, 80%, 85%, 90% or 95% of normal levels. In some embodiments, the lymphocytes or lymphocyte subpopulations are maintained at normal levels.

In some embodiments, the IL-15 is co-administered with a chemotherapeutic agent that causes or may cause lymphopenia or lymphocyte depletion in peripheral tissues. The chemotherapeutic agent may be an anticancer agent or an antiviral agent. In some embodiments, the IL-15 is administered after a course of treatment with a chemotherapeutic agent that causes or may cause lymphopenia or lymphocyte depletion in peripheral tissues. In some embodiments, the IL-15 is administered prior to, during or after a course of radiation therapy.

EXAMPLES

The following examples are offered to illustrate, but not to limit the claimed invention.

Example 1

Figure 2:
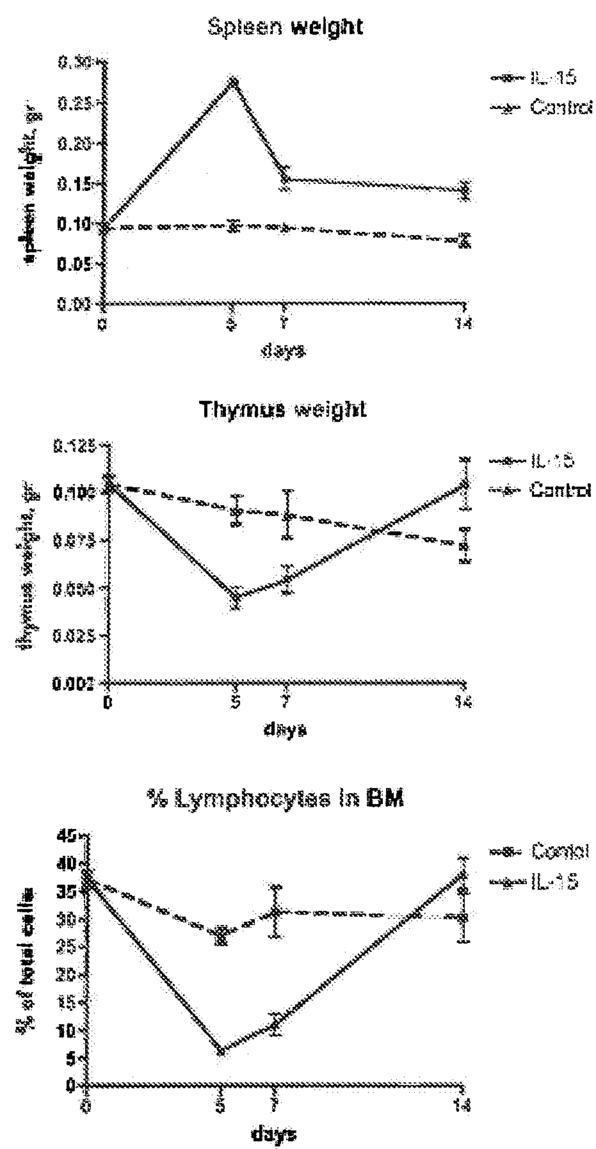
FIG. 2 illustrates the effects of systemic co-administration of polynucleotides expressing IL-15 and IL-15Rα on spleen weight (top panel), thymus weight (middle panel) and percentage of lymphocytes in the bone marrow (bottom panel).
Figure 3:
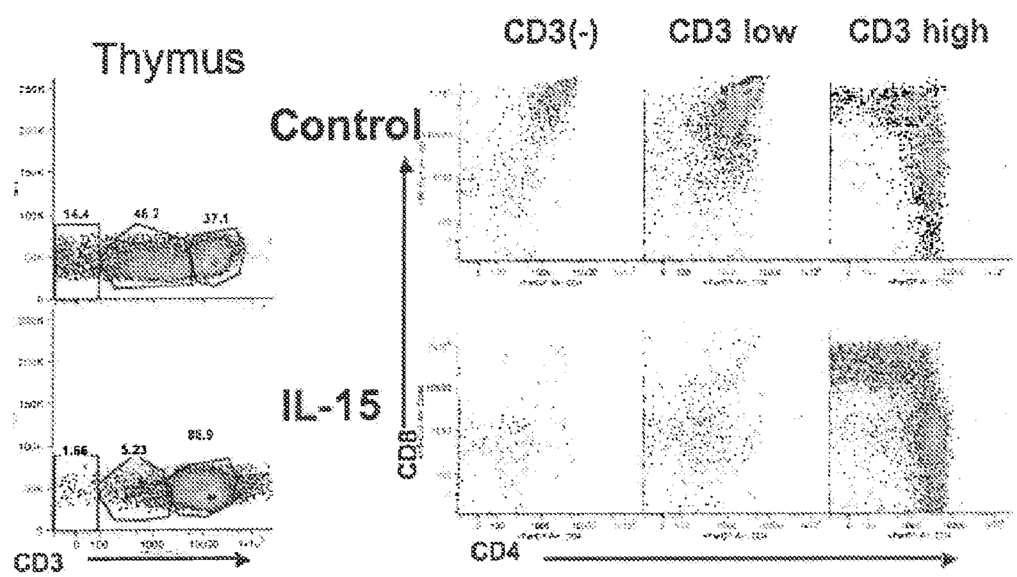
FIG. 3 illustrates the effects of systemic co-administration of polynucleotides expressing IL-15 and IL-15Rα on T cell maturation in the thymus. Double positive CD4+CD8+ T cells are decreased with a concomitant increase in CD3high single positive T cells (i.e., CD4+ or CD8+ T cells).
Figure 4:
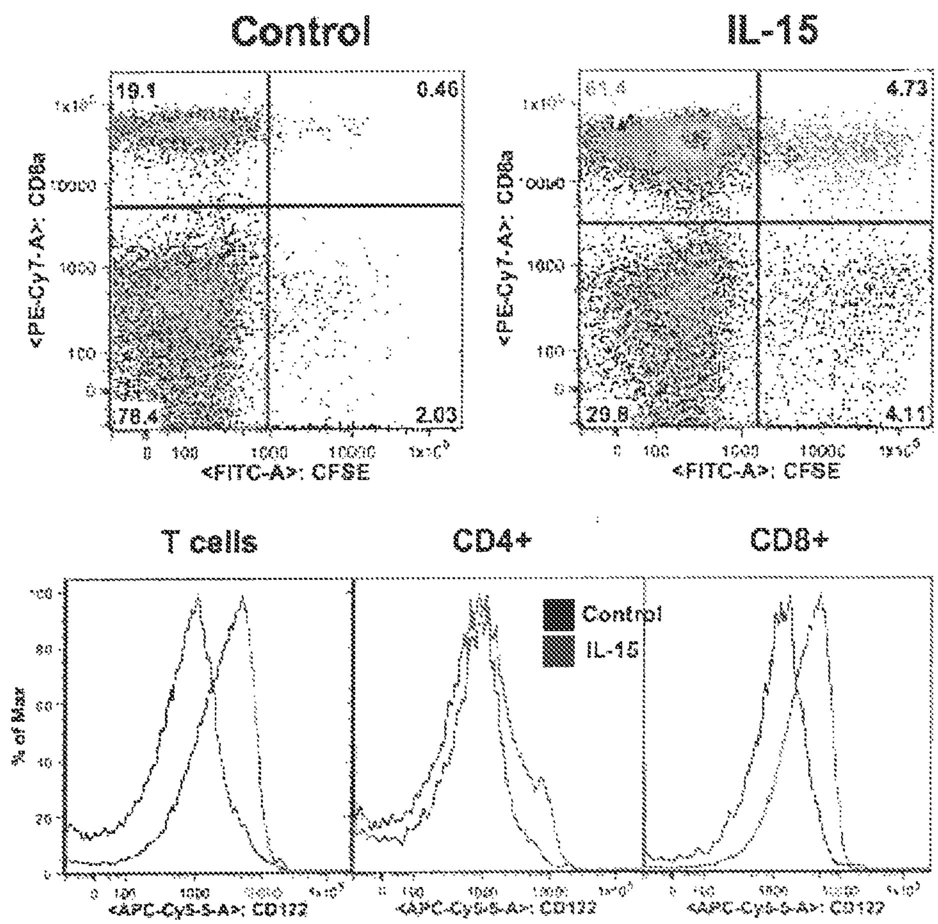
FIG. 4 illustrates the migration of dividing carboxyfluorescein succinimidyl ester ("CFSE")-loaded thymocytes to the lung in IL-15-treated and untreated control mice (upper panels). The lower panels show increased expression of CD122 (IL-2Rβ/IL-15Rβ) on lymphocytes, e.g., total T cells and CD+ T cells, in the lung.

Systemic Administration of IL-15 Promotes Maturation of T Cells in the Thymus and the Migration of T Cells to Peripheral Tissues IL-15/IL-15Rα DNA was expressed systemically and locally at various levels in either normal or IL-15 knockout (KO) mice to further understand IL-15 biology. See, Bergamaschi, et al., (2008) *J Biol Chem* 283:4189-4199. Supraphysiologic levels of IL-15/IL-15Rα in normal mice have rapid and profound effects in many tissues. There is a rapid and reversible increase in the size of spleen, whereas the thymus becomes smaller and bone marrow lymphocyte numbers decrease (FIG. 2). We have previously shown that spleen and lymph node size increase is proportional to the amount of IL-15 in the plasma. See, Bergamaschi, et al., (2008) *J Biol Chem* 283:4189-4199. The kinetics and composition of lymphocytes in many tissues were studied using 10 parameter flow cytometry, as well as adoptive transfer of cells and in vivo labeling. Our results underscore the strong effects of IL-15 at all steps of lymphocyte development, as also suggested by many investigators. Reviewed in, e.g., Boyman, et al., (2007) *Curr Opin Immunol* 19:320-326: Sprent, et al., (2008) *Immunol Cell Biol* 86:312-319; Sprent and Surh, (2003) *Immunol Lett* 85:145-149; Surh, et al., (2006) *Immunol Rev* 211:154-163; Surh and Sprent, (2005) *Semin Immunol* 17:183-191; and Surh and Sprent, (2008) *Immunity* 29:848-862. However, prior to the present invention, the effects of IL-15 in the thymus have not been elucidated. Our results indicate that IL-15 stimulates the maturation of CD4+ CD8+ double positive thymocytes into CD3high single positive T cells (FIG. 3) and accelerates their rapid migration to the periphery (FIG. 4). Seven days after in situ labeling of thymocytes, IL-15/IL-15Rα promoted their migration to the lung. In the presence of IL-15/IL-15Rα the lymphocytes in the lung have higher levels of IL-2/IL-15Rα (CD122, see, FIG. 4, bottom) indicating that they are activated. These results are consistent with the notion that IL-15 promotes not only accelerated exit from the thymus, but also the migration to peripheral tissues and the activation of these lymphocytes.

Our results also show that, in addition to NK and memory CD8+ T cells that are profoundly affected, as expected, all lymphocytes including naïve and memory CD4 and CD8 cells, and B lymphocytes are also affected to either divide, migrate or be activated. This is in agreement with the widespread (but not universal) expression of the IL-2/IL-15 betagamma receptor. The hierarchy of responsiveness of the lymphocyte subsets to IL-15 reflects the levels of CD122 (IL-2Rbeta) on their surface. See, Bergamaschi, et al., (2008) *J Biol Chem* 283:4189-4199.

Figure 5:
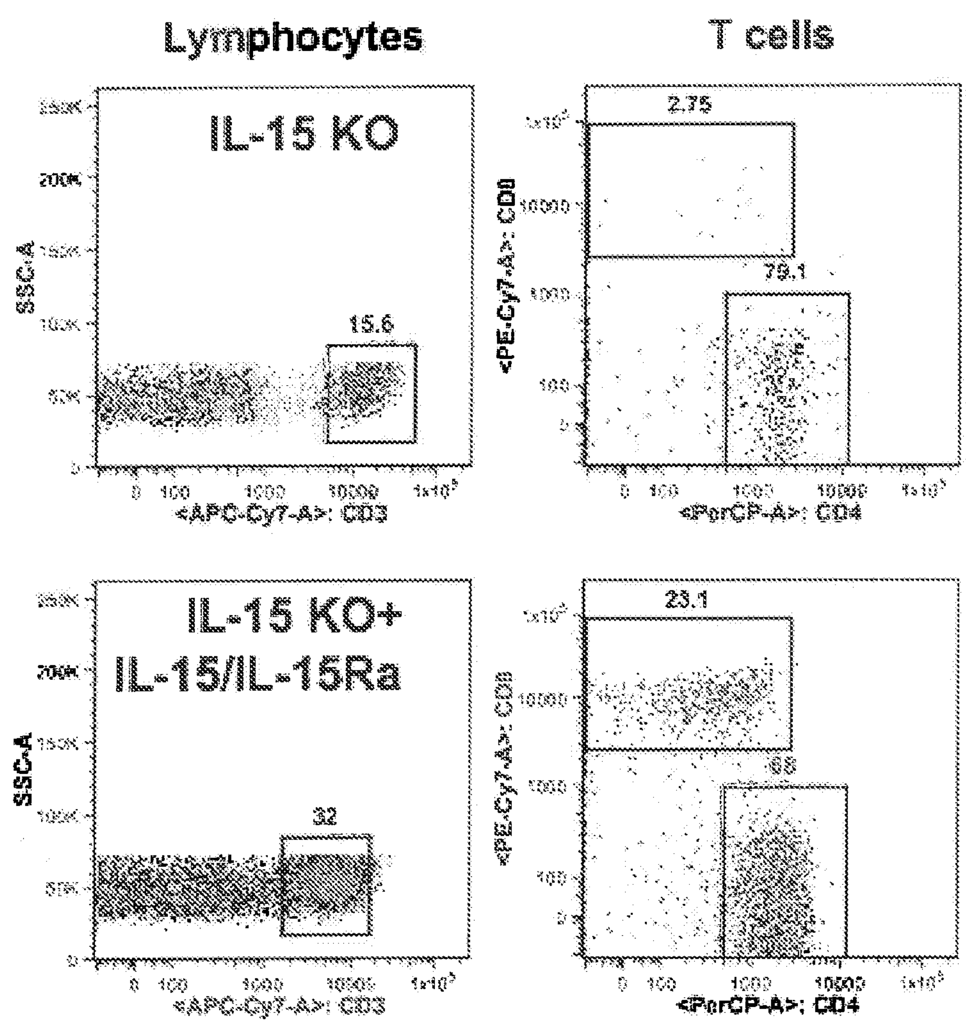
FIG. 5 illustrates lymphocyte reconstitution in lung tissue of IL-15 knock-out (KO) mice treated with plasmid DNA encoding IL-15/IL-15Rα compared to untreated control KO mice.
Figure 6:
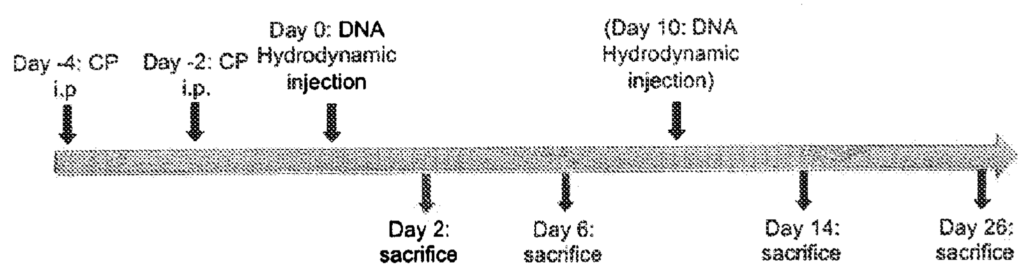
FIG. 6 provides a schematic of the time course of a lymphodepletion experiment.

Our observations are further supported by experiments performed in an IL-15 KO model, to correct the lymphocyte defects by administering plasmid DNA encoding IL-15/IL-15Rα heterodimer. IL-15 KO mice are characterized by a decrease in total T cell count that preferentially affects CD8+ T cells, which are almost completely absent in peripheral tissues. We show that IL-15/IL-15Rα is able to repopulate non-lymphoid organs, such as lungs, with both mature CD4 and CD8 T lymphocytes. The increase in CD4 T cells upon IL-15/IL-15Rα treatment is 10-fold, while the increase in the CD8+ population is significantly greater, reaching 100-fold (FIG. 5). These results underscore the feasibility of using IL-15/IL-15Rα DNA to correct defects associated with lymphopenia (e.g., caused by total absence of IL-15 or of another etiology). Analysis of lymphocytes migrating in different organs in the presence of IL-15 suggests that many acquire rapidly a memory phenotype in the absence of antigen recognition and that IL-15 promotes re-entry of some lymphocytes into the thymus. The issue of lymphocyte re-entry in the thymus is controversial, and the study of IL-15 effects may contribute to the understanding of this phenomenon. See, Sprent and Surh (2009) *Immunol Cell Biol* 87:46-49; Bosco, et al., (2009) *Immunol Cell Biol* 87:50-57; Agus, et al., (1991) *J Exp Med* 173:1039-1046. Our preliminary data indicate that transfer of CFSE loaded thymocytes into normal mice results in homing into the thymus only in animals receiving IL-15.

We have found that IL-15 decreases the frequency of apoptotic thymocytes, mainly by promoting their terminal differentiation into mature single positive T cells. Our results after intrathymic injection of CFSE indicate that IL-15 increases thymic output, as reflected by the higher frequency of fully mature CFSE labeled T cells in the spleen and lung of IL-15 treated mice.

We have further observed that the enlarged spleen size upon IL-15 treatment is partially due to increased frequency of B lymphocytes, either by local proliferation, B cell migration from other compartments, or both. In addition, during in vivo experiments with adoptive transferred CFSE-labeled splenocytes we observed IL-15-induced proliferation of both CD4 naïve and memory T cells. In contrast to CD8+ T cells, which almost universally proliferate in the presence of IL-15, the CD4+ T cell responses appear to be restricted to a subset of cells.

Example 2

Correction of Cyclophosphamide-Induced Lymphopenia by IL-15/IL-15Rα DNA Administration Summary The present example shows the reversal of cyclophosphamide-induced lymphopenia in normal young mice by systemic administration of IL-15. One or two high doses of IL-15 were administered two (2) days (or two (2) and twelve (12) days) after cyclophosphamide by hydrodynamic DNA injection. The results show that mice recover faster from lymphopenia after IL-15 administration in comparison to control mice with cyclophosphamide-induced lymphopenia that did not receive IL-15. Lymphocytes recovered faster in peripheral tissues after IL-15 administration. NK cells were the first to recover, whereas T cells recovered in approximately one month. In the course of these studies, we discovered that two administrations of IL-15 improved T cell recovery over a single administration of IL-15. In addition, low and sustained levels of IL-15 provides for a more efficient repopulation of lymphocytes to the peripheral tissues in comparison to a single high dose. These results demonstrate that IL-15 is useful in treating and/or preventing lymphopenia.

Methods

Cyclophosphamide Administration

Six-to-eight week old female Balb/c mice were obtained from Charles River Laboratory (Frederick, Md.). Cyclophosphamide (Sigma) was dissolved in pyrogen-free saline and injected intra-peritoneally (i.p.) at a dose of 200 mg/kg of body weight. Two treatments with cyclophosphamide were performed at day −4 and −2.

DNA Injection

On day 0, hydrodynamic injection of either a control vector or IL-15 and IL-15Rα expression plasmid into cyclophopshamide treated mice was performed. Empty vector DNA was also administered to the cyclophopshamide-untreated mice, as control. Briefly, 0.2 μg to 2 μg of DNA in 1.6 ml of sterile 0.9% NaCl were injected into mice through the tail vein within 7 seconds using a 27.5 gauge needle. Highly purified, endotoxin-free DNA plasmids were produced using Qiagen EndoFree Giga kit (Qiagen, Hilden).

Lymphocyte Analysis

Mice were sacrificed at different time points (days 2-26) after DNA injection and serum, bone marrow, thymus, spleen, liver and lungs were collected for analysis.

For bone marrow lymphocyte isolation, left and right femurs were collected and centrifuged at 13,000 for 5 min, re-suspended, and centrifuged again (total of 3 times). Collected cells were re-suspended in RPMI containing 10% fetal calf serum and viable cells were counted using Acridine Orange (Molecular Probes)/Ethidium Bromide (Fisher) dye.

For splenocyte or thymocyte isolation, spleens or thymi were gently squeezed through a 100 μm Cell Strainer (Thomas) and washed in RPMI (Gibco) to remove any remaining lymphocytes from the organ stroma. After centrifugation, the cells were re-suspended in RPMI containing 10% fetal calf serum and counted.

To isolate lymphocytes from livers or lungs, the tissues were minced and incubated with 200 U/ml of collagenase (Sigma) and 30 U/ml of DNase (Roche) for 1 h at 37° C., then single cells were collected, centrifuged and re-suspended in complete RPMI with 10% fetal calf serum.

For phenotyping, the cells were incubated with the following mix of directly conjugated anti-mouse antibodies (BD Pharmingen): CD3-APC, CD4-PerCP, CD8-PECy7, CD44-APC, CD49b-FITC, CD19-PE, CD62L-PE. Labeled cell samples were analyzed by flow cytometry using an LSR II Flow Cytometer (BD) and were analyzed using FlowJo software (Tree Star, San Carlos, Calif.).

Lymphocytes of the different group of mice were counted and compared. Statistical analyses were performed using the Prism Software Program. Comparisons of two groups were performed by non-parametric Mann-Whitney t test. Confidence intervals were 0.05, and all p values were two-tailed.

Results

Two injections of cyclophosphamide at days −4 and −2 were used to generate lymphodepleted mice. At day 0 (and also, for some mice at day 10) IL-15/15Rα DNA expression vector was injected in the tail vein, which generated high systemic levels of bioactive IL-15/15Rα, as published (Bergamaschi, et al., *J Biol Chem.* (2008) 283(7):4189-99). The biological effects after injection of IL-15/15Rα DNA were compared to the injection of a non-producing DNA (vector BV) as negative control in cyclophosphamide-treated animals.

Different tissues, including lung, liver, spleen, thymus and bone marrow, were extracted from mice sacrificed at days 2-26 from DNA injection and the lymphocyte populations were studied.

Figure 7:
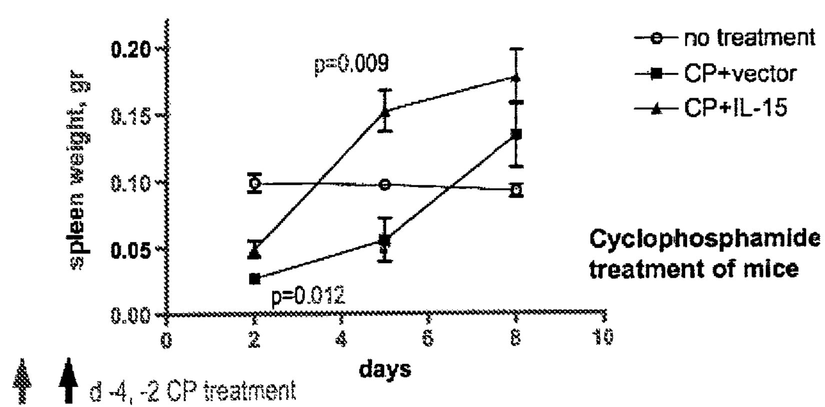
FIG. 7 illustrates spleen weight over time after cyclophosphamide (Cyp) and Cyp+IL-15/IL-15Rα administration.

Cyclophosphamide treatment had strong effects on lymphocytes, as reflected in the increased spleen weight of treated animals (FIG. 7). Four animals per time point were sacrificed and the spleen weight was monitored. The two groups treated with cyclophosphamide (CP+vector, treated with a non-producing DNA vector; CP+IL-15) had a smaller spleen at day 2 after DNA treatment (4 days after cyclophosphamide). At this early point and also at day 5 the IL-15 treated animals showed a statistically significant difference in spleen size, indicating accelerated recovery by IL-15.

Lung

We also analyzed lymphocyte numbers and subsets in different tissues to evaluate the effects of IL-15/15Rα administration. These experiments were performed after one or two IL-15/15Rα DNA administrations (at days 0 and 10).

Lung lymphocytes were evaluated in order to determine the effects of IL-15/15Rα on a peripheral site, where lymphocytes need to function. IL-15 is known to affect strongly CD8+ T cells and NK cells. High levels of IL-15 (achieved with two injections of 2 μg DNA at days 0 and 10), favors lymphocyte recovery in the lung after Cyp treatment.

Effects on Natural Killer (NK) Cells:

Mice were treated at days −4 and −2 and injected with DNA at day 0. Two groups of mice were injected with either BV negative control DNA or with IL-15/IL-15Rα DNA. The IL-15/IL-15Rα-treated animals had a trend for higher NK numbers for all time points. At day 14, comparison of the group receiving empty vector with the group of 2×IL-15/IL-15Rα administration (DNA injections at days 0 and 10) showed that IL-15/15Rα significantly increased lung NK cell recovery ($p=0.03$).

Figure 8:
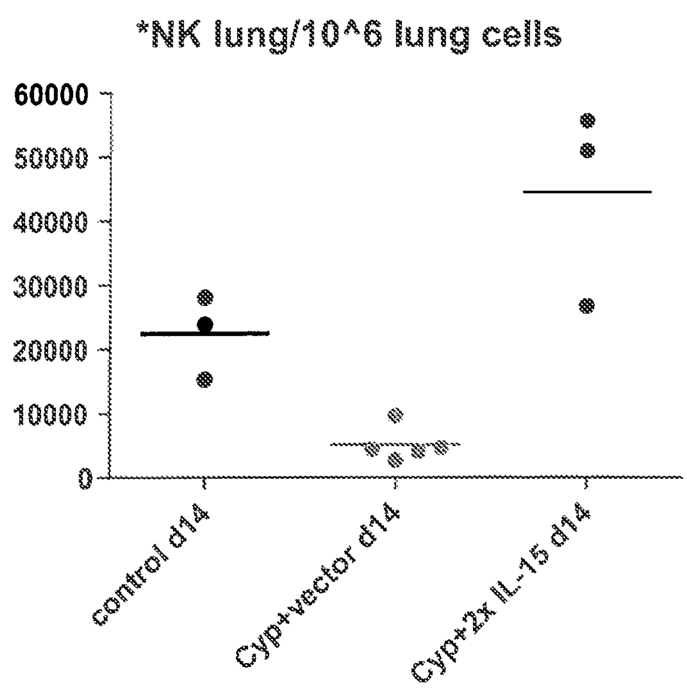
FIG. 8 illustrates the increase in lung NK cells after Cyp administration.

The lymphocyte population that recovers first is the NK cells. In our experiments after cyclophosphamide treatment the NK cells recovered partially in the absence of any other intervention. IL-15/15Rα administration accelerated this recovery. The best recovery was observed after two IL-15 injections at days 0 and 10. Examination at day 14 showed a significant increase in NK by IL-15 compared to Cyp ($p=0.03$). See, FIG. 8.

Effects on Lung T Cells

Figure 9:
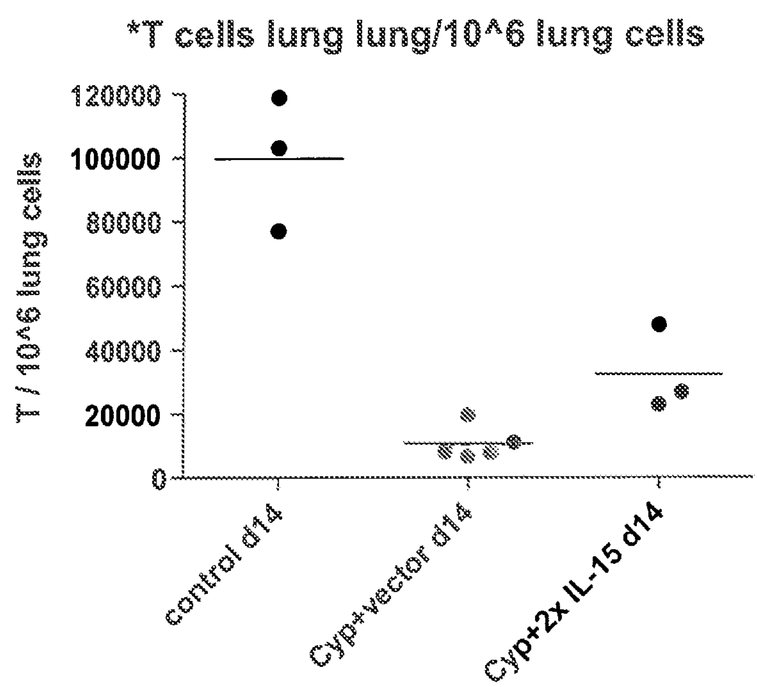
FIG. 9 illustrates the increase in lung T cells in the presence of IL-15/IL-15Rα.

In contrast to NK cells, lung T cells do not recover as fast. The mice were treated and analyzed as above. Lung T cells were enumerated at day 14 after the first DNA injection. It was found that total T cells increased at day 14 after two IL-15/Rα administrations at days 0 and 10, compared to the Cyp treated animals. See, FIG. 9.

Figure 10:
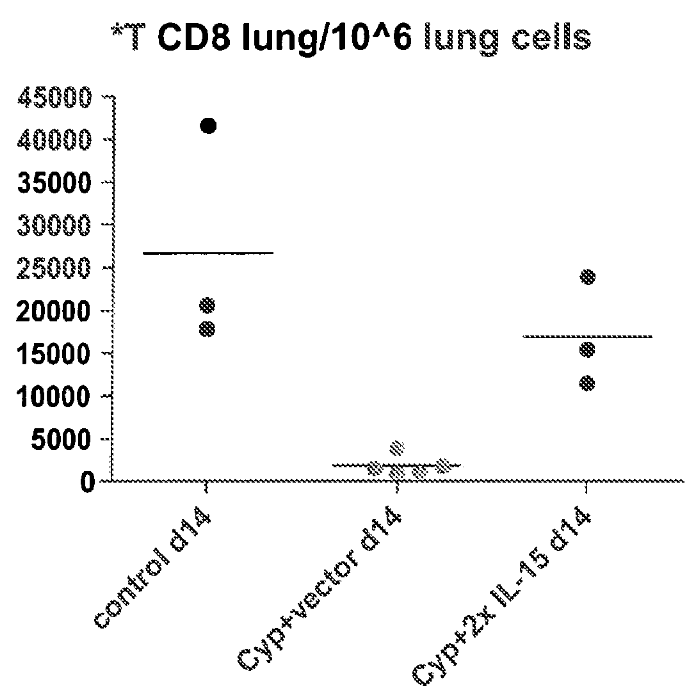
FIG. 10 illustrates that CD8+ T cells partially recover after IL-15/IL-15Rα administration.
Figure 11:
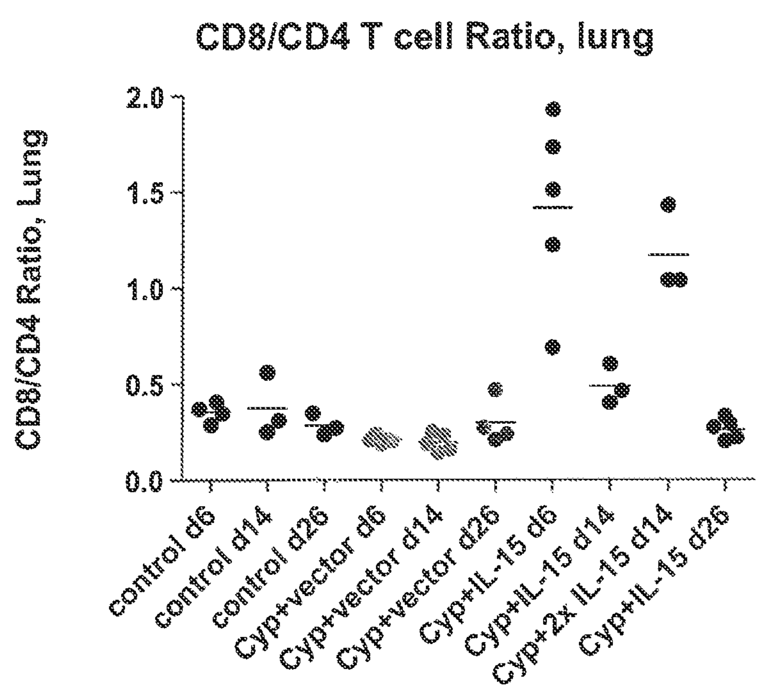
FIG. 11 illustrates the increase in lung CD8+ T cells in the presence of IL-15/IL-15Rα as reflected in the change of the ratio of CD8+ to CD4+ T cells after IL-15 administration.

The lung T cells were also distinguished according to expression of CD4 or CD8 and compared among different groups of mice. It was found that the CD8+ T cells increased preferentially after IL-15/15Rα administration at day 14 ($p=0.0357$). Moreover, at days 6 and 14 the CD8/CD4 ratio was increased, demonstrating the preferential stimulation of CD8+ T cells by IL-15. The ratio returns to normal by day 26, in the group that received IL-15/15Rα. See, FIGS. 10 and 11.

Spleen

Figure 12:
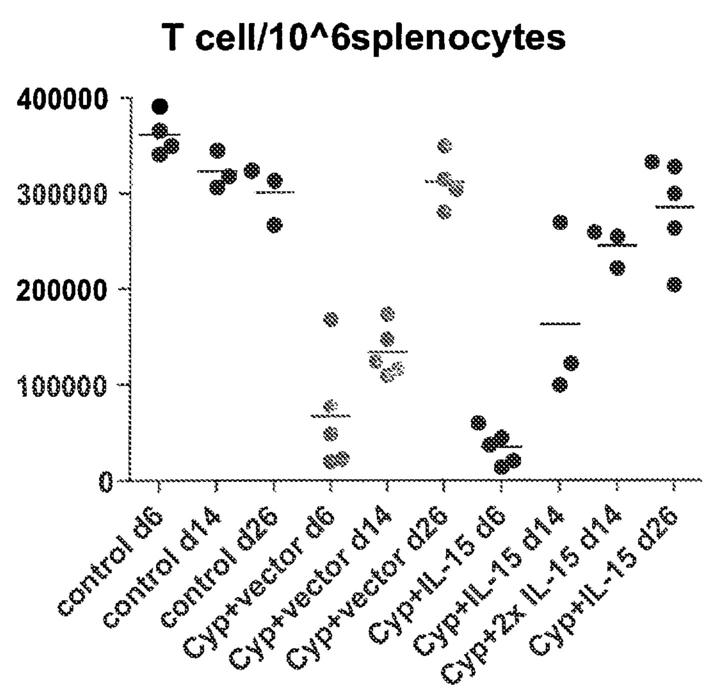
FIG. 12 illustrates a T cell analysis in the spleen after Cyp and IL-15/IL-15Rα administration.

In the spleen, we also found that T cells recover faster after two injections of IL-15/15Rα ($p=0.0357$). Similar to the results in the lung, two doses of IL-15/15Rα (days 0 and 10) were able to increase spleen lymphocytes after Cyp ($p=0.03$). See, FIG. 12.

Bone Marrow

Figure 13:
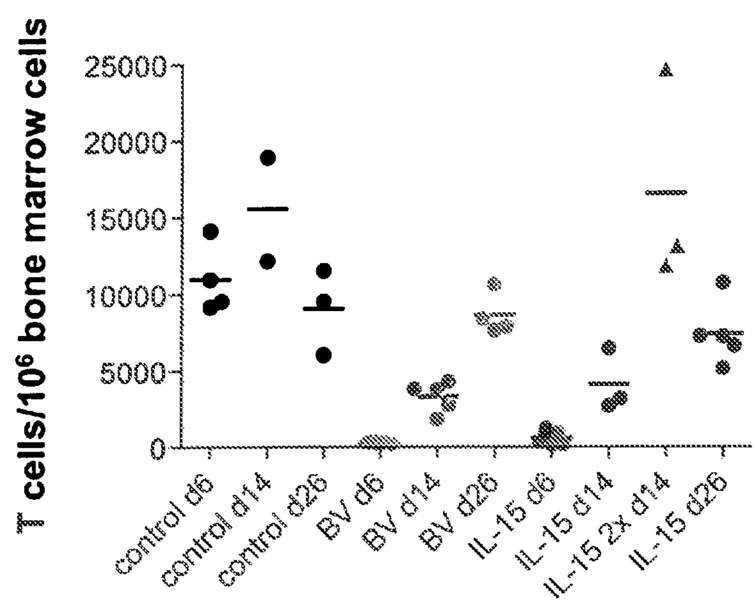
FIG. 13 illustrates the full recovery of bone marrow T cells after IL-15/IL-15Rα administration.

Sustained high level of IL-15 (achieved with two injections of 2 μg DNA at days 0 and 10) resulted in T cell recovery in bone marrow by day 14 after the first DNA injection (FIG. 13). IL-15 affected both CD4 and CD8 compartments. Treatment with two administrations of IL-15/15Rα resulted in high levels of bone marrow T cells at day 14 compared to Cyp treated animals.

Example 3

Therapeutic Effects of IL-15 on Lymphopenia in Two Different Mouse Strains

This example also employed Black6 mice to analyze therapeutic effects of various forms of IL-15 on lymphopenia. Two different mouse strains, BALB/c and Black6, were used in these experiments. Both strains showed accelerated lymphocyte reconstitution upon treatment with IL-15/IL-15Rα.

Treatment of Lymphoablated Mice with IL-15 DNA

Figure 14:
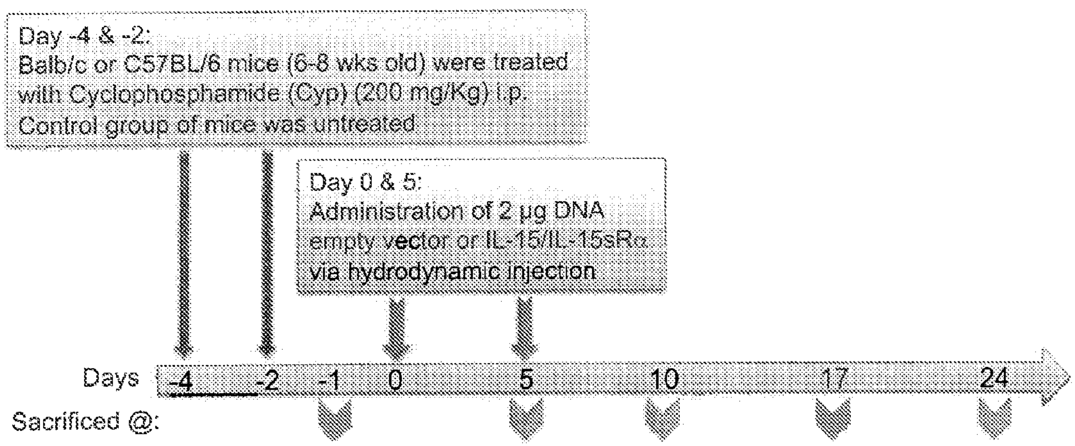
FIG. 14 illustrates the IL-15/IL-15Rα treatment protocol for lymphopenic mice used in Example 3.

Female Balb/c or Black6 mice 6-8 weeks in age were treated intra-peritoneally with a dose of 200 mg/kg of body weight of cyclophosphamide (CYP, FIG. 14). Two injections of CYP were performed at day −4 and day −2. At day 0 and day 5, hydrodynamic injection of either a control DNA or DNA expressing IL-15/IL-15sRα soluble molecule was performed. Control vector was also delivered in CYP-untreated mice as control. Mice were sacrificed at different time points: day −1 to assess the CYP-induced lymphoablation and day 5, 10, 17 and 24 to follow immune reconstitution in presence or absence of exogenous IL-15. Different tissues (spleen, thymus, bone marrow, lung and liver) were harvested and analyzed for the presence of different lymphocyte subsets. Analysis was performed by flow cytometry after staining the cells with fluorescent-labeled antibodies.

For flow analysis, isolated cells were incubated with the following directly conjugated anti-mouse antibodies (BD Pharmingen) in appropriate combinations according to the objectives of the experiment: CD3-APC or CD3-APC-Cy7, CD4-PerCp, CD8-Pacific Blue, CD44-APC, CD62L-PE, CD19-APC-Cy7 or CD19-PeCy7, CD49b-FITC, CD25-APC-Cy7, CD122-PE. T cells were defined as $CD3^+$ cells in the lymphocyte gate; NK cells were defined as $CD3^-CD49b^+$ cells.

For identification of Treg population (T $CD4^+CD25^+$ $FoxP3^+$ cells), the cells were fixed and permeabilized (eBioscience), and incubated with anti-mouse FoxP3-PeCy7 antibody (eBioscience). T effector cells were defined as $CD3^+$ $ToxP3^-$ lymphocytes. Therefore, the term "Teffector" as used in here refers to all T cells except Treg.

Figure 15:
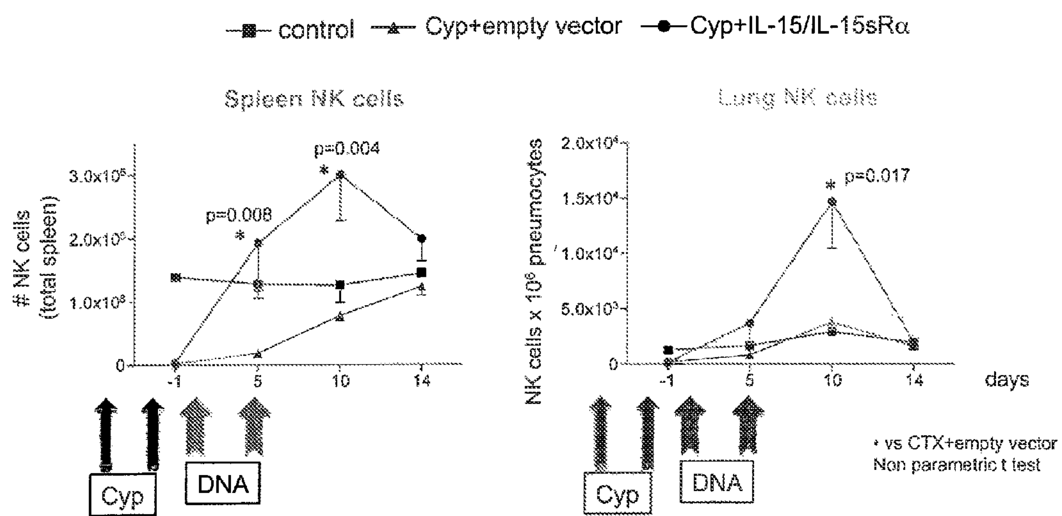
FIG. 15 illustrates that a single administration of IL-15/IL-15sRα-encoding DNA is sufficient for the complete recovery of NK cells in spleen and lung 5 days after DNA injection.

FIG. 15 shows the reconstitution of NK cell compartment in spleen and lung after CYP treatment. CYP-untreated mice were used as baseline control (squares). Two injections of CYP resulted in a drastic reduction of the absolute number of NK cells in both spleen and lung (day −1). NK cells spontaneously recover between day 10 and day 14 days after control DNA injection (triangles). One single administration of IL-15/IL-15sRα DNA was able to promote a full recovery of NK within 5 days after DNA injection. The second IL-15/IL-15sRα expressing DNA injection resulted in an even further expansion of NK cells in both spleen and lung (circles).

Figure 16:
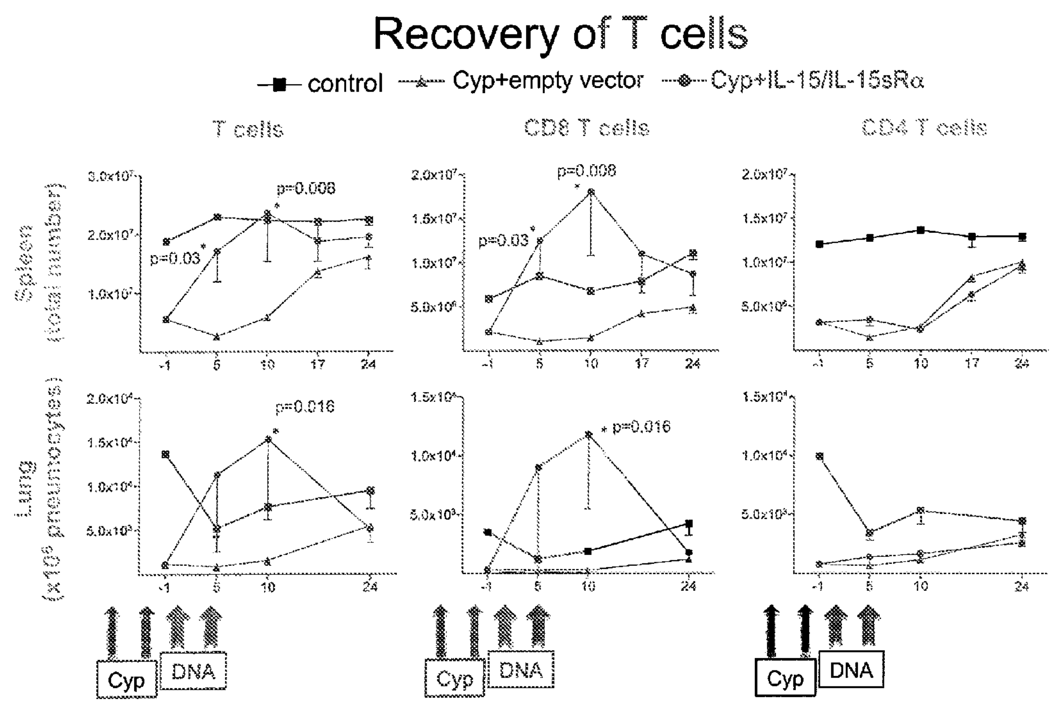
FIG. 16 illustrates that IL-15/IL-15sRααadministration promotes the recovery of CD8 T cells within 10 days after treatment, without significantly affecting the recovery of CD4 T cells.

FIG. 16 shows the reconstitution of T cell compartment in spleen and lung after CYP treatment. CYP-untreated mice were used as baseline control (squares). Two injections of CYP resulted in a 4 fold reduction in the level of splenic T cells and in 10 fold reduction in the level of T cells residing in the lung (day −1). The spontaneous recovery of T cells appeared to be slower in comparison with the recovery of NK cells and was still incomplete at day 24 after control DNA injection. The kinetics of spontaneous recovery of T CD8 and T CD4 was similar in both spleen and lung (triangles). Two injections of DNA expressing IL-15/IL-15sRα were able to fully reconstitute the T cell numbers within 10 days after DNA administration in both spleen and lung. IL-15 promoted mainly the expansion of T CD8 cells that reached normal level at day 5 after DNA injection and were boosted over normal level at day 10 after DNA injection. IL-15 did not significantly affect the recovery of T CD4 and B cells.

Figure 17:
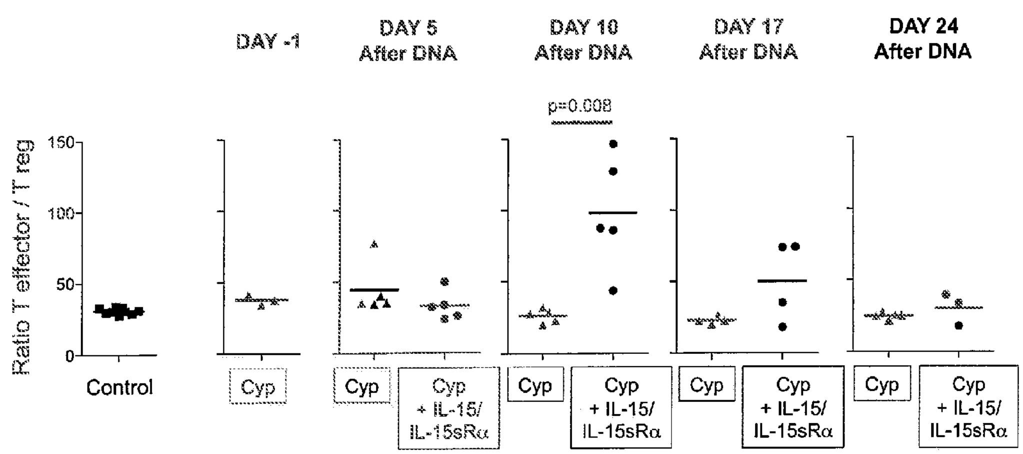
FIG. 17 illustrates that high levels of circulating IL-15/IL-15sRα promote a transient increase in the Teffector/Treg ratio after lymphoablation.

In addition, T cells recovering in the presence of high level of IL-15/IL-15sRα show increased T effector (Teff)/T regulatory (Treg) ratio and increased ability to secrete IFNgamma and greater degranulation after in vitro stimulation. FIG. 17 is an analysis of the Teff/Treg ratio after CYP treatment for lymphodepletion and during the recovery phase. The Teff/Treg ratio increased significantly at day 10 after IL-15/15sRα DNA injection.

Example 4

DNA Delivery for IL-15 to Treat Lymphopenia

In these examples, three preferred DNA vector combinations are evaluated for the therapeutic delivery of IL-15 to treat lymphopenia:

1 Co-delivery in the same cells, using preferably optimized expression plasmids expressing IL-15 and essentially full-length IL-15Rα, such as SEQ ID NO:13 and SEQ ID NO:14.
2 Co-delivery in the same cells, using preferably optimized expression plasmids expressing IL-15 and soluble (s) IL-15Rα, such as SEQ ID NO:15.
3 Co-delivery in the same cells, using preferably optimized expression plasmids expressing IL-15 and IL-15Rα fusions to the constant region of an immunoglobulin molecule (Fc) such as SEQ ID NO:16 and SEQ ID NO:19. The construction of Fc fusion proteins is known in the art. Such constructs have been used in in vivo experiments in mice to show that IL-15 and IL15Rα-Fc fusion heterodimers are active in vivo.

Delivery of IL-15/IL-15Rα heterodimer by approach (1) above leads to expression of both plasma membrane-bound and secreted IL-15/IL-15Rα. Delivery by approach (2) leads to exclusively secreted IL-15/IL-15Rα heterodimer. Delivery by approach (3) leads to a secreted bioactive heterodimer, which is then bound to cells expressing the Fc Ab receptor on their surface. These cells can present the IL-15/IL-15RαFc heterodimer to neighboring cells, resulting in activation.

Figure 18:
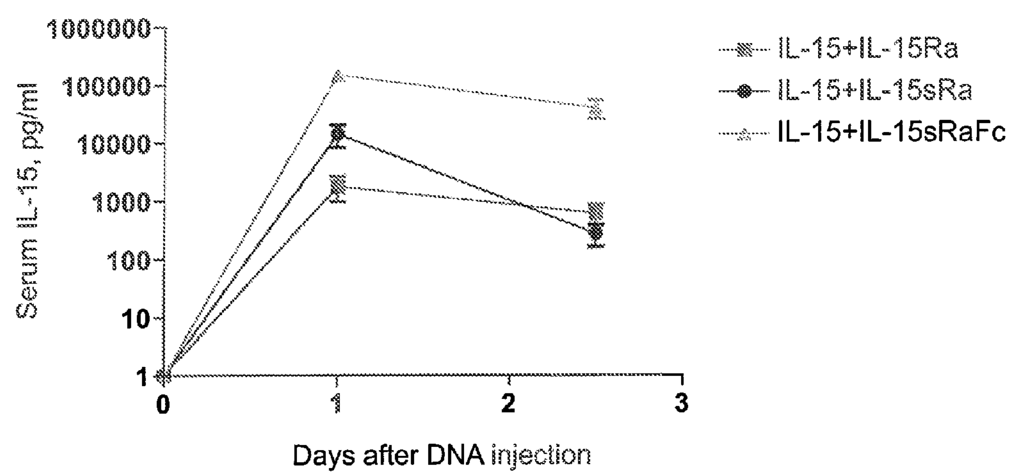
FIG. 18 illustrates IL-15 levels in serum following hydrodynamic delivery of DNA vectors expressing different forms of IL-15.

The three types of vectors have been tested in mice and have been shown to produce systemically bioactive levels of IL-15/IL-15Rα (see FIG. 18, showing expression of the three types of complexes). Because the localization, trafficking and stability of the different types of complexes vary, the biological effects on lymphocytes is also variable. FIG. 18 shows expression of different IL-15/IL-15Rα heterodimeric forms in mice by hydrodynamic injection of DNA vectors. Mice were injected at the tail vein (hydrodynamic delivery) with 0.1 μg of DNA expressing the different forms of IL-15/IL-15Rα. Plasma levels of IL-15 were measured at days 1 and 2.5 by R&D Quantiglo ELISA. Measurement of plasma levels of IL-15 produced by the different vectors showed that the highest plasma levels were achieved by the DNA vector producing IL-15/IL-15RαFc fusion. The stability of the produced proteins was also different, with the IL-15/IL-15RαFc and the IL-15/IL-15Rα full length showing the greatest stability. The IL-15/sIL-15Rα that is not cell associated was less stable.

Table 2 shows the CD4/CD8 ratios measured in the spleen and lung of mice treated with different IL-15/IL-15Rα heterodimeric forms, 2½ days after hydrodynamic injection of 0.1 μg of DNA vector (see FIG. 17).

| VECTOR | Spleen | Lung |
|---|---|---|
| IL-15/IL-15Rα (full length) | 1.36 | 0.8 |
| IL-15/sIL-15Rα (soluble) | 0.81 | 0.24 |
| IL-15/IL-15RαFc fusion to Fc | 0.63 | 0.52 |
| DNA vector control | 2 | 1.61 |

In these experiments, it was discovered that the different molecules have differential effects on lymphocytes. Therefore, the different IL-15 complexes can be used alone or in combinations for the most beneficial treatment under specific conditions. For example, delivery of combinations of IL-15/sRα soluble complex and IL-15/15RαFc fusion complex provides the opportunity to deliver both soluble and cell-bound IL-15 (through the Fc receptor) at different levels and proportions.

Figure 19:
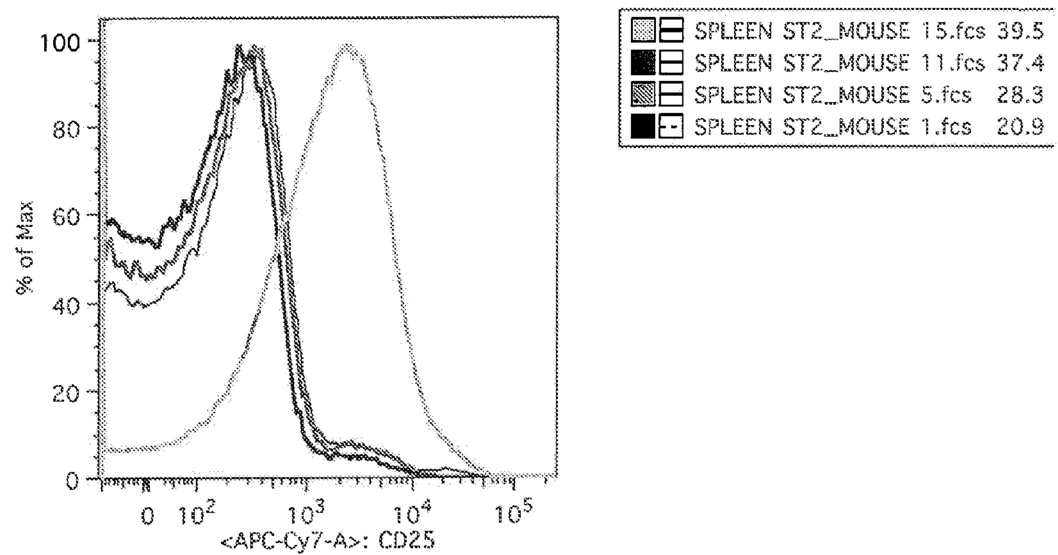
FIG. 19 illustrates CD25 expression on the surface of spleen T cells after IL-15/IL-15Rα DNA delivery.

In addition to the different ratios of CD4/CD8 cells (as shown in Table 1), the different IL-15 heterodimers also showed differences in the effects on other surface markers of lymphocytes. FIG. 19 shows that IL-15/15RαFc expression induced high levels of CD25 (IL-2 Receptor alpha) on both T CD4 and T CD8 cells, whereas the other forms of IL-15/IL-15Rα heterodimers did not affect CD25 expression strongly.

Figure 20:
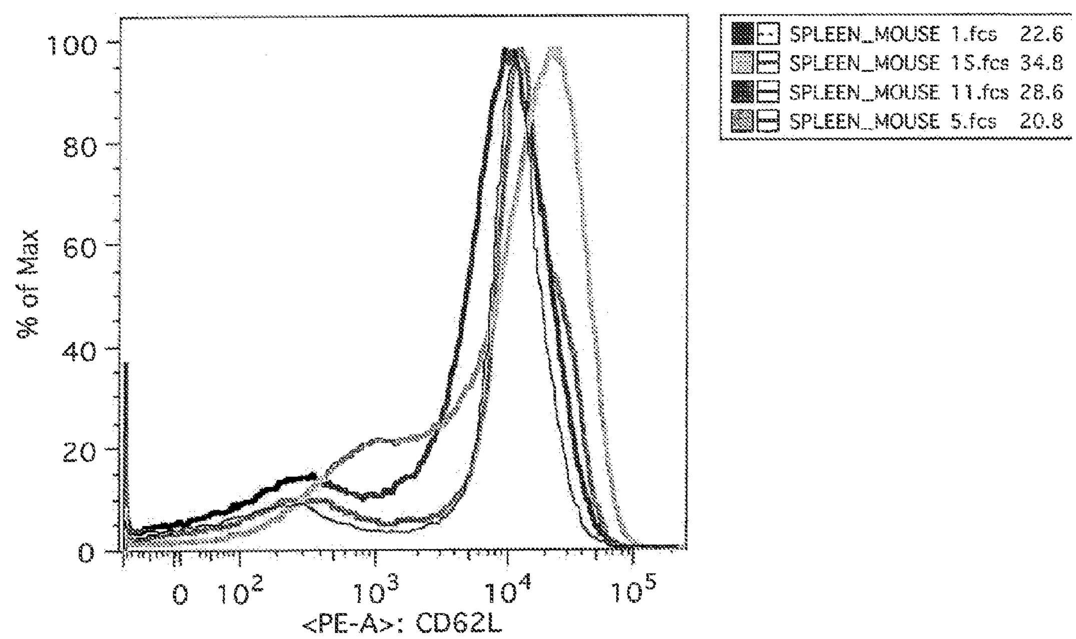
FIG. 20 illustrates expression of CD62L on the surface of spleen T cells after IL-15/IL-15Rα DNA delivery.
Figure 21:
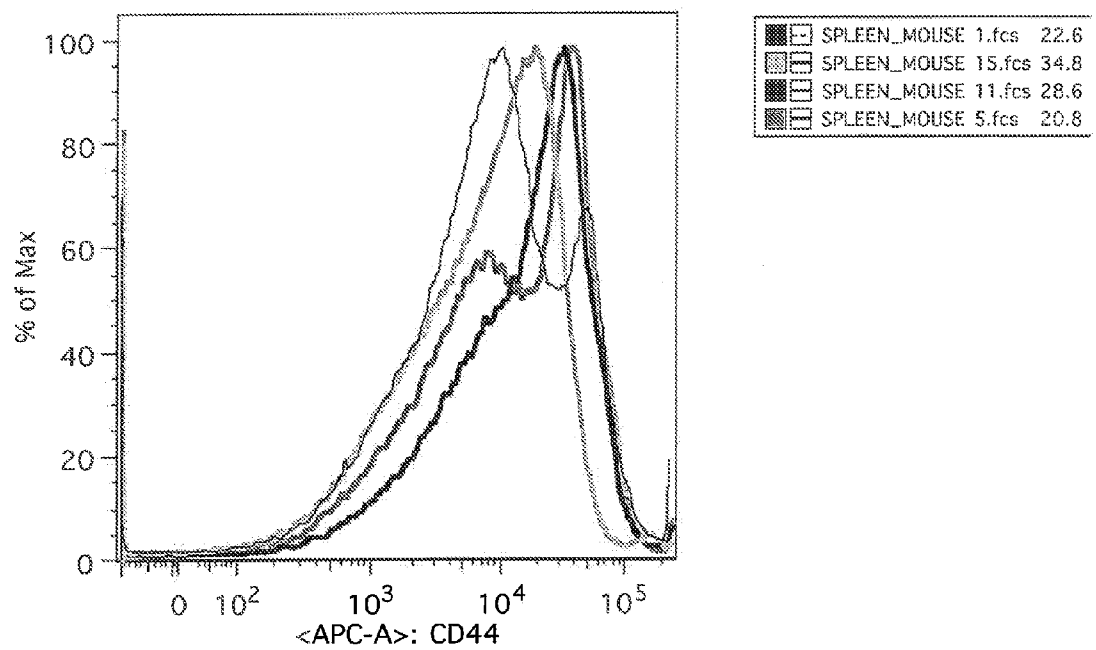
FIG. 21 illustrates express of CD44 on the surface of spleen T cells after IL-15/IL-5Rα DNA delivery.

FIG. 20 shows that IL-15/IL-15RαFc increased the levels of CD62L on the surface of spleen T cells, whereas the other forms of IL-15/IL-15Rα either did not affect or decreased average levels of CD62L on spleen T cells. In contrast, IL-15/IL-15RαFc was less effective in increasing CD44 on spleen T cells compared to either IL-15/IL-15Rα full-length or IL-15/IL-15sRα (FIG. 21).

Example 5

Protein Delivery

As an alternative method to provide IL-15, delivery of purified protein can be used. Protein purification from cell lines over-producing IL-15/IL-15Rα complexes has been achieved. Similar to DNA, different forms of the heterodimer can be used alone or in combinations for obtaining the appropriate effects:
1 Delivery of purified IL-15/soluble (s) IL-15Rα, such as SEQ ID NO:10 and SEQ ID NO:12.
2 Delivery of purified IL-15/IL-15RαFc fusion protein (fusion to the constant region of an immunoglobulin molecule, such as SEQ ID NO:17 and SEQ ID NO:20)

IL-15/sIL-15Rα was purified from overproducing human 293 cells and delivered into lympho-ablated mice. The results showed that this heterodimer is bioactive and that it promoted the proliferation of adoptively transferred lymphocytes (T cells, NK cells, but not B cells).

Figure 22:
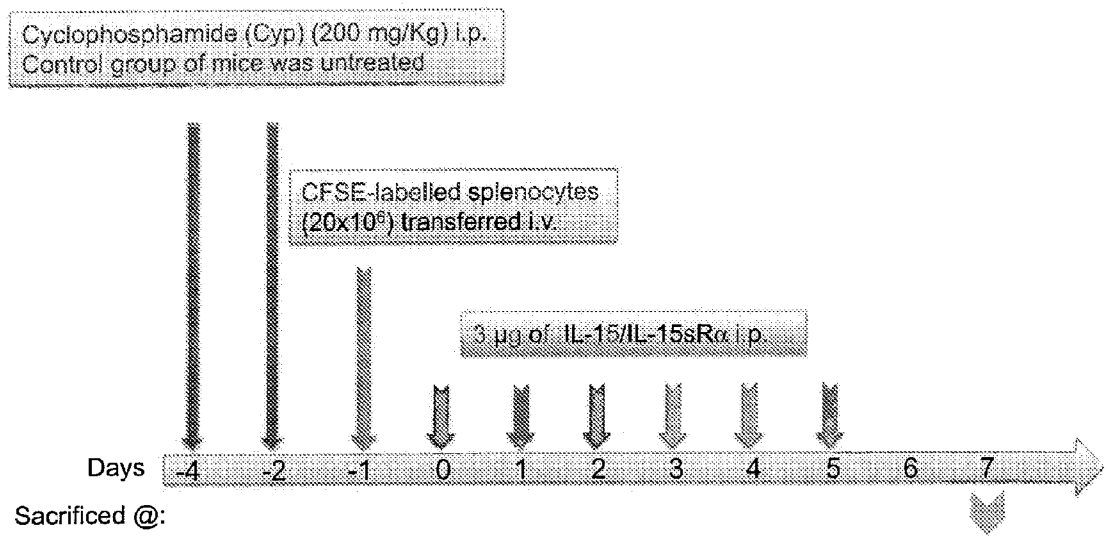
FIG. 22 illustrates a protocol (Example 5) for administration of purified IL-15/IL-15sRα in vivo.

Experimental procedure (FIG. 22): Mice were treated with Cyclophosphamide (Cyp) and two days later they were given 3 μg of HPLC-purified IL-15/s15Ra protein intraperitoneally for 6 days. Splenocytes were purified from young B1/6 mice, labeled with CFSE, and $10^7$ cells were injected by the IV route to the lympho-ablated animals. Proliferation of the adoptively transferred cells was followed by CFSE dilution.

Thus, these results indicate that different forms of IL-15/IL-15Rα heterodimer have different stability, interactions in the body, processing and stability. This offers the opportunity to exploit such properties for using these cytokines to provide maximal benefit. Accordingly, the different forms can be combined in different ratios and administration schedules. Different forms can be administered either simultaneously or sequentially.

Figure 23:
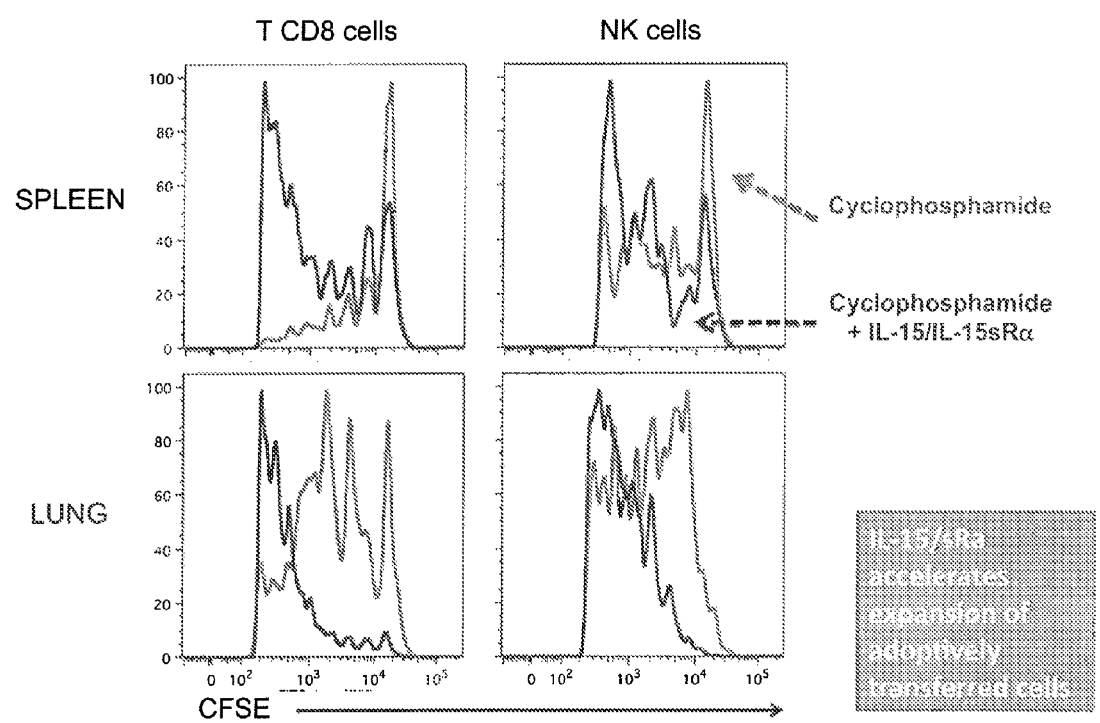
FIG. 23 illustrates that purified IL-15/IL-15Rα is bioactive in vivo.

IL-15Rα-Fc fusions previously employed have been used with various degrees of effectiveness. The studies exemplified in FIG. 23 show that the Fc fusion we used has greater plasma half-life compared to IL-15/s15Rα.

In the examples of sequences, described herein, the 205FC fusion (SEQ ID NO:17) contains the natural processing site generating the s15Ra from the membrane-bound form, whereas the 200FC fusion (SEQ ID NO:20) does not have an intact processing site. These are examples of Fc fusions that may be processed differently to generate non-cell associated forms after cleavage between the 15Rα region and the antibody constant region. Additional molecules can be generated having processing sites for cleavage and generating both cell associated and soluble forms of the cytokine. Additional methods for cell attachment, other than the Fc region are known in the art and can also be employed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Examples of Sequences

SEQ ID NO: 1

Human wild-type IL-15 nucleic acid sequence

```
ATGAGAATTTCGAAACCACATTTGAGAAGTATTTCCATCCAGTGCTACTTGTGTTTACTTCT

AAACAGTCATTTTCTAACTGAAGCTGGCATTCATGTCTTCATTTTGGGCTGTTTCAGTGCAG

GGCTTCCTAAAACAGAAGCCAACTGGGTGAATGTAATAAGTGATTTGAAAAAAATTGAAGAT

CTTATTCAATCTATGCATATTGATGCTACTTTATATACGGAAAGTGATGTTCACCCCAGTTG

CAAAGTAACAGCAATGAAGTGCTTTCTCTTGGAGTTACAAGTTATTTCACTTGAGTCTGGAG

ATGCAAGTATTCATGATACAGTAGAAAATCTGATCATCCTAGCAAACAACAGTTTGTCTTCT

AATGGGAATGTAACAGAATCTGGATGCAAAGAATGTGAGGAACTGGAGGAAAAAAATATTAA

AGAATTTTTGCAGAGTTTTGTACATATTGTCCAAATGTTCATCAACACTTCTTGA
```

SEQ ID NO: 2

Human wild-type IL-15 amino acid sequence

```
M R I S K P H L R S I S I Q C Y L C L L L

N S H F L T E A G I H V F I L G C F S A G

L P K T E A N W V N V I S D L K K I E D L

I Q S M H I D A T L Y T E S D V H P S C K

V T A M K C F L L E L Q V I S L E S G D A

S I H D T V E N L I I L A N N S L S S N G

N V T E S G C K E C E E L E E K N I K E F

L Q S F V H I V Q M F I N T S •
```

SEQ ID NO: 3

Human improved IL-15 nucleic acid sequence (opt1)

```
ATGCGGATCTCGAAGCCGCACCTGCGGTCGATATCGATCCAGTGCTACCTGTGCCTGCTCCT

GAACTCGCACTTCCTCACGGAGGCCGGTATACACGTCTTCATCCTGGGCTGCTTCTCGGCGG

GGCTGCCGAAGACGGAGGCGAACTGGGTGAACGTGATCTCGGACCTGAAGAAGATCGAGGAC

CTCATCCAGTCGATGCACATCGACGCGACGCTGTACACGGAGTCGGACGTCCACCCGTCGTG

CAAGGTCACGGCGATGAAGTGCTTCCTCCTGGAGCTCCAAGTCATCTCGCTCGAGTCGGGGG

ACGCGTCGATCCACGACACGGTGGAGAACCTGATCATCCTGGCGAACAACTCGCTGTCGTCG

AACGGGAACGTCACGGAGTCGGGCTGCAAGGAGTGCGAGGAGCTGGAGGAGAAGAACATCAA

GGAGTTCCTGCAGTCGTTCGTGCACATCGTCCAGATGTTCATCAACACGTCGTGA
```

SEQ ID NO: 4

Human improved IL-15 nucleic acid sequence (opt2)

```
ATGAGGATCAGCAAGCCCCACCTGAGGAGCATCAGCATCCAGTGCTACCTGTGCCTGCTGCT

GAACAGCCACTTCCTGACCGAGGCCGGTATACACGTGTTCATCCTGGGCTGCTTTAGCGCCG

GACTGCCCAAGACCGAGGCCAATTGGGTGAACGTGATCAGCGACCTGAAGAAGATCGAGGAC

CTCATCCAGAGCATGCACATCGACGCCACCCTGTACACCGAGAGCGATGTGCACCCCAGCTG

TAAGGTGACCGCCATGAAGTGCTTTCTGCTGGAGCTGCAAGTGATCAGCCTGGAGAGCGGCG

ACGCCAGCATCCACGACACCGTGGAGAACCTGATCATCCTGGCCAACAACAGCCTGAGCAGC

AACGGCAATGTGACCGAGAGCGGCTGTAAGGAGTGTGAGGAGCTGGAGGAGAAGAACATCAA

GGAGTTTCTGCAGAGCTTCGTGCACATCGTGCAGATGTTCATCAACACCAGCTGA
```

SEQ ID NO: 5

*Homo sapiens* interleukin 15 receptor, alpha (IL15RA), transcript variant 1, mRNA-GenBank Accession No. NM_002189

```
   1 cccagagcag cgctcgccac ctccccccgg cctgggcagc gctcgcccgg ggagtccagc

  61 ggtgtcctgt ggagctgccg ccatggcccc gcggcgggcg cgcggctgcc ggaccctcgg
```

-continued

```
 121 tctcccggcg ctgctactgc tgctgctgct ccggccgccg gcgacgcggg gcatcacgtg
 181 ccctcccccc atgtccgtgg aacacgcaga catctgggtc aagagctaca gcttgtactc
 241 cagggagcgg tacatttgta actctggttt caagcgtaaa gccggcacgt ccagcctgac
 301 ggagtgcgtg ttgaacaagg ccacgaatgt cgcccactgg acaaccccca gtctcaaatg
 361 cattagagac cctgccctgg ttcaccaaag gccagcgcca ccctccacag taacgacggc
 421 aggggtgacc ccacagccag agagcctctc cccttctgga aaagagcccg cagcttcatc
 481 tcccagctca aacaacacag cggccacaac agcagctatt gtcccgggct cccagctgat
 541 gccttcaaaa tcaccttcca caggaaccac agagataagc agtcatgagt cctcccacgg
 601 caccccctct cagacaacag ccaagaactg ggaactcaca gcatccgcct cccaccagcc
 661 gccaggtgtg tatccacagg gccacagcga caccactgtg gctatctcca cgtccactgt
 721 cctgctgtgt gggctgagcg ctgtgtctct cctggcatgc tacctcaagt caaggcaaac
 781 tcccccgctg gccagcgttg aaatggaagc catggaggct ctgccggtga cttgggggac
 841 cagcagcaga gatgaagact tggaaaactg ctctcaccac ctatgaaact cggggaaacc
 901 agcccagcta agtccggagt gaaggagcct ctctgcttta gctaaagacg actgagaaga
 961 ggtgcaagga agcgggctcc aggagcaagc tcaccaggcc tctcagaagt cccagcagga
1021 tctcacggac tgccgggtcg gcgcctcctg cgcgagggag caggttctcc gcattcccat
1081 gggcaccacc tgcctgcctg tcgtgccttg gacccagggc ccagcttccc aggagagacc
1141 aaaggcttct gagcaggatt tttatttcat tacagtgtga gctgcctgga atacatgtgg
1201 taatgaaata aaaaccctgc cccgaatctt ccgtccctca tcctaacttt cagttcacag
1261 agaaaagtga catacccaaa gctctctgtc aattacaagg cttctcctgg cgtgggagac
1321 gtctacaggg aagacaccag cgtttgggct tctaaccacc ctgtctccag ctgctctgca
1381 cacatggaca gggacctggg aaaggtggga gagatgctga gcccagcgaa tcctctccat
1441 tgaaggattc aggaagaaga aaactcaact cagtgccatt ttacgaatat atgcgtttat
1501 atttatactt ccttgtctat tatatctata cattatatat tatttgtatt ttgacattgt
1561 accttgtata aacaaaataa aacatctatt ttcaatattt ttaaaatgca
```

SEQ ID NO: 6 interleukin 15 receptor, alpha isoform 1 precursor [*Homo sapiens*]-GenBank Accession No. NP_002180

```
   1 maprrargcr tlglpallll lllrppatrg itcpppmsve hadiwvksys lysreryicn
  61 sgfkrkagts sltecvlnka tnvahwttps lkcirdpalv hqrpappstv ttagvtpqpe
 121 slspsgkepa asspssnnta attaaivpgs qlmpskspst gtteisshes shgtpsqtta
 181 knweltasas hqppgvypqg hsdttvaist stvllcglsa vsllacylks rqtpplasve
 241 meamealpvt wgtssrdedl encshhl
```

SEQ ID NO: 7

*Homo sapiens* interleukin 15 receptor, alpha (IL15RA), transcript variant 2, mRNA-GenBank Accession No. NM_172200

```
   1 caggaattcg gcgaagtggc ggagctgggg ccccagcggg cgccgggggc cgcgggagcc
  61 agcaggtggc gggggctgcg ctccgcccgg gccagagcgc accaggcagg tgcccgcgcc
 121 tccgcaccgc ggcgacacct ccgcgggcac tcacccaggc cggccgctca caaccgagcg
 181 cagggccgcg gagggagacc aggaaagccg aaggcggagc agctggaggc gaccagcgcc
 241 gggcgaggtc aagtggatcc gagccgcaga gagggctgga gagagtctgc tctccgatga
 301 ctttgcccac tctcttcgca gtggggacac cggaccgagt gcacactgga ggtcccagag
 361 cacgacgagc gcggaggacc gggaggctcc cgggcttgcg tgggcatcac gtgccctccc
```

-continued 421 cccatgtccg tggaacacgc agacatctgg gtcaagagct acagcttgta ctccagggag 481 cggtacattt gtaactctgg tttcaagcgt aaagccggca cgtccagcct gacggagtgc 541 gtgttgaaca aggccacgaa tgtcgcccac tggacaaccc ccagtctcaa atgcattaga 601 gaccctgccc tggttcacca aaggccagcg ccaccctcca cagtaacgac ggcaggggtg 661 accccacagc cagagagcct ctccccttct ggaaaagagc ccgcagcttc atctcccagc 721 tcaaacaaca cagcggccac aacagcagct attgtcccgg gctcccagct gatgccttca 781 aaatcacctt ccacaggaac cacagagata agcagtcatg agtcctccca cggcaccccc 841 tctcagacaa cagccaagaa ctgggaactc acagcatccg cctcccacca gccgccaggt 901 gtgtatccac agggccacag cgacaccact gtggctatct ccacgtccac tgtcctgctg 961 tgtgggctga gcgctgtgtc tctcctggca tgctacctca agtcaaggca aactcccccg 1021 ctggccagcg ttgaaatgga agccatggag gctctgccgg tgacttgggg gaccagcagc 1081 agagatgaag acttggaaaa ctgctctcac cacctatgaa actcggggaa accagcccag 1141 ctaagtccgg agtgaaggag cctctctgct ttagctaaag acgactgaga agaggtgcaa 1201 ggaagcgggc tccaggagca agctcaccag gcctctcaga agtcccagca ggatctcacg 1261 gactgccggg tcggcgcctc ctgcgcgagg gagcaggttc tccgcattcc catgggcacc 1321 acctgcctgc ctgtcgtgcc ttggacccag ggcccagctt cccaggagag accaaaggct 1381 tctgagcagg atttttattt cattacagtg tgagctgcct ggaatacatg tggtaatgaa 1441 ataaaaaccc tgccccgaat cttccgtccc tcatcctaac tttcagttca cagagaaaag 1501 tgacataccc aaagctctct gtcaattaca aggcttctcc tggcgtggga gacgtctaca 1561 gggaagacac cagcgtttgg gcttctaacc accctgtctc cagctgctct gcacacatgg 1621 acagggacct gggaaaggtg ggagagatgc tgagcccagc gaatcctctc cattgaagga 1681 ttcaggaaga agaaaactca actcagtgcc attttacgaa tatatgcgtt tatatttata 1741 cttccttgtc tattatatct atacattata tattatttgt attttgacat tgtaccttgt 1801 ataaacaaaa taaaacatct attttcaata tttttaaaat gca

SEQ ID NO: 8 interleukin 15 receptor, alpha isoform 2 [*Homo sapiens*]-
GenBank Accession No. NP_751950

1 msvehadiwv ksyslysrer yicnsgfkrk agtssltecv lnkatnvahw ttpslkcird 61 palvhqrpap pstvttagvt pqpeslspsg kepaasspss nntaattaai vpgsqlmpsk 121 spstgtteis shesshgtps qttaknwelt asashqppgv ypqghsdttv aiststvllc 181 glsaysllac ylksrqtppl asvemeamea lpvtwgtssr dedlencshh l

SEQ ID NO: 9

Improved human interleukin 15 (IL-15) receptor alpha (IL15Ra),
transcript variant 1 (OPT)

atggccccga ggcgggcgcg aggctgccgg accctcggtc tcccggcgct gctactgctc 60
ctgctgctcc ggccgccggc gacgcggggc atcacgtgcc cgccccccat gtccgtggag 120
cacgcagaca tctgggtcaa gagctacagc ttgtactccc gggagcggta catctgcaac 180
tcgggtttca agcggaaggc cggcacgtcc agcctgacgg agtgcgtgtt gaacaaggcc 240
acgaatgtcg cccactggac gaccccctcg ctcaagtgca tccgcgaccc ggccctggtt 300
caccagcggc ccgcgccacc ctccaccgta acgacggcgg gggtgacccc gcagccggag 360
agcctctccc cgtcgggaaa ggagcccgcc gcgtcgtcgc ccagctcgaa caacacggcg 420
gccacaactg cagcgatcgt cccgggctcc cagctgatgc cgtcgaagtc gccgtccacg 480
ggaaccacgg agatcagcag tcatgagtcc tcccacggca ccccctcgca aacgacggcc 540
aagaactggg aactcacggc gtccgcctcc caccagccgc cgggggtgta tccgcaaggc 600

-continued

```
cacagcgaca ccacggtggc gatctccacg tccacggtcc tgctgtgtgg gctgagcgcg 660

gtgtcgctcc tggcgtgcta cctcaagtcg aggcagactc cccgctggc cagcgttgag 720

atggaggcca tggaggctct gccggtgacg tgggggacca gcagcaggga tgaggacttg 780

gagaactgct cgcaccacct ataatga                                      807
```

SEQ ID NO: 10 improved human interleukin 15 (IL-15) receptor
alpha (IL15Ra), transcript variant 1 (OPT)

```
Met Ala Pro Arg Arg Ala Arg Gly Cys Arg Thr Leu Gly Leu Pro Ala
  1               5                  10                  15

Leu Leu Leu Leu Leu Leu Leu Arg Pro Pro Ala Thr Arg Gly Ile Thr
             20                  25                  30

Cys Pro Pro Pro Met Ser Val Glu His Ala Asp Ile Trp Val Lys Ser
         35                  40                  45

Tyr Ser Leu Tyr Ser Arg Glu Arg Tyr Ile Cys Asn Ser Gly Phe Lys
     50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

SEQ ID NO: 11 improved human soluble interleukin 15 (IL-15)
receptor alpha (IL-15sRa) (OPT)

```
atggccccga ggcgggcgcg aggctgccgg accctcggtc tcccggcgct gctactgctc  60

ctgctgctcc ggccgccggc gacgcggggc atcacgtgcc cgcccccat gtccgtggag 120

cacgcagaca tctgggtcaa gagctacagc ttgtactccc gggagcggta catctgcaac 180

tcgggtttca agcggaaggc cggcacgtcc agcctgacgg agtgcgtgtt gaacaaggcc 240

acgaatgtcg cccactggac gacccccctcg ctcaagtgca tccgcgaccc ggccctggtt 300

caccagcggc ccgcgccacc ctccaccgta acgacggcgg gggtgacccc gcagccggag 360

agcctctccc cgtcgggaaa ggagcccgcc gcgtcgtcgc ccagctcgaa caacacggcg 420

gccacaactg cagcgatcgt cccgggctcc cagctgatgc cgtcgaagtc gccgtccacg 480
```

-continued

```
ggaaccacgg agatcagcag tcatgagtcc tcccacggca ccccctcgca aacgacggcc 540

aagaactggg aactcacggc gtccgcctcc caccagccgc cgggggtgta tccgcaaggc 600

cacagcgaca ccacgtaatg a                                           621
```

SEQ ID NO: 12 improved human soluble interleukin 15 (IL-15) receptor alpha (IL-15sRa) (OPT)

```
Met Ala Pro Arg Arg Ala Arg Gly Cys Arg Thr Leu Gly Leu Pro Ala
  1               5                  10                  15

Leu Leu Leu Leu Leu Leu Leu Arg Pro Pro Ala Thr Arg Gly Ile Thr
             20                  25                  30

Cys Pro Pro Pro Met Ser Val Glu His Ala Asp Ile Trp Val Lys Ser
         35                  40                  45

Tyr Ser Leu Tyr Ser Arg Glu Arg Tyr Ile Cys Asn Ser Gly Phe Lys
     50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Arg Asp
                 85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205
```

SEQ ID NO: 13

Dual expression plasmid human IL15Ra + IL15

CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGCGCGCGTCGAGGAATTCGCTAGCAAGAAATGGCCCCGAGGCGGGCGCGAGGCTG

CCGGACCCTCGGTCTCCCGGCGCTGCTACTGCTCCTGCTGCTCCGGCCGCCGGCGACGCGGG

GCATCACGTGCCCGCCCCCCATGTCCGTGGAGCACGCAGACATCTGGGTCAAGAGCTACAGC

TTGTACTCCCGGGAGCGGTACATCTGCAACTCGGGTTTCAAGCGGAAGGCCGGCACGTCCAG

-continued

CCTGACGGAGTGCGTGTTGAACAAGGCCACGAATGTCGCCCACTGGACGACCCCCTCGCTCA

AGTGCATCCGCGACCCGGCCCTGGTTCACCAGCGGCCCGCGCCACCCTCCACCGTAACGACG

GCGGGGGTGACCCCGCAGCCGGAGAGCCTCTCCCCGTCGGGAAAGGAGCCCGCCGCGTCGTC

GCCCAGCTCGAACAACACGGCGGCCACAACTGCAGCGATCGTCCCGGGCTCCCAGCTGATGC

CGTCGAAGTCGCCGTCCACGGGAACCACGGAGATCAGCAGTCATGAGTCCTCCCACGGCACC

CCCTCGCAAACGACGGCCAAGAACTGGGAACTCACGGCGTCCGCCTCCCACCAGCCGCCGGG

GGTGTATCCGCAAGGCCACAGCGACACCACGGTGGCGATCTCCACGTCCACGGTCCTGCTGT

GTGGGCTGAGCGCGGTGTCGCTCCTGGCGTGCTACCTCAAGTCGAGGCAGACTCCCCCGCTG

GCCAGCGTTGAGATGGAGGCCATGGAGGCTCTGCCGGTGACGTGGGGGACCAGCAGCAGGGA

TGAGGACTTGGAGAACTGCTCGCACCACCTATAATGAGAATTCACGCGTGGATCTGATATCG

GATCTGCTGTGCCTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAATTGCATCGCATTG

TCTGAGTAGGTGTCATTCTATTCTGGGGGGTGGGGTGGGGCAGGACAGCAAGGGGGAGGATT

GGGAAGACAATAGCAGGCATGCTGGGGATGCGGTGGGCTCTATGGGTACCCAGGTGCTGAAG

AATTGACCCGGTTCCTCCTGGGCCAGAAAGAAGCAGGCACATCCCCTTCTCTGTGACACACC

CTGTCCACGCCCCTGGTTCTTAGTTCCAGCCCCACTCATAGGACACTCATAGCTCAGGAGGG

CTCCGCCTTCAATCCCACCCGCTAAAGTACTTGGAGCGGTCTCTCCCTCCCTCATCAGCCCA

CCAAACCAAACCTAGCCTCCAAGAGTGGGAAGAAATTAAAGCAAGATAGGCTATTAAGTGCA

GAGGGAGAGAAAATGCCTCCAACATGTGAGGAAGTAATGAGAGAAATCATAGAATTTCTTCC

GCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGA

CCCTGCCGCTTACCGGATACCTGTCCGCCTTTCTCCCTTCGGGAAGCGTGGCGCTTTCTCAA

TGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTTGGTCT

GACAGTTACCAATGCTTAATCAGTGAGGCACCTATCTCAGCGATCTGTCTATTTCGTTCATC

CATAGTTGCCTGACTCGGGGGGGGGGGGCGCTGAGGTCTGCCTCGTGAAGAAGGTGTTGCTG

ACTCATACCAGGCCTGAATCGCCCCATCATCCAGCCAGAAAGTGAGGGAGCCACGGTTGATG

AGAGCTTTGTTGTAGGTGGACCAGTTGGTGATTTTGAACTTTTGCTTTGCCACGGAACGGTC

TGCGTTGTCGGGAAGATGCGTGATCTGATCCTTCAACTCAGCAAAAGTTCGATTTATTCAAC

AAAGCCGCCGTCCCGTCAAGTCAGCGTAATGCTCTGCCAGTGTTACAACCAATTAACCAATT

CTGATTAGAAAAACTCATCGAGCATCAAATGAAACTGCAATTTATTCATATCAGGATTATCA

-continued

ATACCATATTTTTGAAAAAGCCGTTTCTGTAATGAAGGAGAAAACTCACCGAGGCAGTTCCA

TAGGATGGCAAGATCCTGGTATCGGTCTGCGATTCCGACTCGTCCAACATCAATACAACCTA

TTAATTTCCCCTCGTCAAAAATAAGGTTATCAAGTGAGAAATCACCATGAGTGACGACTGAA

TCCGGTGAGAATGGCAAAAGCTTATGCATTTCTTTCCAGACTTGTTCAACAGGCCAGCCATT

ACGCTCGTCATCAAAATCACTCGCATCAACCAAACCGTTATTCATTCGTGATTGCGCCTGAG

CGAGACGAAATACGCGATCGCTGTTAAAAGGACAATTACAAACAGGAATCGAATGCAACCGG

CGCAGGAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGTACGGA

TAAAATGCTTGATGGTCGGAAGAGGCATAAATTCCGTCAGCCAGTTTAGTCTGACCATCTCA

TCTGTAACATCATTGGCAACGCTACCTTTGCCATGTTTCAGAAACAACTCTGGCGCATCGGG

CTTCCCATACAATCGATAGATTGTCGCACCTGATTGCCCGACATTATCGCGAGCCCATTTAT

ACCCATATAAATCAGCATCCATGTTGGAATTTAATCGCGGCCTCGAGCAAGACGTTTCCCGT

TGAATATGGCTCATAACACCCCTTGTATTACTGTTTATGTAAGCAGACAGTTTTATTGTTCA

TGATGATATATTTTTATCTTGTGCAATGTAACATCAGAGATTTTGAGACACAACGTGGATCA

TCCAGACATGATAAGATACATTGATGAGTTTGGACAAACCACAACTAGAATGCAGTGAAAAA

AATGCTTTATTTGTGAAATTTGTGATGCTATTGCTTTATTTGTAACCATTATAAGCTGCAAT

AAACAAGTTAACAACAACAATTGCATTCATTTTATGTTTCAGGTTCAGGGGGAGGTGTGGGA

GGTTTTTTAAAGCAAGTAAAACCTCTACAAATGTGGTATGGCTGATTATGATCGTCGAGGAT

CTGGATCCGTTAACCGATATCCGCGAATTCGGCGCGCCGGGCCCTCACGACGTGTTGATGAA

CATCTGGACGATGTGCACGAACGACTGCAGGAACTCCTTGATGTTCTTCTCCTCCAGCTCCT

CGCACTCCTTGCAGCCCGACTCCGTGACGTTCCCGTTCGACGACAGCGAGTTGTTCGCCAGG

ATGATCAGGTTCTCCACCGTGTCGTGGATCGACGCGTCCCCCGACTCGAGCGAGATGACTTG

GAGCTCCAGGAGGAAGCACTTCATCGCCGTGACCTTGCACGACGGGTGGACGTCCGACTCCG

TGTACAGCGTCGCGTCGATGTGCATCGACTGGATGAGGTCCTCGATCTTCTTCAGGTCCGAG

ATCACGTTCACCCAGTTCGCCTCCGTCTTCGGCAGCCCCGCCGAGAAGCAGCCCAGGATGAA

GACGTGTATACCGGCCTCCGTGAGGAAGTGCGAGTTCAGGAGCAGGCACAGGTAGCACTGGA

TCGATATCGACCGCAGGTGCGGCTTCGAGATCCGCATTTCTTGTCGACACTCGACAGATCCA

AACGCTCCTCCGACGTCCCCAGGCAGAATGGCGGTTCCCTAAACGAGCATTGCTTATATAGA

CCTCCCATTAGGCACGCCTACCGCCCATTTACGTCAATGGAACGCCCATTTGCGTCATTGCC

CCTCCCCATTGACGTCAATGGGGATGTACTTGGCAGCCATCGCGGGCCATTTACCGCCATTG

ACGTCAATGGGAGTACTGCCAATGTACCCTGGCGTACTTCCAATAGTAATGTACTTGCCAAG

TTACTATTAATAGATATTGATGTACTGCCAAGTGGGCCATTTACCGTCATTGACGTCAATAG

GGGGCGTGAGAACGGATATGAATGGGCAATGAGCCATCCCATTGACGTCAATGGTGGGTGGT

CCTATTGACGTCAATGGGCATTGAGCCAGGCGGGCCATTTACCGTAATTGACGTCAATGGGG

GAGGCGCCATATACGTCAATAGGACCGCCCATATGACGTCAATAGGAAAGACCATGAGGCCC

TTTCGTCTCGCGCGTTTCGGTGATGACGGTGAAAACCTCTGACACATGCAGCTCCCGGAGAC

GGTCACAGCTTGTCTGTAAGCGGATGCCGGGAGCAGACAAGCCCGTCAGGGCGCGTCAGCGG

GTGTTGGCGGGTGTCGGGGCTGGCTTAACTATGCGGCATCAGAGCAGATTGTACTGAGAGTG

CACCATATGCGGTGTGAAATACCGCACAGATGCGTAAGGAGAAAATACCGCATCAGATTGGC

TATTGG

-continued

SEQ ID NO: 14

Dual expression plasmid human IL15Ra + IL15tPA6

CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGCGCGCGTCGAGGAATTCGCTAGCAAGAAATGGCCCCGAGGCGGGCGCGAGGCTG

CCGGACCCTCGGTCTCCCGGCGCTGCTACTGCTCCTGCTGCTCCGGCCGCCGGCGACGCGGG

GCATCACGTGCCCGCCCCCCATGTCCGTGGAGCACGCAGACATCTGGGTCAAGAGCTACAGC

TTGTACTCCCGGGAGCGGTACATCTGCAACTCGGGTTTCAAGCGGAAGGCCGGCACGTCCAG

CCTGACGGAGTGCGTGTTGAACAAGGCCACGAATGTCGCCCACTGGACGACCCCCTCGCTCA

AGTGCATCCGCGACCCGGCCCTGGTTCACCAGCGGCCCGCGCCACCCTCCACCGTAACGACG

GCGGGGGTGACCCCGCAGCCGGAGAGCCTCTCCCCGTCGGGAAAGGAGCCCGCCGCGTCGTC

GCCCAGCTCGAACAACACGGCGGCCACAACTGCAGCGATCGTCCCGGGCTCCCAGCTGATGC

CGTCGAAGTCGCCGTCCACGGGAACCACGGAGATCAGCAGTCATGAGTCCTCCCACGGCACC

CCCTCGCAAACGACGGCCAAGAACTGGGAACTCACGGCGTCCGCCTCCCACCAGCCGCCGGG

GGTGTATCCGCAAGGCCACAGCGACACCACGGTGGCGATCTCCACGTCCACGGTCCTGCTGT

GTGGGCTGAGCGCGGTGTCGCTCCTGGCGTGCTACCTCAAGTCGAGGCAGACTCCCCCGCTG

GCCAGCGTTGAGATGGAGGCCATGGAGGCTCTGCCGGTGACGTGGGGGACCAGCAGCAGGGA

TGAGGACTTGGAGAACTGCTCGCACCACCTATAATGAGAATTCACGCGTGGATCTGATATCG

GATCTGCTGTGCCTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAATTGCATCGCATTG

TCTGAGTAGGTGTCATTCTATTCTGGGGGGTGGGGTGGGGCAGGACAGCAAGGGGGAGGATT

GGGAAGACAATAGCAGGCATGCTGGGGATGCGGTGGGCTCTATGGGTACCCAGGTGCTGAAG

AATTGACCCGGTTCCTCCTGGGCCAGAAAGAAGCAGGCACATCCCCTTCTCTGTGACACACC

CTGTCCACGCCCCTGGTTCTTAGTTCCAGCCCCACTCATAGGACACTCATAGCTCAGGAGGG

CTCCGCCTTCAATCCCACCCGCTAAAGTACTTGGAGCGGTCTCTCCCTCCCTCATCAGCCCA

CCAAACCAAACCTAGCCTCCAAGAGTGGGAAGAAATTAAAGCAAGATAGGCTATTAAGTGCA

GAGGGAGAGAAAATGCCTCCAACATGTGAGGAAGTAATGAGAGAAATCATAGAATTTCTTCC

GCTTCCTCGCTCACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGA

-continued

CCCTGCCGCTTACCGGATACCTGTCCGCCTTTCTCCCTTCGGGAAGCGTGGCGCTTTCTCAA

TGCTCACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGG

TATGTAGGCGGTGCTACAGAGTTCTTGAAGTGGTGGCCTAACTACGGCTACACTAGAAGGAC

AGTATTTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAGATTACG

CGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGA

TCCTTTTAAATTAAAAATGAAGTTTTAAATCAATCTAAAGTATATATGAGTAAACTTGGTCT

GACAGTTACCAATGCTTAATCAGTGAGGCACCTATCTCAGCGATCTGTCTATTTCGTTCATC

CATAGTTGCCTGACTCGGGGGGGGGGGGCGCTGAGGTCTGCCTCGTGAAGAAGGTGTTGCTG

ACTCATACCAGGCCTGAATCGCCCCATCATCCAGCCAGAAAGTGAGGGAGCCACGGTTGATG

AGAGCTTTGTTGTAGGTGGACCAGTTGGTGATTTTGAACTTTTGCTTTGCCACGGAACGGTC

TGCGTTGTCGGGAAGATGCGTGATCTGATCCTTCAACTCAGCAAAAGTTCGATTTATTCAAC

AAAGCCGCCGTCCCGTCAAGTCAGCGTAATGCTCTGCCAGTGTTACAACCAATTAACCAATT

CTGATTAGAAAAACTCATCGAGCATCAAATGAAACTGCAATTTATTCATATCAGGATTATCA

ATACCATATTTTTGAAAAAGCCGTTTCTGTAATGAAGGAGAAAACTCACCGAGGCAGTTCCA

TAGGATGGCAAGATCCTGGTATCGGTCTGCGATTCCGACTCGTCCAACATCAATACAACCTA

TTAATTTCCCCTCGTCAAAAATAAGGTTATCAAGTGAGAAATCACCATGAGTGACGACTGAA

TCCGGTGAGAATGGCAAAAGCTTATGCATTTCTTTCCAGACTTGTTCAACAGGCCAGCCATT

ACGCTCGTCATCAAAATCACTCGCATCAACCAAACCGTTATTCATTCGTGATTGCGCCTGAG

CGAGACGAAATACGCGATCGCTGTTAAAAGGACAATTACAAACAGGAATCGAATGCAACCGG

CGCAGGAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGTACGGA

TAAAATGCTTGATGGTCGGAAGAGGCATAAATTCCGTCAGCCAGTTTAGTCTGACCATCTCA

TCTGTAACATCATTGGCAACGCTACCTTTGCCATGTTTCAGAAACAACTCTGGCGCATCGGG

CTTCCCATACAATCGATAGATTGTCGCACCTGATTGCCCGACATTATCGCGAGCCCATTTAT

ACCCATATAAATCAGCATCCATGTTGGAATTTAATCGCGGCCTCGAGCAAGACGTTTCCCGT

TGAATATGGCTCATAACACCCCTTGTATTACTGTTTATGTAAGCAGACAGTTTTATTGTTCA

TGATGATATATTTTTATCTTGTGCAATGTAACATCAGAGATTTTGAGACACAACGTGGATCA

TCCAGACATGATAAGATACATTGATGAGTTTGGACAAACCACAACTAGAATGCAGTGAAAAA

AATGCTTTATTTGTGAAATTTGTGATGCTATTGCTTTATTTGTAACCATTATAAGCTGCAAT

AAACAAGTTAACAACAACAATTGCATTCATTTTATGTTTCAGGTTCAGGGGGAGGTGTGGGA

GGTTTTTTAAAGCAAGTAAAACCTCTACAAATGTGGTATGGCTGATTATGATCGTCGAGGAT

CTGGATCTGGATCCGTTAACCGATATCCGCGAATTCGGCGCGCCGGGCCCTCACGACGTGTT

GATGAACATCTGGACGATGTGCACGAACGACTGCAGGAACTCCTTGATGTTCTTCTCCTCCA

GCTCCTCGCACTCCTTGCAGCCCGACTCCGTGACGTTCCCGTTCGACGACAGCGAGTTGTTC

GCCAGGATGATCAGGTTCTCCACCGTGTCGTGGATCGACGCGTCCCCCGACTCGAGCGAGAT

GACTTGGAGCTCCAGGAGGAAGCACTTCATCGCCGTGACCTTGCACGACGGGTGGACGTCCG

ACTCCGTGTACAGCGTCGCGTCGATGTGCATCGACTGGATGAGGTCCTCGATCTTCTTCAGG

-continued

TCCGAGATCACGTTCACCCAGTTTCTGGCTCCTCTTCTGAATCGGGCATGGATTTCCTGGCT

GGGCGAAACGAAGACTGCTCCACACAGCAGCAGCACACAGCAGAGCCCTCTCTTCATTGCAT

CCATTTCTTGTCGACAGATCCAAACGCTCCTCCGACGTCCCCAGGCAGAATGGCGGTTCCCT

AAACGAGCATTGCTTATATAGACCTCCCATTAGGCACGCCTACCGCCCATTTACGTCAATGG

AACGCCCATTTGCGTCATTGCCCCTCCCCATTGACGTCAATGGGGATGTACTTGGCAGCCAT

CGCGGGCCATTTACCGCCATTGACGTCAATGGGAGTACTGCCAATGTACCCTGGCGTACTTC

CAATAGTAATGTACTTGCCAAGTTACTATTAATAGATATTGATGTACTGCCAAGTGGGCCAT

TTACCGTCATTGACGTCAATAGGGGGCGTGAGAACGGATATGAATGGGCAATGAGCCATCCC

ATTGACGTCAATGGTGGGTGGTCCTATTGACGTCAATGGGCATTGAGCCAGGCGGGCCATTT

ACCGTAATTGACGTCAATGGGGGAGGCGCCATATACGTCAATAGGACCGCCCATATGACGTC

AATAGGAAAGACCATGAGGCCCTTTCGTCTCGCGCGTTTCGGTGATGACGGTGAAAACCTCT

GACACATGCAGCTCCCGGAGACGGTCACAGCTTGTCTGTAAGCGGATGCCGGGAGCAGACAA

GCCCGTCAGGGCGCGTCAGCGGGTGTTGGCGGGTGTCGGGGCTGGCTTAACTATGCGGCATC

AGAGCAGATTGTACTGAGAGTGCACCATATGCGGTGTGAAATACCGCACAGATGCGTAAGGA

GAAAATACCGCATCAGATTGGCTATTGG

SEQ ID NO: 15

Dual expression plasmid human IL15sRa(soluble) + IL15tPA6

CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGCGCGCGTCGAGGAATTCGCTAGCAAGAAATGGCCCCGAGGCGGGCGCGAGGCTG

CCGGACCCTCGGTCTCCCGGCGCTGCTACTGCTCCTGCTGCTCCGGCCGCCGGCGACGCGGG

GCATCACGTGCCCGCCCCCCATGTCCGTGGAGCACGCAGACATCTGGGTCAAGAGCTACAGC

TTGTACTCCCGGGAGCGGTACATCTGCAACTCGGGTTTCAAGCGGAAGGCCGGCACGTCCAG

CCTGACGGAGTGCGTGTTGAACAAGGCCACGAATGTCGCCCACTGGACGACCCCCTCGCTCA

AGTGCATCCGCGACCCGGCCCTGGTTCACCAGCGGCCCGCGCCACCCTCCACCGTAACGACG

GCGGGGGTGACCCCGCAGCCGGAGAGCCTCTCCCCGTCGGGAAAGGAGCCCGCCGCGTCGTC

GCCCAGCTCGAACAACACGGCGGCCACAACTGCAGCGATCGTCCCGGGCTCCCAGCTGATGC

CGTCGAAGTCGCCGTCCACGGGAACCACGGAGATCAGCAGTCATGAGTCCTCCCACGGCACC

CCCTCGCAAACGACGGCCAAGAACTGGGAACTCACGGCGTCCGCCTCCCACCAGCCGCCGGG

GGTGTATCCGCAAGGCCACAGCGACACCACGTAATGAGAATTCGCGGATATCGGTTAACGGA

TCCAGATCTGCTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGCATCGC

-continued

ATTGTCTGAGTAGGTGTCATTCTATTCTGGGGGGTGGGGTGGGGCAGGACAGCAAGGGGGAG

GATTGGGAAGACAATAGCAGGCATGCTGGGGATGCGGTGGGCTCTATGGGTACCCAGGTGCT

GAAGAATTGACCCGGTTCCTCCTGGGCCAGAAAGAAGCAGGCACATCCCCTTCTCTGTGACA

CACCCTGTCCACGCCCCTGGTTCTTAGTTCCAGCCCCACTCATAGGACACTCATAGCTCAGG

AGGGCTCCGCCTTCAATCCCACCCGCTAAAGTACTTGGAGCGGTCTCTCCCTCCCTCATCAG

CCCACCAAACCAAACCTAGCCTCCAAGAGTGGGAAGAAATTAAAGCAAGATAGGCTATTAAG

TGCAGAGGGAGAGAAAATGCCTCCAACATGTGAGGAAGTAATGAGAGAAATCATAGAATTTC

TTCCGCTTCCTCGCTCACTGACTCGCTGCGCTCGGTCGTTCGGCTGCGGCGAGCGGTATCAG

CTCACTCAAAGGCGGTAATACGGTTATCCACAGAATCAGGGGATAACGCAGGAAAGAACATG

TGAGCAAAAGGCCAGCAAAAGGCCAGGAACCGTAAAAAGGCCGCGTTGCTGGCGTTTTTCCA

TAGGCTCCGCCCCCCTGACGAGCATCACAAAAATCGACGCTCAAGTCAGAGGTGGCGAAACC

CGACAGGACTATAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGCGTGGCGCTTTC

TCAATGCTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACACTAGAA

GGACAGTATTTGGTATCTGCGCTCTGCTGAAGCCAGTTACCTTCGGAAAAAGAGTTGGTAGC

TCTTGATCCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCTGACGCTC

AGTGGAACGAAAACTCACGTTAAGGGATTTTGGTCATGAGATTATCAAAAAGGATCTTCACC

TAGATCCTTTTAAATTAAAAATGAAGTTTTAAATCAATCTAAAGTATATATGAGTAAACTTG

GTCTGACAGTTACCAATGCTTAATCAGTGAGGCACCTATCTCAGCGATCTGTCTATTTCGTT

CATCCATAGTTGCCTGACTCGGGGGGGGGGGGCGCTGAGGTCTGCCTCGTGAAGAAGGTGTT

GCTGACTCATACCAGGCCTGAATCGCCCCATCATCCAGCCAGAAAGTGAGGGAGCCACGGTT

GATGAGAGCTTTGTTGTAGGTGGACCAGTTGGTGATTTTGAACTTTTGCTTTGCCACGGAAC

GGTCTGCGTTGTCGGGAAGATGCGTGATCTGATCCTTCAACTCAGCAAAAGTTCGATTTATT

CAACAAAGCCGCCGTCCCGTCAAGTCAGCGTAATGCTCTGCCAGTGTTACAACCAATTAACC

AATTCTGATTAGAAAAACTCATCGAGCATCAAATGAAACTGCAATTTATTCATATCAGGATT

ATCAATACCATATTTTTGAAAAAGCCGTTTCTGTAATGAAGGAGAAAACTCACCGAGGCAGT

TCCATAGGATGGCAAGATCCTGGTATCGGTCTGCGATTCCGACTCGTCCAACATCAATACAA

CCTATTAATTTCCCCTCGTCAAAAATAAGGTTATCAAGTGAGAAATCACCATGAGTGACGAC

TGAATCCGGTGAGAATGGCAAAAGCTTATGCATTTCTTTCCAGACTTGTTCAACAGGCCAGC

CATTACGCTCGTCATCAAAATCACTCGCATCAACCAAACCGTTATTCATTCGTGATTGCGCC

TGAGCGAGACGAAATACGCGATCGCTGTTAAAAGGACAATTACAAACAGGAATCGAATGCAA

CCGGCGCAGGAACACTGCCAGCGCATCAACAATATTTTCACCTGAATCAGGATATTCTTCTA

ATACCTGGAATGCTGTTTTCCCGGGGATCGCAGTGGTGAGTAACCATGCATCATCAGGAGTA

CGGATAAAATGCTTGATGGTCGGAAGAGGCATAAATTCCGTCAGCCAGTTTAGTCTGACCAT

CTCATCTGTAACATCATTGGCAACGCTACCTTTGCCATGTTTCAGAAACAACTCTGGCGCAT

CGGGCTTCCCATACAATCGATAGATTGTCGCACCTGATTGCCCGACATTATCGCGAGCCCAT

TTATACCCATATAAATCAGCATCCATGTTGGAATTTAATCGCGGCCTCGAGCAAGACGTTTC

-continued

CCGTTGAATATGGCTCATAACACCCCTTGTATTACTGTTTATGTAAGCAGACAGTTTTATTG

TTCATGATGATATATTTTTATCTTGTGCAATGTAACATCAGAGATTTTGAGACACAACGTGG

ATCATCCAGACATGATAAGATACATTGATGAGTTTGGACAAACCACAACTAGAATGCAGTGA

AAAAAATGCTTTATTTGTGAAATTTGTGATGCTATTGCTTTATTTGTAACCATTATAAGCTG

CAATAAACAAGTTAACAACAACAATTGCATTCATTTTATGTTTCAGGTTCAGGGGGAGGTGT

GGGAGGTTTTTTAAAGCAAGTAAAACCTCTACAAATGTGGTATGGCTGATTATGATCGTCGA

GGATCTGGATCTGGATCCGTTAACCGATATCCGCGAATTCGGCGCGCCGGGCCCTCACGACG

TGTTGATGAACATCTGGACGATGTGCACGAACGACTGCAGGAACTCCTTGATGTTCTTCTCC

TCCAGCTCCTCGCACTCCTTGCAGCCCGACTCCGTGACGTTCCCGTTCGACGACAGCGAGTT

GTTCGCCAGGATGATCAGGTTCTCCACCGTGTCGTGGATCGACGCGTCCCCCGACTCGAGCG

AGATGACTTGGAGCTCCAGGAGGAAGCACTTCATCGCCGTGACCTTGCACGACGGGTGGACG

TCCGACTCCGTGTACAGCGTCGCGTCGATGTGCATCGACTGGATGAGGTCCTCGATCTTCTT

CAGGTCCGAGATCACGTTCACCCAGTTTCTGGCTCCTCTTCTGAATCGGGCATGGATTTCCT

GGCTGGGCGAAACGAAGACTGCTCCACACAGCAGCAGCACACAGCAGAGCCCTCTCTTCATT

GCATCCATTTCTTGTCGACAGATCCAAACGCTCCTCCGACGTCCCCAGGCAGAATGGCGGTT

CCCTAAACGAGCATTGCTTATATAGACCTCCCATTAGGCACGCCTACCGCCCATTTACGTCA

ATGGAACGCCCATTTGCGTCATTGCCCCTCCCCATTGACGTCAATGGGGATGTACTTGGCAG

CCATCGCGGGCCATTTACCGCCATTGACGTCAATGGGAGTACTGCCAATGTACCCTGGCGTA

CTTCCAATAGTAATGTACTTGCCAAGTTACTATTAATAGATATTGATGTACTGCCAAGTGGG

CCATTTACCGTCATTGACGTCAATAGGGGGCGTGAGAACGGATATGAATGGGCAATGAGCCA

TCCCATTGACGTCAATGGTGGGTGGTCCTATTGACGTCAATGGGCATTGAGCCAGGCGGGCC

ATTTACCGTAATTGACGTCAATGGGGGAGGCGCCATATACGTCAATAGGACCGCCCATATGA

CGTCAATAGGAAAGACCATGAGGCCCTTTCGTCTCGCGCGTTTCGGTGATGACGGTGAAAAC

CTCTGACACATGCAGCTCCCGGAGACGGTCACAGCTTGTCTGTAAGCGGATGCCGGGAGCAG

ACAAGCCCGTCAGGGCGCGTCAGCGGGTGTTGGCGGGTGTCGGGGCTGGCTTAACTATGCGG

CATCAGAGCAGATTGTACTGAGAGTGCACCATATGCGGTGTGAAATACCGCACAGATGCGTA

AGGAGAAAATACCGCATCAGATTGGCTATTGG

SEQ ID NO: 16

DPhuIL15sRa205 FC + huGMIL15 The capitalized, bolded region is the coding region for the IL-15Receptor alpha 205 FC fusion cctggccattgcatacgttgtatccatatcataatatgtacatttatattggctcatgtcca acattaccgccatgttgacattgattattgactagttattaatagtaatcaattacggggtc attagttcatagcccatatatggagttccgcgttacataacttacggtaaatggcccgcctg gctgaccgcccaacgacccccgcccattgacgtcaataatgacgtatgttcccatagtaacg ccaatagggactttccattgacgtcaatgggtggagtatttacggtaaactgcccacttggc agtacatcaagtgtatcatatgccaagtacgccccctattgacgtcaatgatggtaaatggc ccgcctggcattatgcccagtacatgaccttatgggactttcctacttggcagtacatctac gtattagtcatcgctattaccatggtgatgcggttttggcagtacatcaatgggcgtggata gcggtttgactcacggggatttccaagtctccaccccattgacgtcaatgggagtttgtttt ggcaccaaaatcaacgggactttccaaaatgtcgtaacaactccgccccattgacgcaaatg ggcggtaggcgtgtacggtgggaggtctatataagcagagctcgtttagtgaaccgtcagat cgcctggagacgccatccacgctgttttgacctccatagaagacaccgggaccgatccagcc -continued tccgcgggcgcgcgtcgacgctagcaagaaATGGCCCCGAGGCGGGCGCGAGGCTGCCGGAC

CCTCGGTCTCCCGGCGCTGCTACTGCTCCTGCTGCTCCGGCCGCCGGCGACGCGGGGCATCA

CGTGCCCGCCCCCCATGTCCGTGGAGCACGCAGACATCTGGGTCAAGAGCTACAGCTTGTAC

TCCCGGGAGCGGTACATCTGCAACTCGGGTTTCAAGCGGAAGGCCGGCACGTCCAGCCTGAC

GGAGTGCGTGTTGAACAAGGCCACGAATGTCGCCCACTGGACGACCCCCTCGCTCAAGTGCA

TCCGCGACCCGGCCCTGGTTCACCAGCGGCCCGCGCCACCCTCCACCGTAACGACGGCGGGG

GTGACCCCGCAGCCGGAGAGCCTCTCCCCGTCGGGAAAGGAGCCCGCCGCGTCGTCGCCCAG

CTCGAACAACACGGCGGCCACAACTGCAGCGATCGTCCCGGGCTCCCAGCTGATGCCGTCGA

AGTCGCCGTCCACGGGAACCACGGAGATCAGCAGTCATGAGTCCTCCCACGGCACCCCCTCG

CAAACGACGGCCAAGAACTGGGAACTCACGGCGTCCGCCTCCCACCAGCCGCCGGGGGTGTA

TCCGCAAGGCCACAGCGACACCACGCCGAAGTCCTGCGACAAGACGCACACGTGCCCTCCCT

GCCCGGCGCCCGAGCTGCTGGGAGGTCCGAGCGTGTTCCTCTTCCCGCCCAAGCCGAAGGAC

ACGCTCATGATCTCGCGGACTCCCGAGGTCACCTGCGTCGTGGTAGACGTCAGCCACGAGGA

CCCGGAGGTCAAGTTCAACTGGTACGTTGACGGCGTAGAGGTGCACAACGCGAAGACGAAGC

CGCGGGAGGAGCAGTACAACTCGACGTACCGAGTCGTGTCGGTCCTGACCGTCCTGCACCAG

GACTGGCTCAACGGGAAGGAGTACAAGTGCAAGGTGTCGAACAAGGCGCTCCCTGCCCCGAT

CGAGAAGACGATCTCGAAGGCGAAGGGCCAGCCCAGGGAGCCCCAGGTCTACACGCTCCCGC

CATCGCGGGACGAGCTGACGAAGAACCAGGTTTCCCTGACGTGCCTCGTCAAGGGCTTCTAC

CCATCGGACATCGCGGTGGAGTGGGAGAGCAACGGGCAGCCGGAGAACAACTACAAGACCAC

GCCTCCGGTGCTCGACTCGGACGGGTCGTTCTTCCTCTACTCGAAGCTGACCGTCGACAAGA

GCCGGTGGCAGCAGGGCAACGTGTTCTCCTGCTCGGTGATGCACGAGGCCCTCCACAACCAC

TACACCCAGAAGTCGCTCAGTCTGAGCCCGGGGAAGTAATGAggatccgaattcgcggatat cggttaacggatccagatctgctgtgccttctagttgccagccatctgttgtttgcccctcc cccgtgccttccttgaccctggaaggtgccactcccactgtcctttcctaataaaatgagga aattgcatcgcattgtctgagtaggtgtcattctattctggggggtggggtggggcaggaca gcaagggggaggattgggaagacaatagcaggcatgctggggatgcggtgggctctatgggt acccaggtgctgaagaattgacccggttcctcctgggccagaaagaagcaggcacatcccct tctctgtgacacaccctgtccacgcccctggttcttagttccagccccactcataggacact catagctcaggagggctccgccttcaatcccacccgctaaagtacttggagcggtctctccc tccctcatcagcccaccaaaccaaacctagcctccaagagtgggaagaaattaaagcaagat aggctattaagtgcagagggagagaaaatgcctccaacatgtgaggaagtaatgagagaaat catagaatttcttccgcttcctcgctcactgactcgctgcgctcggtcgttcggctgcggcg agcggtatcagctcactcaaaggcggtaatacggttatccacagaatcaggggataacgcag gaaagaacatgtgagcaaaaggccagcaaaaggccaggaaccgtaaaaaggccgcgttgctg gcgtttttccataggctccgcccccctgacgagcatcacaaaaatcgacgctcaagtcagag gtggcgaaacccgacaggactataaagataccaggcgtttccccctggaagctccctcgtgc gctctcctgttccgaccctgccgcttaccggatacctgtccgcctttctcccttcgggaagc gtggcgctttctcatagctcacgctgtaggtatctcagttcggtgtaggtcgttcgctccaa gctgggctgtgtgcacgaaccccccgttcagcccgaccgctgcgccttatccggtaactatc gtcttgagtccaacccggtaagacacgacttatcgccactggcagcagccactggtaacagg attagcagagcgaggtatgtaggcggtgctacagagttcttgaagtggtggcctaactacgg -continued

```
ctacactagaagaacagtatttggtatctgcgctctgctgaagccagttaccttcggaaaaa

gagttggtagctcttgatccggcaaacaaaccaccgctggtagcggtggtttttttgtttgc

aagcagcagattacgcgcagaaaaaaaggatctcaagaagatcctttgatcttttctacggg

gtctgacgctcagtggaacgaaaact

cacgttaagggattttggtcatgagattatcaaaaaggatcttcacctagatccttttaaat

taaaaatgaagttttaaatcaatctaaagtatatatgagtaaacttggtctgacagttacca

atgcttaatcagtgaggcacctatctcagcgatctgtctatttcgttcatccatagttgcct

gactcgggggggggggcgctgaggtctgcctcgtgaagaaggtgttgctgactcataccag

gcctgaatcgccccatcatccagccagaaagtgagggagccacggttgatgagagctttgtt

gtaggtggaccagttggtgattttgaacttttgctttgccacggaacggtctgcgttgtcgg

gaagatgcgtgatctgatccttcaactcagcaaaagttcgatttattcaacaaagccgccgt

cccgtcaagtcagcgtaatgctctgccagtgttacaaccaattaaccaattctgattagaaa

aactcatcgagcatcaaatgaaactgcaatttattcatatcaggattatcaataccatattt

ttgaaaaagccgtttctgtaatgaaggagaaaactcaccgaggcagttccataggatggcaa

gatcctggtatcggtctgcgattccgactcgtccaacatcaatacaacctattaatttcccc

tcgtcaaaaataaggttatcaagtgagaaatcaccatgagtgacgactgaatccggtgagaa

tggcaaaagcttatgcatttctttccagacttgttcaacaggccagccattacgctcgtcat

caaaatcactcgcatcaaccaaaccgttattcattcgtgattgcgcctgagcgagacgaaat

acgcgatcgctgttaaaaggacaattacaaacaggaatcgaatgcaaccggcgcaggaacac

tgccagcgcatcaacaatattttcacctgaatcaggatattcttctaatacctggaatgctg

ttttcccggggatcgcagtggtgagtaaccatgcatcatcaggagtacggataaaatgcttg

atggtcggaagaggcataaattccgtcagccagtttagtctgaccatctcatctgtaacatc

attggcaacgctacctttgccatgtttcagaaacaactctggcgcatcgggcttcccataca

atcgatagattgtcgcacctgattgcccgacattatcgcgagcccatttatacccatataaa

tcagcatccatgttggaatttaatcgcggcctcgagcaagacgtttcccgttgaatatggct

cataacaccccttgtattactgtttatgtaagcagacagttttattgttcatgatgatatat

ttttatcttgtgcaatgtaacatcagagattttgagacacaacgtggatcatccagacatga

taagatacattgatgagtttggacaaaccacaactagaatgcagtgaaaaaaatgctttatt

tgtgaaatttgtgatgctattgctttatttgtaaccattataagctgcaataaacaagttaa

caacaacaattgcattcattttatgtttcaggttcagggggaggtgtgggaggttttttaaa

gcaagtaaaacctctacaaatgtggtatggctgattatgatcgtcgaggatctggatccgtt

aaccgatatccgcgaattcggcgcgccgggcccTCACGACGTGTTGATGAACATCTGGACGA

TGTGCACGAACGACTGCAGGAACTCCTTGATGTTCTTCTCCTCCAGCTCCTCGCACTCCTTG

CAGCCCGACTCCGTGACGTTCCCGTTCGACGACAGCGAGTTGTTCGCCAGGATGATCAGGTT

CTCCACCGTGTCGTGGATCGACGCGTCCCCCGACTCGAGCGAGATGACTTGGAGCTCCAGGA

GGAAGCACTTCATCGCCGTGACCTTGCACGACGGGTGGACGTCCGACTCCGTGTACAGCGTC

GCGTCGATGTGCATCGACTGGATGAGGTCCTCGATCTTCTTCAGGTCCGAGATCACGTTCAC

CCAGTTCGAGATGCTGCAGGCCACCGTCCCCAGGAGTAGCAGGCTCTGGAGCCACATttctt

gtcgacagatccaaacgctcctccgacgtccccaggcagaatggcggttccctaaacgagca

ttgcttatatagacctcccattaggcacgcctaccgcccatttacgtcaatggaacgcccat

ttgcgtcattgcccctccccattgacgtcaatggggatgtacttggcagccatcgcgggcca
```

-continued

```
tttaccgccattgacgtcaatgggagtactgccaatgtaccctggcgtacttccaatagtaa
tgtacttgccaagttactattaatagatattgatgtactgccaagtgggccatttaccgtca
ttgacgtcaatagggggcgtgagaacggatatgaatgggcaatgagccatcccattgacgtc
aatggtgggtggtcctattgacgtcaatgggcattgagccaggcgggccatttaccgtaatt
gacgtcaatgggggaggcgccatatacgtcaataggaccgcccatatgacgtcaataggtaa
gaccatgaggccctttcgtctcgcgcgtttcggtgatgacggtgaaaacctctgacacatgc
agctcccggagacggtcacagcttgtctgtaagcggatgccgggagcagacaagcccgtcag
ggcgcgtcagcgggtgttggcgggtgtcggggctggcttaactatgcggcatcagagcagat
tgtactgagagtgcaccatatgcggtgtgaaataccgcacagatgcgtaaggagaaaatacc
gcatcagattggctattgg
```

SEQ ID NO: 17 huIL15sRa205-Fc-underlined region is IL15sRa sequence

```
M A P R R A R G C R T L G L P A L L L L L
L L R P P A T R G I T C P P P M S V E H A
D I W V K S Y S L Y S R E R Y I C N S G F
K R K A G T S S L T E C V L N K A T N V A
H W T T P S L K C I R D P A L V H Q R P A
P P S T V T T A G V T P Q P E S L S P S G
K E P A A S S P S S N N T A A T T A A I V
P G S Q L M P S K S P S T G T T E I S S H
E S S H G T P S Q T T A K N W E L T A S A
S H Q P P G V Y P Q G H S D T T P K S C D
K T H T C P P C P A P E L L G G P S V F L
F P P K P K D T L M I S R T P E V T C V V
V D V S H E D P E V K F N W Y V D G V E V
H N A K T K P R E E Q Y N S T Y R V V S V
L T V L H Q D W L N G K E Y K C K V S N K
A L P A P I E K T I S K A K G Q P R E P Q
V Y T L P P S R D E L T K N Q V S L T C L
V K G F Y P S D I A V E W E S N G Q P E N
N Y K T T P P V L D S D G S F F L Y S K L
T V D K S R W Q Q G N V F S C S V M H E A
L H N H Y T Q K S L S L S P G K
```

SEQ ID NO: 18 huGMCSF-IL15

```
M W L Q S L L L L G T V A C S I S N W V N
V I S D L K K I E D L I Q S M H I D A T L
Y T E S D V H P S C K V T A M K C F L L E
L Q V I S L E S G D A S I H D T V E N L I
I L A N N S L S S N G N V T E S G C K E C
E E L E E K N I K E F L Q S F V H I V Q M
F I N T S
```

-continued

SEQ ID NO: 19

AG256DPhuIL15sRa200 FC + huGMIL15-The capitalized, bolded region is the coding region for the IL-15Receptor alpha 200 FC fusion cctggccattgcatacgttgtatccatatcataatatgtacatttatattggctcatgtcca acattaccgccatgttgacattgattattgactagttattaatagtaatcaattacggggtc attagttcatagcccatatatggagttccgcgttacataacttacggtaaatggcccgcctg gctgaccgcccaacgacccccgcccattgacgtcaataatgacgtatgttcccatagtaacg ccaatagggactttccattgacgtcaatgggtggagtatttacggtaaactgcccacttggc agtacatcaagtgtatcatatgccaagtacgccccctattgacgtcaatgatggtaaatggc ccgcctggcattatgcccagtacatgaccttatgggactttcctacttggcagtacatctac gtattagtcatcgctattaccatggtgatgcggttttggcagtacatcaatgggcgtggata gcggtttgactcacggggatttccaagtctccaccccattgacgtcaatgggagtttgtttt ggcaccaaaatcaacgggactttccaaaatgtcgtaacaactccgccccattgacgcaaatg ggcggtaggcgtgtacggtgggaggtctatataagcagagctcgtttagtgaaccgtcagat cgcctggagacgccatccacgctgttttgacctccatagaagacaccgggaccgatccagcc tccgcgggcgcgcgtcgacgctagcaagaaATGGCCCCGAGGCGGGCGCGAGGCTGCCGGAC

CCTCGGTCTCCCGGCGCTGCTACTGCTCCTGCTGCTCCGGCCGCCGGCGACGCGGGGCATCA

CGTGCCCGCCCCCCATGTCCGTGGAGCACGCAGACATCTGGGTCAAGAGCTACAGCTTGTAC

TCCCGGGAGCGGTACATCTGCAACTCGGGTTTCAAGCGGAAGGCCGGCACGTCCAGCCTGAC

GGAGTGCGTGTTGAACAAGGCCACGAATGTCGCCCACTGGACGACCCCCTCGCTCAAGTGCA

TCCGCGACCCGGCCCTGGTTCACCAGCGGCCCGCGCCACCCTCCACCGTAACGACGGCGGGG

GTGACCCCGCAGCCGGAGAGCCTCTCCCCGTCGGGAAAGGAGCCCGCCGCGTCGTCGCCCAG

CTCGAACAACACGGCGGCCACAACTGCAGCGATCGTCCCGGGCTCCCAGCTGATGCCGTCGA

AGTCGCCGTCCACGGGAACCACGGAGATCAGCAGTCATGAGTCCTCCCACGGCACCCCCTCG

CAAACGACGGCCAAGAACTGGGAACTCACGGCGTCCGCCTCCCACCAGCCGCCGGGGGTGTA

TCCGCAAGGCCCGAAGTCCTGCGACAAGACGCACACGTGCCCTCCCTGCCCGGCGCCCGAGC

TGCTGGGAGGTCCGAGCGTGTTCCTCTTCCCGCCCAAGCCGAAGGACACGCTCATGATCTCG

CGGACTCCCGAGGTCACCTGCGTCGTGGTAGACGTCAGCCACGAGGACCCGGAGGTCAAGTT

CAACTGGTACGTTGACGGCGTAGAGGTGCACAACGCGAAGACGAAGCCGCGGGAGGAGCAGT

ACAACTCGACGTACCGAGTCGTGTCGGTCCTGACCGTCCTGCACCAGGACTGGCTCAACGGG

AAGGAGTACAAGTGCAAGGTGTCGAACAAGGCGCTCCCTGCCCCGATCGAGAAGACGATCTC

GAAGGCGAAGGGCCAGCCCAGGGAGCCCCAGGTCTACACGCTCCCGCCATCGCGGGACGAGC

TGACGAAGAACCAGGTTTCCCTGACGTGCCTCGTCAAGGGCTTCTACCCATCGGACATCGCG

GTGGAGTGGGAGAGCAACGGGCAGCCGGAGAACAACTACAAGACCACGCCTCCGGTGCTCGA

CTCGGACGGGTCGTTCTTCCTCTACTCGAAGCTGACCGTCGACAAGAGCCGGTGGCAGCAGG

GCAACGTGTTCTCCTGCTCGGTGATGCACGAGGCCCTCCACAACCACTACACCCAGAAGTCG

CTCAGTCTGAGCCCGGGGAAGTAATGAggatccgaattcgcggatatcggttaacggatcca gatctgctgtgccttctagttgccagccatctgttgtttgcccctcccccgtgccttccttg accctggaaggtgccactcccactgtcctttcctaataaaatgaggaaattgcatcgcattg tctgagtaggtgtcattctattctggggggtggggtggggcaggacagcaagggggaggatt gggaagacaatagcaggcatgctggggatgcggtgggctctatgggtacccaggtgctgaag aattgacccggttcctcctgggccagaaagaagcaggcacatccccttctctgtgacacacc -continued

```
ctgtccacgcccctggttcttagttccagccccactcataggacactcatagctcaggaggg
ctccgccttcaatcccacccgctaaagtacttggagcggtctctccctccctcatcagccca
ccaaaccaaacctagcctccaagagtgggaagaaattaaagcaagataggctattaagtgca
gagggagagaaaatgcctccaacatgtgaggaagtaatgagagaaatcatagaatttcttcc
gcttcctcgctcactgactcgctgcgctcggtcgttcggctgcggcgagcggtatcagctca
ctcaaaggcggtaatacggttatccacagaatcaggggataacgcaggaaagaacatgtgag
caaaaggccagcaaaaggccaggaaccgtaaaaaggccgcgttgctggcgtttttccatagg
ctccgcccccctgacgagcatcacaaaaatcgacgctcaagtcagaggtggcgaaacccgac
aggactataaagataccaggcgtttccccctggaagctccctcgtgcgctctcctgttccga
ccctgccgcttaccggatacctgtccgcctttctcccttcgggaagcgtggcgctttctcat
agctcacgctgtaggtatctcagttcggtgtaggtcgttcgctccaagctgggctgtgtgca
cgaaccccccgttcagcccgaccgctgcgccttatccggtaactatcgtcttgagtccaacc
cggtaagacacgacttatcgccactggcagcagccactggtaacaggattagcagagcgagg
tatgtaggcggtgctacagagttcttgaagtggtggcctaactacggctacactagaagaac
agtatttggtatctgcgctctgctgaagccagttaccttcggaaaaagagttggtagctctt
gatccggcaaacaaaccaccgctggtagcggtggtttttttgtttgcaagcagcagattacg
cgcagaaaaaaaggatctcaagaagatcctttgatcttttctacggggtctgacgctcagtg
gaacgaaaactcacgttaagggattttggtcatgagattatcaaaaaggatcttcacctaga
tccttttaaattaaaaatgaagttttaaatcaatctaaagtatatatgagtaaacttggtct
gacagttaccaatgcttaatcagtgaggcacctatctcagcgatctgtctatttcgttcatc
catagttgcctgactcgggggggggggggcgctgaggtctgcctcgtgaagaaggtgttgctg
actcataccaggcctgaatcgccccatcatccagccagaaagtgagggagccacggttgatg
agagctttgttgtaggtggaccagttggtgattttgaacttttgctttgccacggaacggtc
tgcgttgtcgggaagatgcgtgatctgatccttcaactcagcaaaagttcgatttattcaac
aaagccgccgtcccgtcaagtcagcgtaatgctctgccagtgttacaaccaattaaccaatt
ctgattagaaaaactcatcgagcatcaaatgaaactgcaatttattcatatcaggattatca
ataccatatttttgaaaaagccgtttctgtaatgaaggagaaaactcaccgaggcagttcca
taggatggcaagatcctggtatcggtctgcgattccgactcgtccaacatcaatacaaccta
ttaatttcccctcgtcaaaaataaggttatcaagtgagaaatcaccatgagtgacgactgaa
tccggtgagaatggcaaaagcttatgcatttctttccagacttgttcaacaggccagccatt
acgctcgtcatcaaaatcactcgcatcaaccaaaccgttattcattcgtgattgcgcctgag
cgagacgaaatacgcgatcgctgttaaaaggacaattacaaacaggaatcgaatgcaaccgg
cgcaggaacactgccagcgcatcaacaatattttcacctgaatcaggatattcttctaatac
ctggaatgctgttttcccggggatcgcagtggtgagtaaccatgcatcatcaggagtacgga
taaaatgcttgatggtcggaagaggcataaattccgtcagccagtttagtctgaccatctca
tctgtaacatcattggcaacgctacctttgccatgtttcagaaacaactctggcgcatcggg
cttcccatacaatcgatagattgtcgcacctgattgcccgacattatcgcgagcccatttat
acccatataaatcagcatccatgttggaatttaatcgcggcctcgagcaagacgtttcccgt
tgaatatggctcataacaccccttgtattactgtttatgtaagcagacagttttattgttca
tgatgatatatttttatcttgtgcaatgtaacatcagagattttgagacacaacgtggatca
tccagacatgataagatacattgatgagtttggacaaaccacaactagaatgcagtgaaaaa
```

-continued

```
aatgctttatttgtgaaatttgtgatgctattgctttatttgtaaccattataagctgcaat
aaacaagttaacaacaacaattgcattcattttatgtttcaggttcagggggaggtgtggga
ggtttttttaaagcaagtaaaacctctacaaatgtggtatggctgattatgatcgtcgaggat
ctggatccgttaaccgatatccgcgaattcggcgcgccgggcccTCACGACGTGTTGATGAA
CATCTGGACGATGTGCACGAACGACTGCAGGAACTCCTTGATGTTCTTCTCCTCCAGCTCCT
CGCACTCCTTGCAGCCCGACTCCGTGACGTTCCCGTTCGACGACAGCGAGTTGTTCGCCAGG
ATGATCAGGTTCTCCACCGTGTCGTGGATCGACGCGTCCCCCGACTCGAGCGAGATGACTTG
GAGCTCCAGGAGGAAGCACTTCATCGCCGTGACCTTGCACGACGGGTGGACGTCCGACTCCG
TGTACAGCGTCGCGTCGATGTGCATCGACTGGATGAGGTCCTCGATCTTCTTCAGGTCCGAG
ATCACGTTCACCCAGTTCGAGATGCTGCAGGCCACCGTCCCCAGGAGTAGCAGGCTCTGGAG
CCACATttcttgtcgacagatccaaacgctcctccgacgtccccaggcagaatggcggttcc
ctaaacgagcattgcttatatagacctcccattaggcacgcctaccgcccatttacgtcaat
ggaacgcccatttgcgtcattgcccctccccattgacgtcaatggggatgtacttggcagcc
atcgcgggccatttaccgccattgacgtcaatgggagtactgccaatgtaccctggcgtact
tccaatagtaatgtacttgccaagttactattaatagatattgatgtactgccaagtgggcc
atttaccgtcattgacgtcaataggggggcgtgagaacggatatgaatgggcaatgagccatc
ccattgacgtcaatggtgggtggtcctattgacgtcaatgggcattgagccaggcgggccat
ttaccgtaattgacgtcaatgggggaggcgccatatacgtcaataggaccgcccatatgacg
tcaataggtaagaccatgaggccctttcgtctcgcgcgtttcggtgatgacggtgaaaacct
ctgacacatgcagctcccggagacggtcacagcttgtctgtaagcggatgccgggagcagac
aagcccgtcagggcgcgtcagcgggtgttggcgggtgtcggggctggcttaactatgcggca
tcagagcagattgtactgagagtgcaccatatgcggtgtgaaataccgcacagatgcgtaag
gagaaaataccgcatcagattggctattgg
```

SEQ ID NO: 20 huIL15sRa200-Fc

```
M A P R R A R G C R T L G L P A L L L L L
L L R P P A T R G I T C P P P M S V E H A
D I W V K S Y S L Y S R E R Y I C N S G F
K R K A G T S S L T E C V L N K A T N V A
H W T T P S L K C I R D P A L V H Q R P A
P P S T V T T A G V T P Q P E S L S P S G
K E P A A S S P S S N N T A A T T A A I V
P G S Q L M P S K S P S T G T T E I S S H
E S S H G T P S Q T T A K N W E L T A S A
S H Q P P G V Y P Q G P K S C D K T H T C
P P C P A P E L L G G P S V F L F P P K P
K D T L M I S R T P E V T C V V V D V S H
E D P E V K F N W Y V D G V E V H N A K T
K P R E E Q Y N S T Y R V V S V L T V L H
Q D W L N G K E Y K C K V S N K A L P A P
I E K T I S K A K G Q P R E P Q V Y T L P
P S R D E L T K N Q V S L T C L V K G F Y
```

-continued

P S D I A V E W E S N G Q P E N N Y K T T

P P V L D S D G S F F L Y S K L T V D K S

R W Q Q G N V F S C S V M H E A L H N H Y

T Q K S L S L S P G K

---

What is claimed is:

1. A method of treating lymphopenia in an individual in need thereof comprising systemically administering to the individual a heterodimer comprising (i) an interleukin-15 (IL-15) and (ii) an IL-15Rα-Fc fusion protein that comprises a soluble IL-15Rα fused to an Fc region; wherein the IL-15 has at least 95% amino acid sequence identity to the region of SEQ ID NO:2 that corresponds to mature IL-15; and the IL-15Rα-Fc fusion protein comprises an amino acid sequence that has at least 95% amino acid sequence identity to the IL-15Rα-Fc fusion protein sequence of SEQ ID NO:17 or SEQ ID NO:20;

wherein the heterodimer is administered at a dose that maintains supraphysiological plasma levels of IL-15 for two or more days.

2. The method of claim 1, wherein the lymphopenia is drug-induced lymphopenia.

3. The method of claim 1, wherein the individual is receiving anticancer drugs that induce lymphopenia.

4. The method of claim 1, wherein the heterodimer is administered subcutaneously.

5. The method of claim 1, wherein the supraphysiological plasma levels of IL-15 are in the range of 1 ng/ml to 1000 ng/ml.

6. The method of claim 1, wherein the heterodimer is administered in an amount of 0.01 mg/kg.

7. The method of claim 1, wherein the individual is a human.

8. The method of claim 1, wherein the IL-15 comprises the region of SEQ ID NO:2 that corresponds to mature IL-15 and the IL-15Rα-Fc fusion protein comprises the IL-15Rα-Fc fusion protein sequence of SEQ ID NO:17 or SEQ ID NO:20.

9. A method of treating lymphopenia in an individual in need thereof comprising administering: (i) a nucleic acid sequence that encodes an IL-15 and (ii) a nucleic acid sequence that encodes an IL-15Rα-Fc fusion protein that comprises soluble IL-15Ra fused to an Fc region; wherein the IL-15 has at least 95% amino acid sequence identity to the region of SEQ ID NO:2 that corresponds to mature IL-15 and the IL-15Rα-Fc fusion protein has at least 95% identity to the IL-15Rα-Fc fusion protein sequence of SEQ ID NO:17 or SEQ ID NO:20;

wherein the nucleic acid sequence that encodes the IL-15 and the nucleic acid sequence that encodes the IL-15Rα-Fc fusion protein are administered at a dose that maintains supraphysiological plasma levels of IL-15 for two or more days.

10. The method of claim 9, wherein the IL-15 and the IL-15Rα-Fc fusion protein are co-expressed from a single vector comprising the nucleic acid sequence that encodes the IL-15 and the nucleic acid sequence that encodes the IL IL-15Rα-Fc fusion protein.

11. The method of claim 9, wherein the IL-15 and the IL-15Rα-Fc fusion protein are expressed from separate vectors, wherein one vector comprises the nucleic acid sequence that encodes the IL-15 and a separate vector comprises the nucleic acid sequence that encodes the IL-15Rα-Fc fusion protein.

12. The method of claim 9, wherein the IL-15 comprises the region of SEQ ID NO:2 that corresponds to mature IL-15 and the IL-15Rα-Fc fusion protein comprises the IL-15Rα-Fc fusion protein sequence of SEQ ID NO:17 or SEQ ID NO:20.

13. The method of claim 12, wherein the nucleic acid sequence that encodes IL-15 comprises the region of SEQ ID NO:3 or SEQ ID NO:4 that encodes mature IL-15; and the nucleic acid sequence that encodes the IL-15Rα-Fc fusion protein comprises the nucleic acid sequence of SEQ ID NO:16 or SEQ ID NO:19 that encodes the IL-15Rα-Fc fusion protein.

14. The method of claim 9, wherein the supraphysiological plasma levels of IL-15 are in the range of 1 ng/ml to 1000 ng/ml.

15. The method of claim 9, wherein the individual is a human.

* * * * *